United States Patent [19]

Law et al.

[11] Patent Number: 5,395,752
[45] Date of Patent: Mar. 7, 1995

[54] LONG EMISSION WAVELENGTH CHEMILUMINESCENT COMPOUNDS AND THEIR USE IN TEST ASSAYS

[75] Inventors: Say-Jong Law, Westwood; Qingping Jiang, Norwood, both of Mass.; Walter Fischer, Reinach, Switzerland; John T. Unger, Medfield; Elizabeth K. Krodel, Arlington, both of Mass.

[73] Assignees: Ciba Corning Diagnostics Corp.; Ciba-Geigy A.G., Medfield, Mass.

[21] Appl. No.: 35,130

[22] Filed: Mar. 19, 1993

[51] Int. Cl.6 ................ C12Q 1/68; G01N 33/48; C12P 19/34
[52] U.S. Cl. .................. 435/6; 435/7.1; 435/91.2; 435/968; 436/172; 436/501; 436/518; 436/536; 436/805; 546/102
[58] Field of Search ............ 435/6, 7.1, 91.2, 968; 935/78; 546/102; 436/172, 501, 518, 536, 805

[56] References Cited

U.S. PATENT DOCUMENTS

| | | | |
|---|---|---|---|
| 4,683,202 | 7/1987 | Mullis | 435/91 |
| 5,110,932 | 5/1992 | Law et al. | 546/102 |

FOREIGN PATENT DOCUMENTS

| | | |
|---|---|---|
| 2233450 | 1/1991 | United Kingdom . |
| 9212255 | 7/1992 | WIPO . |

*Primary Examiner*—Margaret Parr
*Assistant Examiner*—Kenneth R. Horlick
*Attorney, Agent, or Firm*—Nicholas I. Slepchuk, Jr.; Arthur S. Morgenstern; Judith A. Roesler

[57] ABSTRACT

An assay method incorporating at least two different chemiluminescent compounds for detection and/or quantitation of at least two substances in a test sample is described. The synthesis of chemiluminescent reagents or conjugates for use in such methods as well as kits incorporating such reagents are also disclosed. The assays have particular application in the field of clinical diagnostics.

26 Claims, 31 Drawing Sheets

FIG. IA
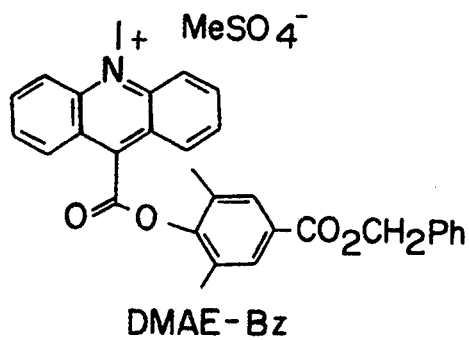
DMAE-Bz
FIG. IB
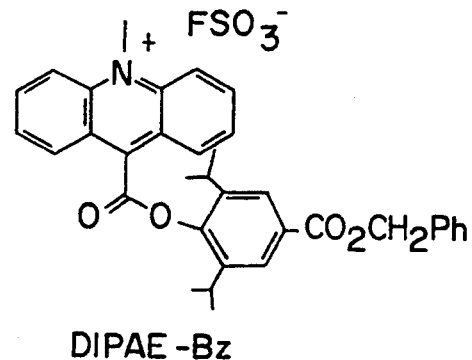
DIPAE-Bz
FIG. IC
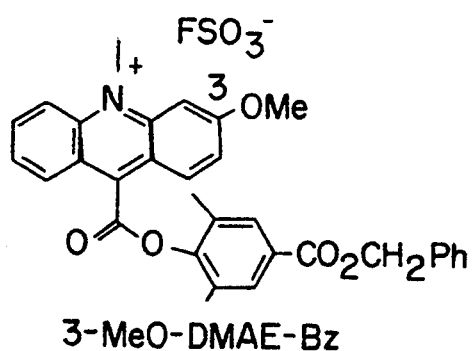
3-MeO-DMAE-Bz
FIG. ID
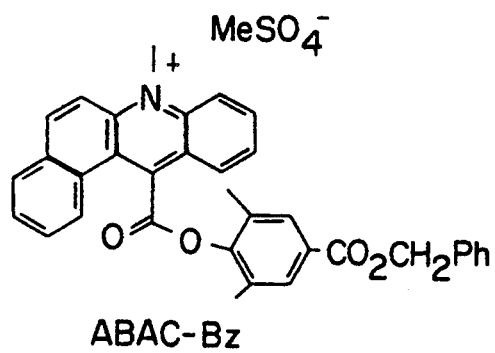
ABAC-Bz
FIG. IE
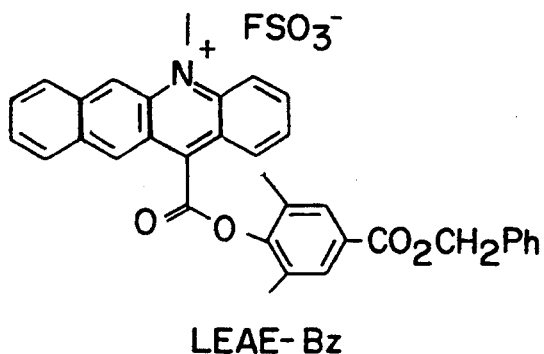
LEAE-Bz
FIG. IF
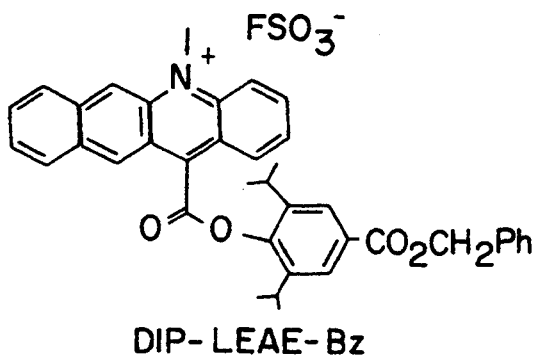
DIP-LEAE-Bz LEAC-Bz 3-EtO-LEAE-Bz 3-QAE-LEAE-Bz 2-MeO-LEAE-Bz 2-QAE-LEAE-Bz NSP-LEAE-Bz

FIG.IM
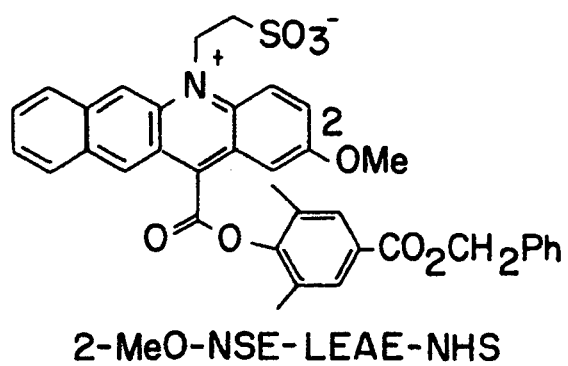
2-MeO-NSE-LEAE-NHS
FIG.IN
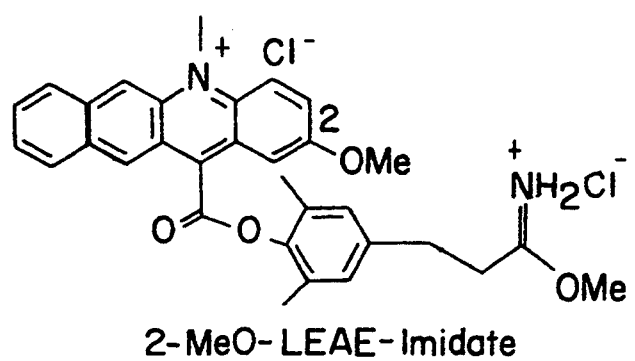
2-MeO-LEAE-Imidate

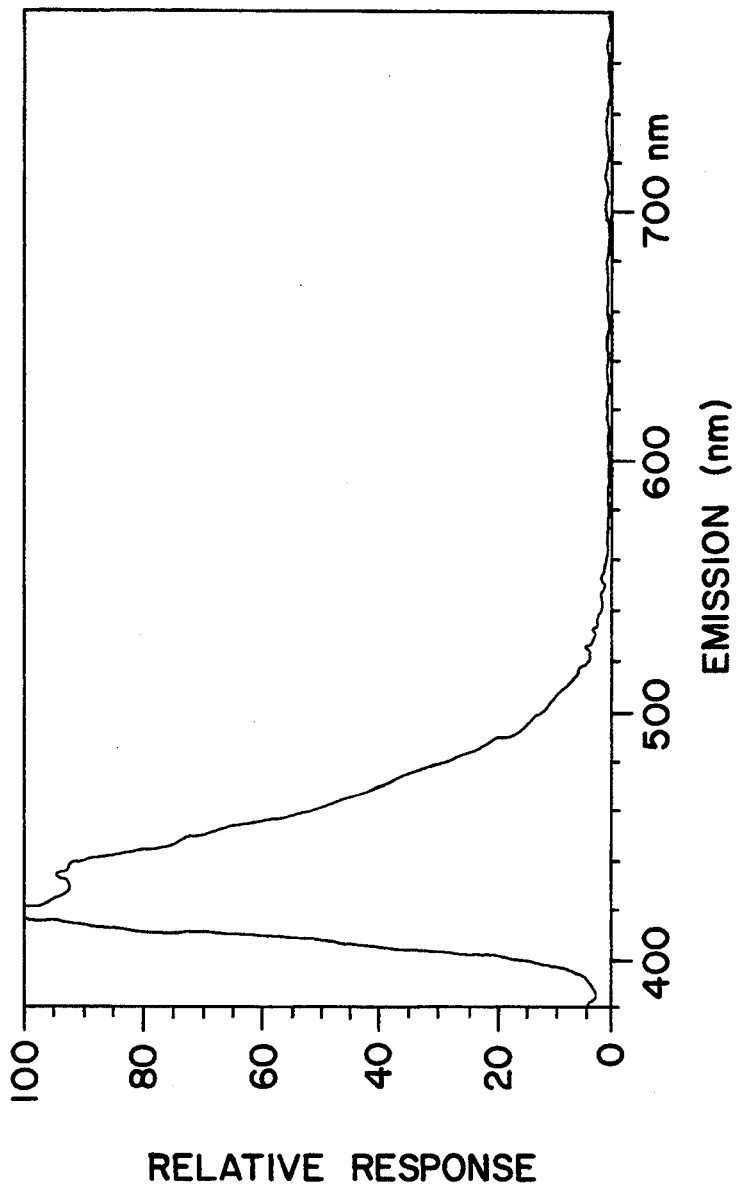

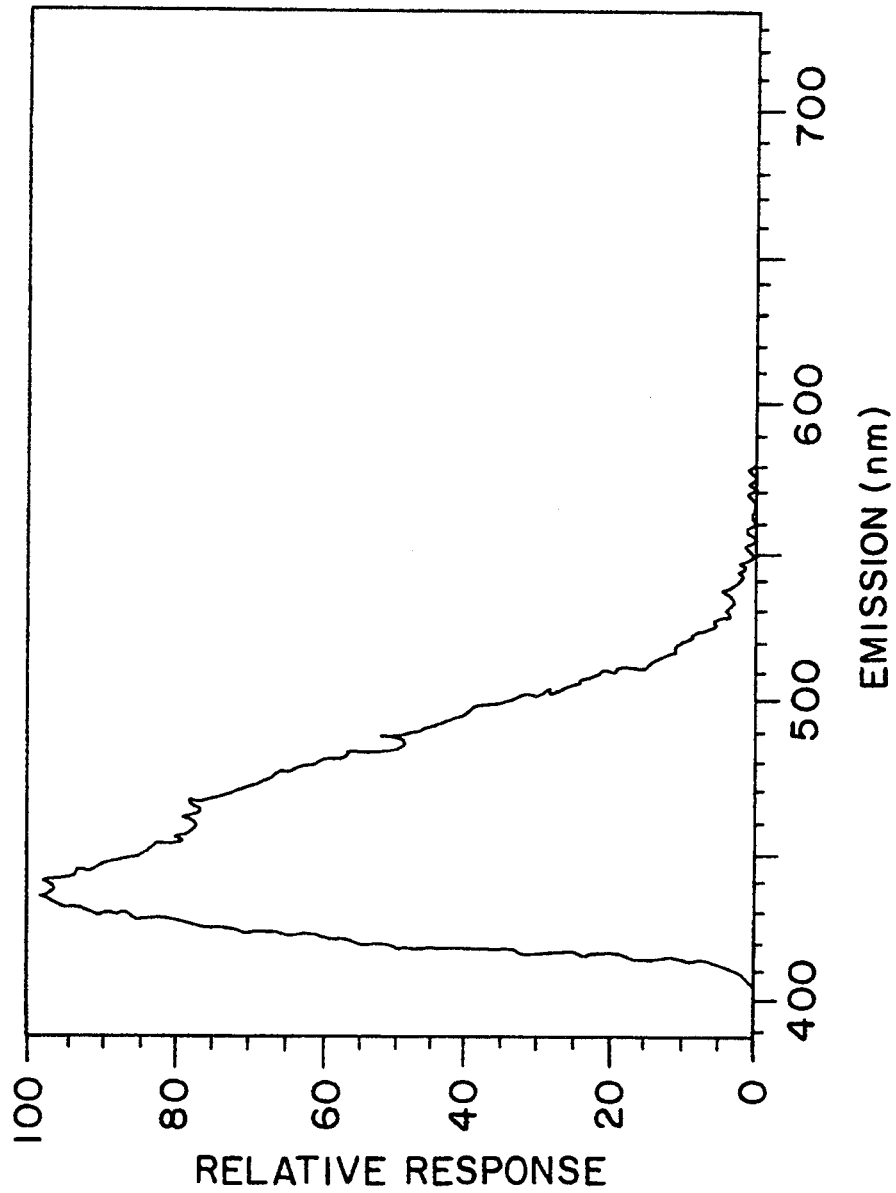

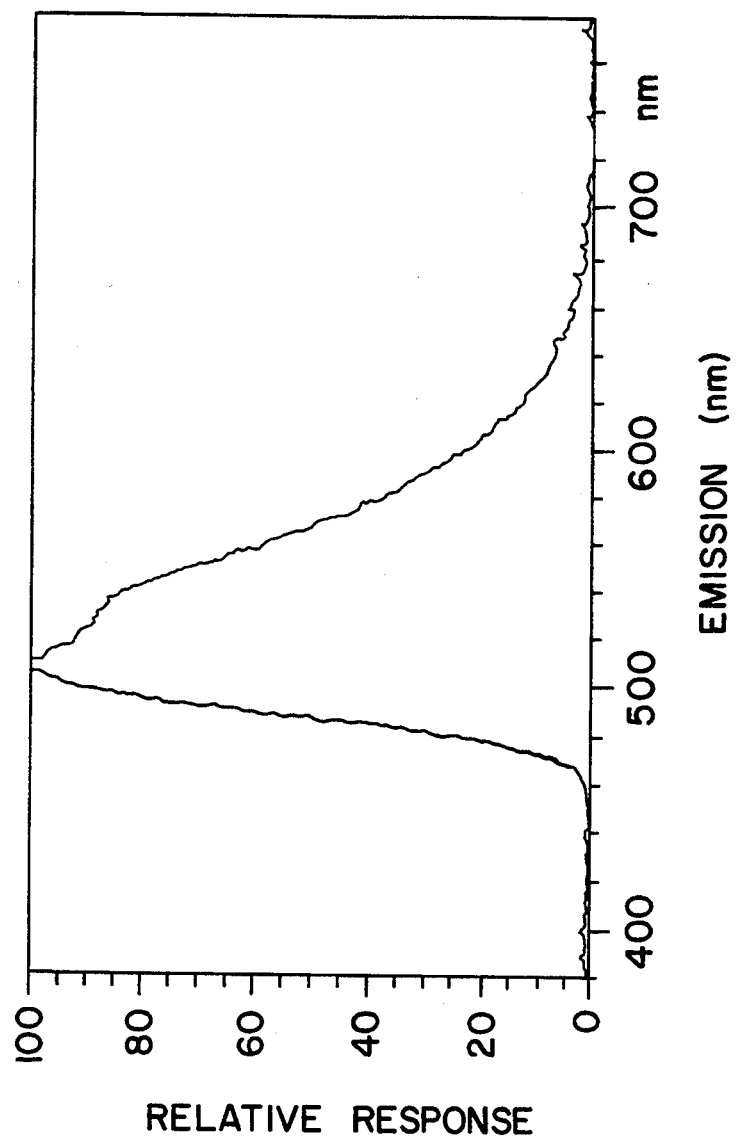

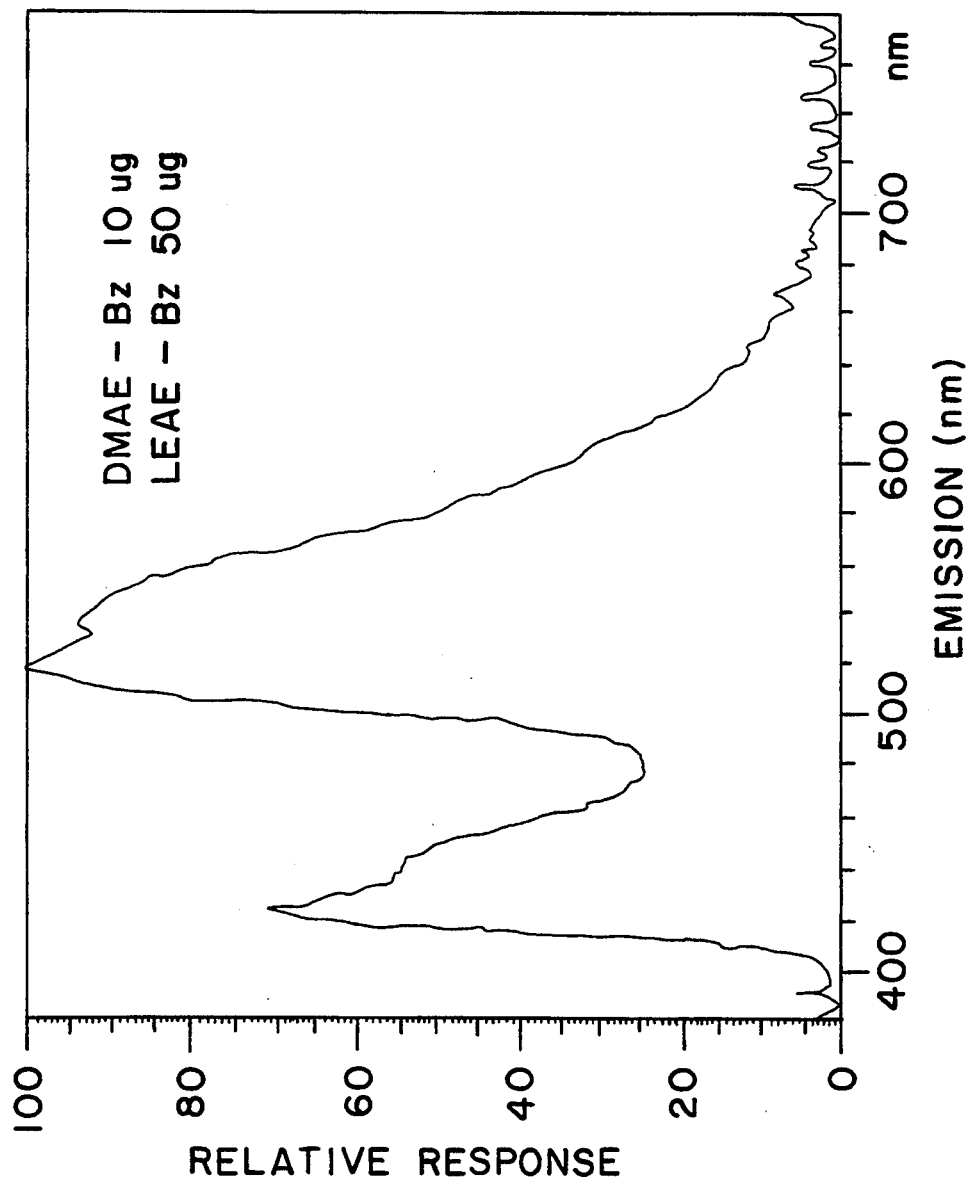

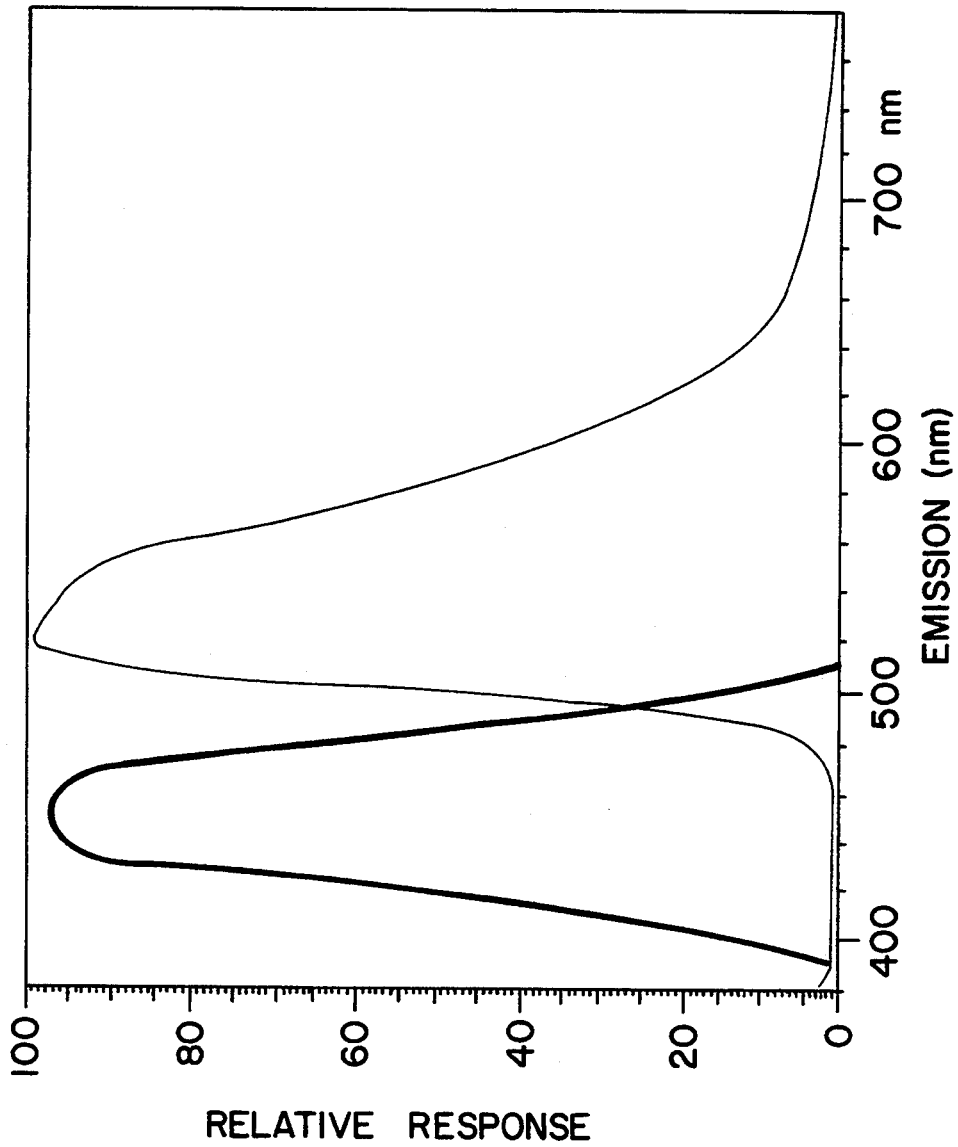

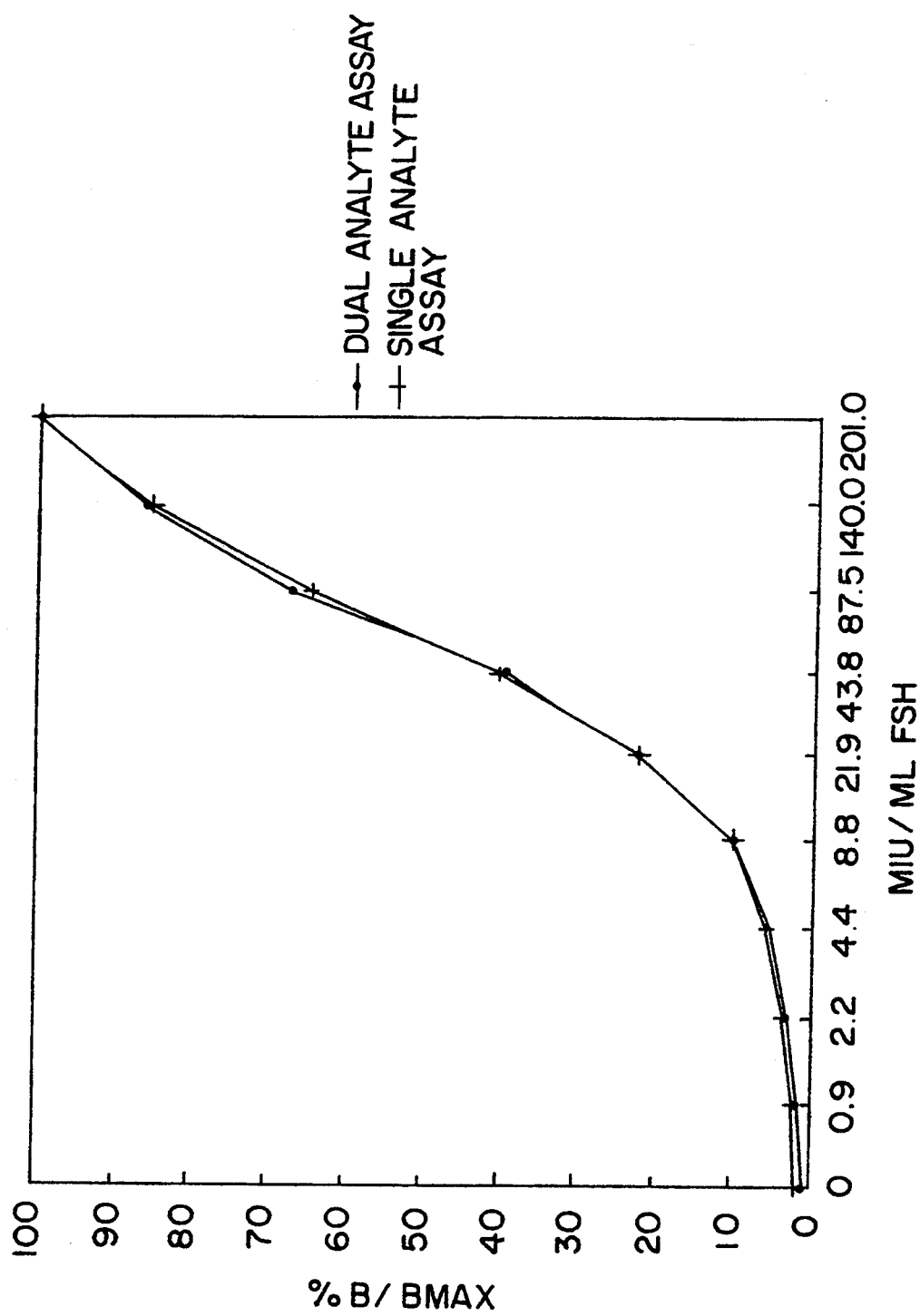

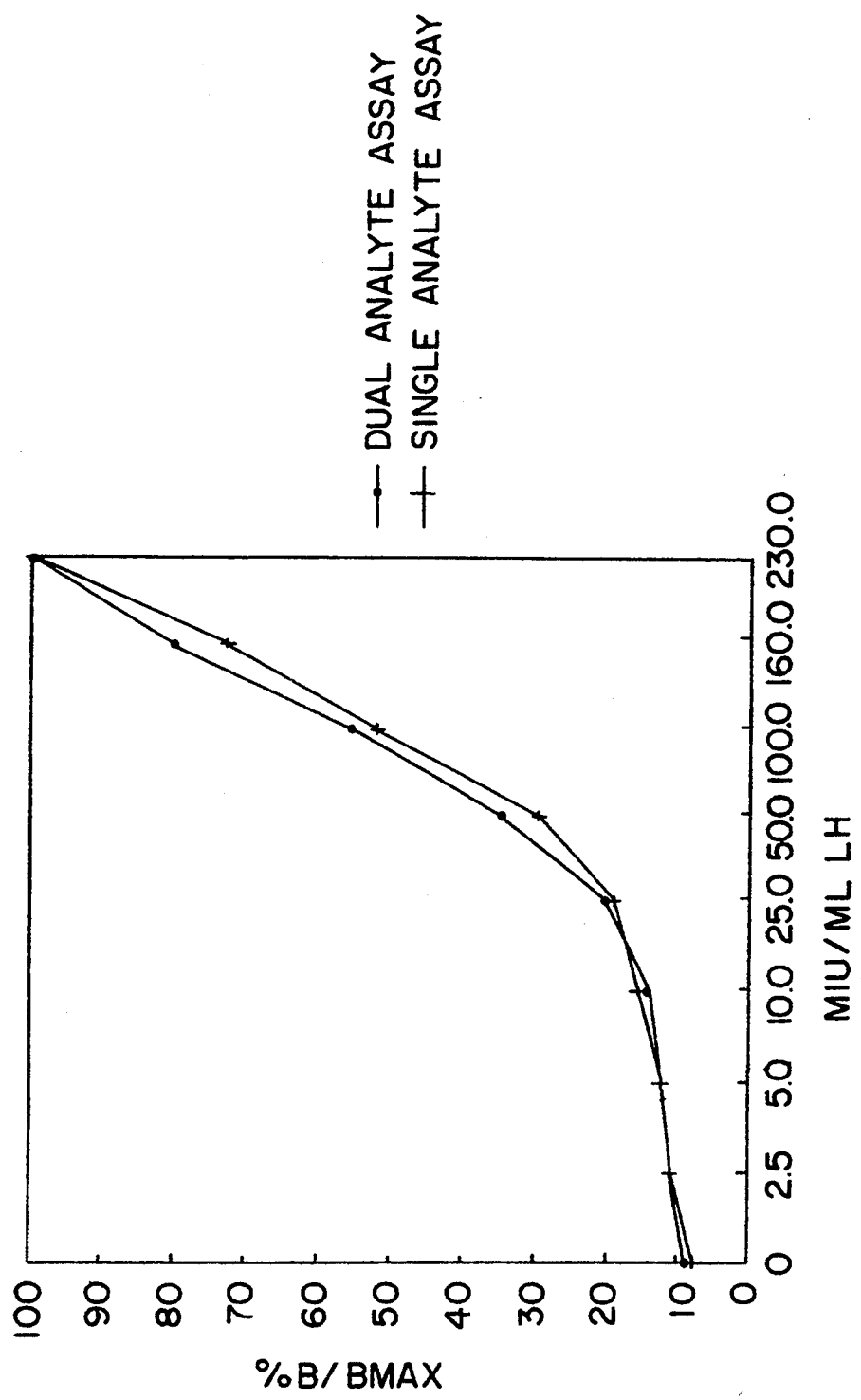

ND EMISSION WAVELENGTH
LONG EMISSION WAVELENGTH CHEMILUMINESCENT COMPOUNDS AND THEIR USE IN TEST ASSAYS

BACKGROUND OF THE INVENTION

1. Technical Field

The present invention relates to a new class of chemiluminescent, aromatic ring-fused acridinium compounds (AFAC) which emit green or yellow light upon simple chemical treatments. This invention also relates to conjugates formed from AFAC and binding partners, e.g. biological molecules, and test assays utilizing the conjugates. Furthermore the invention relates to test assays in which the detection and/or quantitation of two or more substances or analytes in a test sample can be carried out simultaneously due to the discernable and non-interfering light emission characteristics of two or more chemiluminescent conjugates.

2. Cross-Reference

The following application, filed concurrently herewith, describes a luminometer for detecting emission spectra of at least two chemiluminescent compounds in a test sample and is identified as U.S. Ser. No. 08/035,341. The disclosure of said application is commonly assigned and incorporated herein by reference.

3. Technical Review

Chemiluminescent compounds that emit light with separated wavelength maxima and minimally overlapping but correctable emission spectra can be very useful in analytical assays, particularly in industrial assays, and in clinical diagnostic assays for multi-substance, e.g. multi-analyte, determinations. Such compounds can be used to tag or label binding partners, e.g. biological molecules, such as antigens, antibodies, and nucleic acids to form conjugates or tracers that are capable of producing mutually non-interfering, or minimally overlapping light emission signals or spectra, that allow the simultaneous detection and/or quantitation of multiple substances in a test sample. For example, simultaneous determinations of serum levels of luteinizing hormone (LH) and follicle stimulating hormone (FSH) from one patient sample is possible and is demonstrated below, because two chemiluminescent compounds having light emission spectra which span about 100-250 nm for a spectral region with signal intensity above 5% of peak height, but differing in their emission maxima so that the signals are discernable. In one example the emission maxim of two chemiluminescent signals differ by about 60 nm and preferably by 80 nm or more for labeling or tagging anti-LH and anti-FSH. A further example where simultaneous determinations is possible according to the methods described herein, is in the assay of amplified nucleic acid sequences, e.g. oncogenes associated with malignant transformation. See EP-A-0 481 704 (priority app. U.S. Ser. No. 598,269 (Oct. 16, 1990) and references cited therein) which is commonly assigned and incorporated herein by reference. In such assays, the inclusion of a parallel, internal reference material for a known, different target sequence in the same working vessel or reaction medium as a positive control is recognized as important to assay performance, for example, to safeguard false negative results. In other assay formats, the inclusion of a known control substance will also serve to assess assay performance.

The economical benefit and the experimental necessity of determining and/or quantitating two or more substances, e.g. analytes, in a test sample were the two main underlying motives in the development of a multiple-tracer assay system of the present invention. It was further envisioned that an ideal multiple-tracer system would emit multiple-wavelength signals under identical chemical conditions. It was recognized that it would be less desirable and more cumbersome to combine two chemiluminescent tracers in a multiple-analyte assay system that required two different sets of signal generating mechanisms, conditions and timings as would be in the case of utilizing two different classes of chemiluminescent compounds such as acridinium compounds pairing with luminol series or with stable dioxetanes, which involve the use of other chemicals or enzymes to generate the signal. Furthermore the two or more different chemiluminescent compounds or conjugates must have emission efficiency differing by not more than one order of magnitude.

A still further fundamental requirement was the adequate stability of the chemiluminescent compounds in aqueous media or environment, which will withstand the shipping conditions for commercial products when placed in kit form.

Applicant has achieved these goals by developing stable chemiluminescent analogues within the same general class that exhibit bathochromic shifts in their emission maxima, and emit light with comparable efficiency under identical chemical treatments.

Chemiluminescent acridinium compounds which are shown herein to emit blue light upon treatment with hydrogen peroxide and metal hydroxide have been well documented. U.S. Pat. Nos. 4,745,181, 4,918,192, 5,110,932, U.S. Ser. No. 07/826,186, U.S. Pat. No. 5,227,489, and U.S. Ser. No. 07/871,601, U.S. Pat. No. 5,241,070, describe stable polysubstituted-aryl acridinium esters; all of which are commonly assigned and incorporated herein by reference. Such acridinium compounds shall be referred to generally herein as "reference acridinium esters" or "acridinium esters". Such compounds as indicated include an acridinium ring system and, depending on the use of such compounds, further include an appropriate functional group(s), e.g. for attaching the label to a substance to form conjugates for use in a test assay, including the assays of the present invention.

Batmanghelich, et al, EP-A-0 478 626 (priority GB 2233450A (Jun. 24, 1989)), described the use of acridinium compounds of varying light emission, i.e. fast and slow durations to prepare different tracer conjugates, to achieve a "substantially simultaneous" quantitation of two or more different analytes. This approach, however, has several major drawbacks. First, one of the acridinium esters includes electron-withdrawing substituents on the phenolic moiety in order to achieve very short duration of light emission, i.e. complete emission or emission maxima in one second. This type of compound, e.g. a ortho-dihalogenated aryl acridinium ester, however, may suffer from lack of stability in aqueous environment. Second, light emission kinetics must be carefully examined to permit accurate correction in order to distinguish the light emission contributed individually by the two tracers during the overlapping period of light emission. The described method relies on the measurement of photons emitted in two separate time windows for sequential integration of light intensity. Unless the light emission overlap is relatively small, such correction could be a potential source for poor assay precision, particularly for detection of two analytes having widely different concentrations. The requirement for smaller light emission overlap would in turn demand the availability of a pair of chemiluminescent compounds, one having very short and the other very long duration of light emission; and would lead to compounds which either have stability problems or render the dual-analyte assay unpractical due to excessively prolonged signal-collection time.

Where the signal collection time is extended, an advantage of performing two assays in a single test sample would be lost. It is noted that in one automated analyzer using chemiluminescent detection and/or quantitation, a first test result is reported at fifteen (15) minutes and thereafter at every twenty (20) seconds during operation, see EP-A-0 502 638 (priority U.S. Ser. No. 665,196 (Mar. 4, 1991, abandoned)) which is commonly assigned and incorporated herein by reference.

Batmanghelich et al also described an acridinium compound of different light emission spectra to prepare different tracer conjugates. The approach they used was to extend the electronic conjugation of the acridinium nucleus to obtain 3-(4-carboxybutadienyl)-acridinium ester (compound 2b) with bathochromic shift of about 80 nm in the emission maximum as compared to the parent acridinium ester (compound 2a). Extension of electronic conjugation of the acridinium nucleus does not necessarily lead to major bathochromic shift in the emission maximum which is practically needed to construct a dual-analyte immunoassays and a possible reduction in emission efficiency. No teaching was made of benzacridinium chemiluminescent compounds or conjugates for use in such assays.

McCapra et al, EP-A-0 322 926 (priority U.S. Ser. Nos. 140,040 (Dec. 31, 1987), abandoned, and 291,843 (Dec. 29, 1988), abandoned), suggested the "chemiluminescent moiety" consisting of heterocyclic ring or ring system with ester, amide linkages attached to one of the carbon atoms on the ring or ring system. This chemiluminescent compound was said to include benz[a]acridinium, benz[b]acridinium, and benz[c]acridinium but the synthesis and structure of these compounds or conjugates was not described. Neither emission wavelength maxima, nor light emission efficiency of these structures were predicted; nor were the use of at least two chemiluminescent compounds or conjugates in an assay method, nor the utility of such compounds when used in assays based on their emission spectra.

The nomenclature of benz[a]acridinium and benz[b]acridinium utilized in this disclosure is based on Rule 21.5 of Definitive Rules for Nomenclature of Organic Chemistry, Ed. International Union of Pure and Applied Chemistry in the 1957 REPORT OF THE COMMISSION ON THE NOMENCLATURE OF ORGANIC CHEMISTRY.

According to the example given on Benz[a]anthracene, the compound arising from fusing benzene ring to the peripheral sides of the acridnium nucleus (structure below) should therefore be named according to whether side a, b, or c of the acridinium nucleus is fused with the benzene ring.

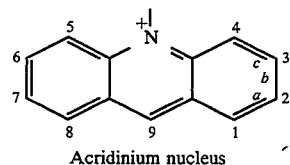

Acridinium nucleus

The following abbreviations are utilized in the disclosure:

1. ABAC: angular benz[a]acridinium compound
2. AFAC: aromatic ring fused acridinium compound
3. EtO: ethoxy
4. DMAE: dimethyl acridinium ester
5. DIPAE: diisopropyl acridinium ester
6. LBAC: linear benz[b]acridinium compound
7. LEAC: longer emission acridinium compound
8. LEAE: longer emission acridinium ester
9. MeO: methoxy
10. NSE: N-sulfoethyl
11. NSP: N-sulfopropyl
12. PCT: percent cross talk
13. PMP: paramagnetic part icles
14. QAE: quaternary ammonium ethoxy
15. RLU: relative light units

SUMMARY OF THE INVENTION

A method is described for detection and/or quantitation of at least two substances in a test sample comprising simultaneously detecting the emission signals of at least two chemiluminescent conjugates; each chemiluminescent conjugate being associated with a substance sought to be detected and/or quantitated in the test sample. The emission signals of each of the chemiluminescent conjugates are discernable by their spectral emissions, so that the substances may be detected and/or quantitated.

A chemiluminescent compound for use in the assays of the present invention is described in the formula:

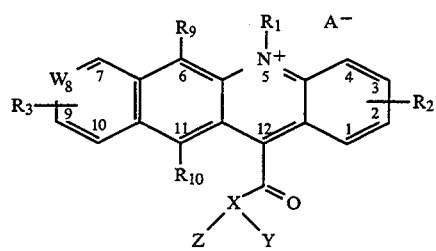

where W is carbon; alternatively, $C_7$, W, $C_9$ or $C_{10}$ can be replaced with —N=; or W can be omitted and $C_7$ connected to $C_9$, and $C_7$, $C_9$ or $C_{10}$ can be replaced with —O—, —S—, —NH— or —NR—; Y is a branched or straight chained alkyl containing optionally up to 20 carbon atoms, halogenated or unhalogenated, or a polysubstituted aryl moiety of the formula:

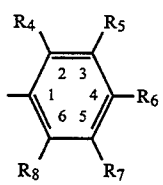

$R_1$ is an alkyl, alkenyl, alkynyl or aralkyl containing optionally up to 20 heteroatoms;

$R_2$, $R_3$, $R_9$ and $R_{10}$ are identical or different groups selected from hydrogen, substituted or unsubstituted aryl (ArR or Ar), halide, amino, hydroxyl, nitro, sulfonate, —R, —CN, —COOH, —SCN, —OR, —SR, —SSR, —C(O)R, —C(O)OR, —C(O)NHR, or —NHC(O)R;

$R_2$ includes a single or multiple substituent at $C_{1-4}$;

$R_2$ can also be a fused aromatic ring with or without heteroatoms;

$R_3$ includes a single or multiple substituent at $C_7$, W, $C_9$ or $C_{10}$;

A— is a counter ion including $CH_3SO_4^-$, $FSO_3^-$, $CF_3SO_4^-$, $C_4F_9SO_3^-$, $CH_3C_6H_4SO_3^-$ and halide;

X is a heteroatom including nitrogen, oxygen or sulfur, such that when X is oxygen or sulfur Z is omitted, when X is nitrogen then Z is —$SO_2$—Y′ and Y′ is equal to Y and where the substituents to Y and Y′ do not have to be the same;

$R_4$ and $R_8$ are alkyl, alkenyl, alkynyl, alkoxyl, alkylthiol, amido, $R_5$ and $R_7$ are any of $R_3$, $R_9$ and $R_{10}$ defined above;

$R_6$=—$R_{11}$—$R_{12}$, where $R_{11}$ is not required but optionally can be branched or straight-chained alkyl, substituted or unsubstituted aryl or aralkyl containing optionally up to 20 heteroatoms, and $R_{12}$ is a leaving group or an electrophilic functional group attached with a leaving group or —Q—R—Nu, —Q—R(I)$_n$Nu, —Q—Nu, —R—Nu or —Nu, n is a number of at least 1, Nu is a nucleophilic group, Q is a functional linkage, I is an ionic or ionizable group;

$R_5$ and $R_6$, and $R_6$ and $R_7$ are interchangeable; and

R is alkyl, alkenyl, alkynyl, aryl or aralkyl containing optionally up to 20 heteroatoms.

A chemiluminescent compound or conjugate is characterized in that upon chemical treatment the compound or conjugate emits a blue-green, green, yellow, orange and red-orange light having a discernable emission spectra peak or maximum. In one embodiment, i.e. compound, the emission maxima is greater than or equal to 480 nm and in a preferred embodiment greater than or equal to 515 nm.

An amplification method is described for target sequences, including one or more nucleic acid sequences, in a test sample comprising providing a test sample suspected of containing one or more target sequences, adding an internal reference to said test sample, amplifying the target sequences, providing at least two chemiluminescent conjugates, each chemiluminescent conjugate being associated with target sequences and the internal reference, and simultaneously detecting and/or quantitating amplified target sequences and the internal reference by emissions of the chemiluminescent conjugates.

Accordingly, it is a primary object of the invention to provide a method for the simultaneous detection and/or quantitation of at least two substances in a test sample by use of at least two different chemiluminescent compounds or conjugates each having discernable emission spectra.

Another object of the invention is to provide an assay method for the simultaneous detection and/or quantitation of an analyte and an internal standard or control in a single test medium or transfer tube.

Still another object of the invention is to increase the efficiency of automated analyzers by providing for the simultaneous performance of two assays on a test sample in a single reaction medium or transfer tube.

A further object of the invention is to provide methods for synthesis of chemiluminescent compounds and intermediate products which may be used to synthesize such chemiluminescent compounds.

An object of the invention is to provide chemiluminescent, aromatic ring-fused acridinium compounds (AFAC) that emit green or yellow light.

Another object of the invention is to provide chemiluminescent, aromatic ring-fused acridinium compounds (AFAC) that emit green or yellow light with wavelength maxima or peaks greater than or equal to 515 nm.

Still another object of the invention is to provide a simultaneous dual chemiluminescent label assay.

A further object of the invention is to provide hydrophilic AFAC which carries one or more ionic and/or ionizable groups with or without, additionally, the reactive functional groups useful for forming covalent linkage with other micro- or macromolecules or encapsulation inside liposomes.

An object of this invention is to provide AFAC conjugates formed between AFAC directly or indirectly with binding partners, e.g. biological molecules.

Another object of this invention is to provide test assays involving the use of acridinium ester and AFAC conjugates.

Still another object of the invention is to provide multianalyte assays in which the determination of two or more analytes or substances or combination thereof present in the sample as a mixture, can be carried out simultaneously in the same reaction medium or transfer tube due to the mutually non-interfering, or minimally overlapping but correctable light signals produced by the same chemical treatments of two or more different chemiluminescent tracers or compounds.

A further object of the present invention is to provide test kits for performing dual chemiluminescent label test assays.

An object of the present invention is to provide test kits having two or more chemiluminescent reagents for simultaneously assaying at least two substances in a test sample.

Another object of the invention is to provide intermediate compounds to be utilized in the synthesis of labels for use in analytical assays.

Still another object of the present invention is to provide chemiluminescent compounds having light emission spectra which span about 100–250 nm, for a spectral region with signal intensity above 5% of peak height.

These and other objects in view, as will be apparent to those skilled in the art, the invention resides in the combination of elements set forth in the specification and covered by the claims appended hereto.

BRIEF DESCRIPTION OF DRAWINGS

The foregoing and other objects and advantages of the invention will be appreciated more fully from the following further description thereof with reference to the accompanying drawings wherein

FIGS. 2A–2E illustrate emission spectra of acridinium esters and ABAC of the present invention is an emission spectrum of DMAE-Bz (50 μg in 0.5 ml of acetonitrile); FIG. 2B is an emission spectrum of 3-MeO-DMAE-Bz (50 μg in 0.5 ml of acetonitrile) peak≈422 nm; FIG. 2C is an emission spectrum of DIPAE-Bz (20 μg in 0.5 ml in acetonitrile) peak≈428 nm; FIG. 2D is an emission spectrum for 3-QAE-DMAE-NHS (40 μg in 0.5 ml of acetonitrile) peak≈426 nm; and FIG. 2E is an emission spectrum of angular benz[a]acridinium ester (2 mg in 0.2 ml of DMF) peak≈440 nm.

FIGS. 3A–3J illustrate emission spectra of LBAC of the present invention as follows: FIG. 3A FIG. 3A is an emission spectrum of LEAE-Bz (50 μg in 0.5 ml of acetonitrile) peak≈520 nm; FIG. 3B is an emission spectrum of DIP-LEAE-Bz (50 μg in 0.5 ml of acetonitrile) peak≈520 nm; FIG. 3C is an emission spectrum of 3-EtO-LEAE-Bz (50 μg in 0.5 ml of acetonitrile) peak≈508 nm; FIG. 3D is an emission spectrum of 3-QAE-LEAE-Bz (100 μg in 0.5 ml of acetonitrile) peak≈544 nm; FIG. 3E is an emission spectrum of 2-MeO-LEAE-Bz (30 μg in 0.5 ml of acetonitrile) peak≈550 nm; FIG. 3F is an emission spectrum of LEAC-Bz (50 μg in 0.5 ml of acetonitrile) peak≈520 nm; FIG. 3G is an emission spectrum of 2-QAE-LEAE-NHS (70 μg in 0.5 ml of acetonitrile) peak≈550 nm; FIG. 3H is an emission spectrum of NSP-LEAE-Bz (15 μg in 0.5 ml of acetonitrile) peak≈516 nm; FIG. 3I is an emission spectrum of 2-MeO-NSE-LEAE-NHS (50 μg in 0.5 ml of acetonitrile) peak≈546 nm; and FIG. 3J is an emission spectrum of 2-MeO-LEAE-Imidate (100 μg in 0.5 ml of acetonitrile) peak≈550 nm.

FIGS. 4A–4D illustrate emission spectra of mixed acridinium esters and LBAC of the present invention FIG. 4A is an emission spectrum of mixed DMAE-Bz (10 μg) and LEAE-Bz (50 μg in 0.5 ml of acetonitrile); FIG. 4B is an emission spectrum of mixed DMAE-Bz (100 μg) and 2-MeO-LEAE-Bz (25 μg in 0.5 ml of acetonitrile); FIG. 4C is an emission spectrum of mixed 3-MeO-DMAE-Bz (50 μg) and 2-MeO-LEAE-Bz (30 μg in 0.5 ml of acetonitrile); and FIG. 4D is an emission spectrum of mixed 3-MeO-DMAE-Bz (5 μg) and 2-QAE-LEAE-NHS (105 μg in 0.5 ml of acetonitrile).

FIG. 5A is a transmittance curve of a BG-38 optical filter; FIG. 5B is a transmittance curve of a corion P70-450 optical filter; FIG. 5C is a transmittance curve of a corion LL500 optical filter; FIG. 5D is a transmittance curve of a corion laminated CS550/CS600 optical filter; and FIG. 5E is a transmittance curve of a corion LL520 optical filter.

FIG. 7 illustrates the area of overlap between the transmittance curve of an optical filter (Corion P70-450) and the emission spectra of LEAE-Bz.

FIG. 8 illustrates FSH standard curve assays read on a dual PMT luminometer.

FIG. 9 illustrates LH standard curve assays read on a dual PMT luminometer.

DESCRIPTION OF PREFERRED EMBODIMENT

Figure 1G:
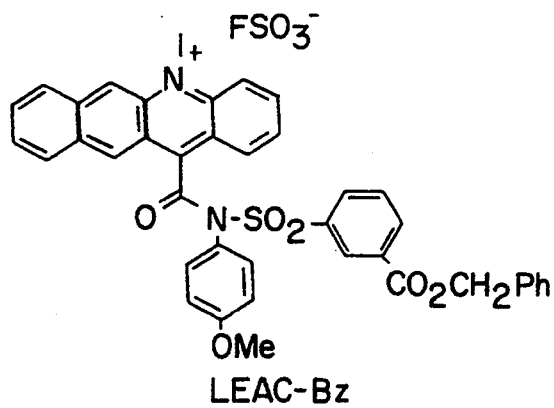
FIGS. 1A–1N illustrate the structures of representative acridinium esters, ABAC, and LBAC's of the present invention.
Figure 1H:
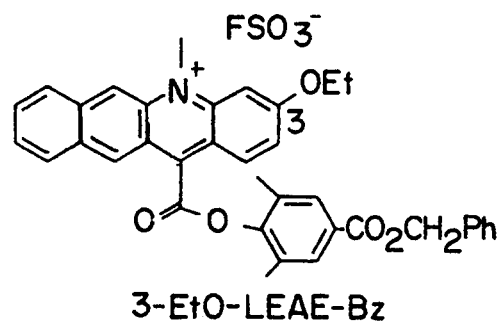
Figure 1I:
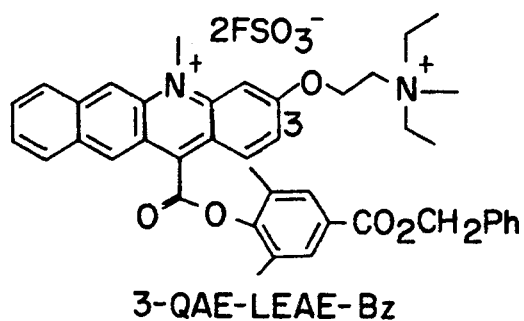
Figure 1J:
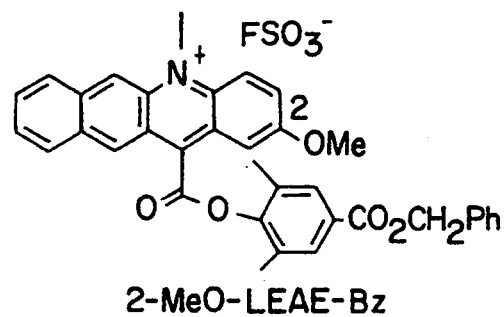
Figure 1K:
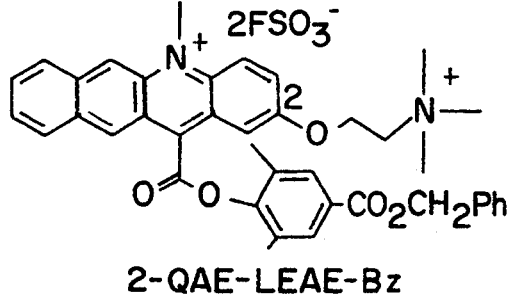
Figure 1L:
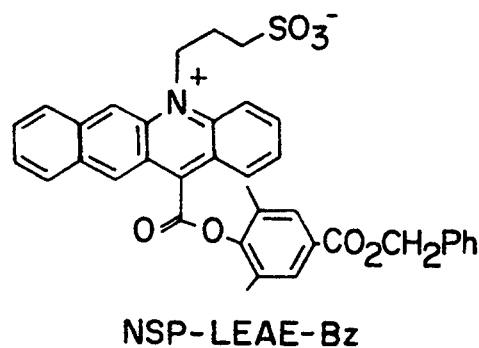
Figure 2A:
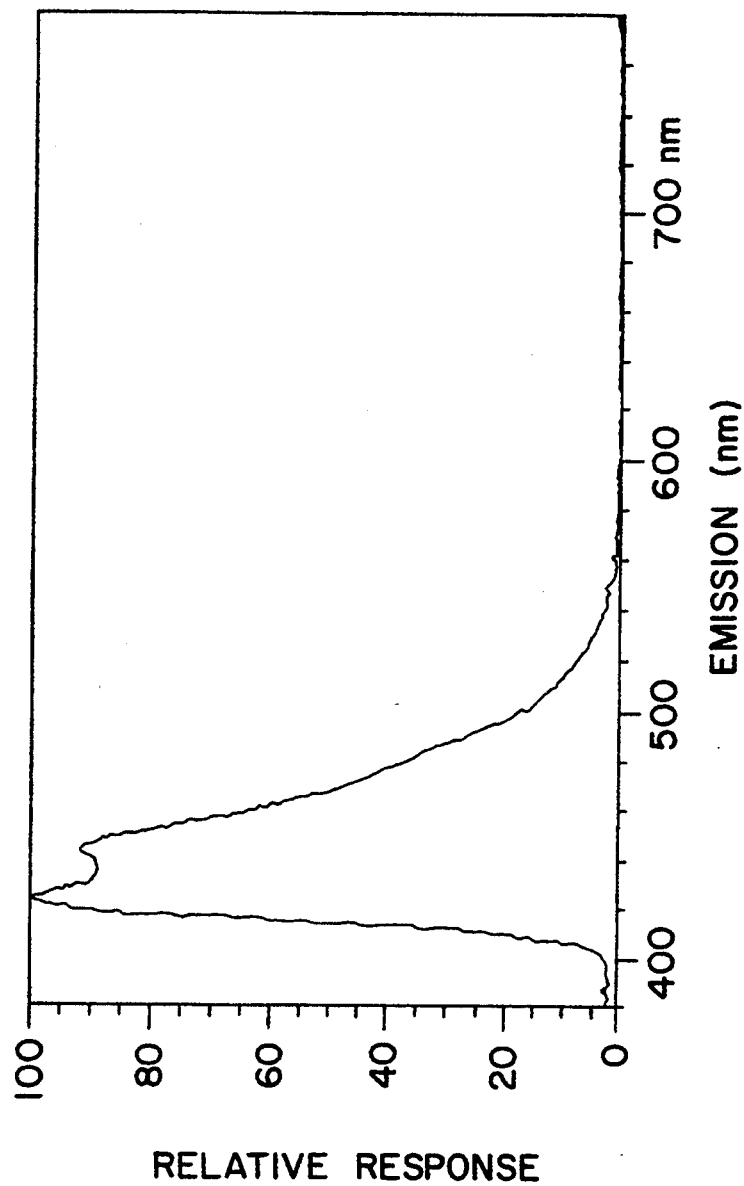
Figure 2C:
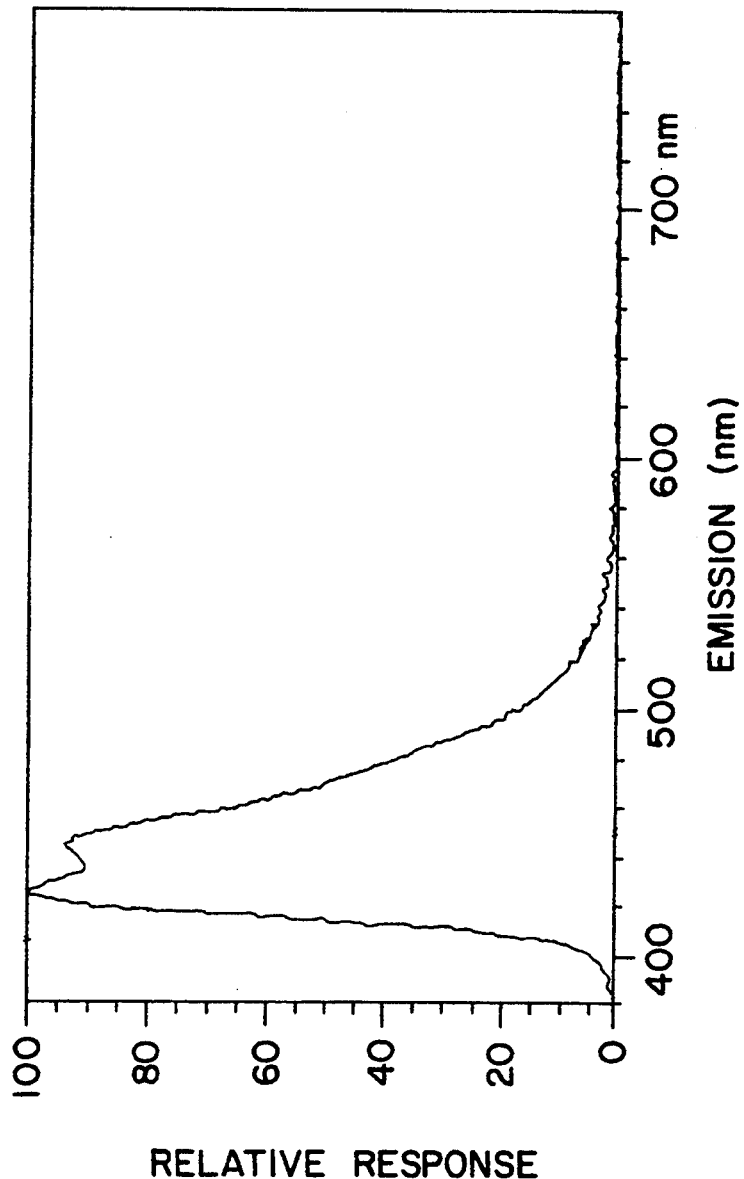
Figure 2D:
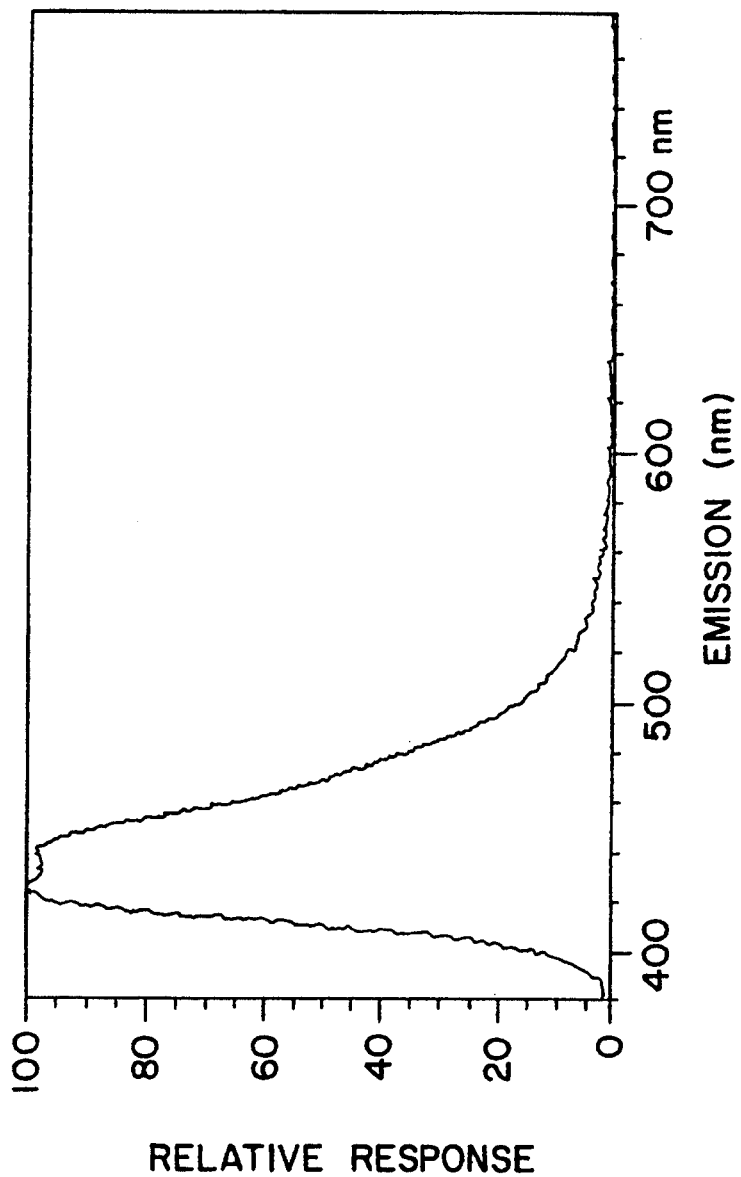
Figure 3A:
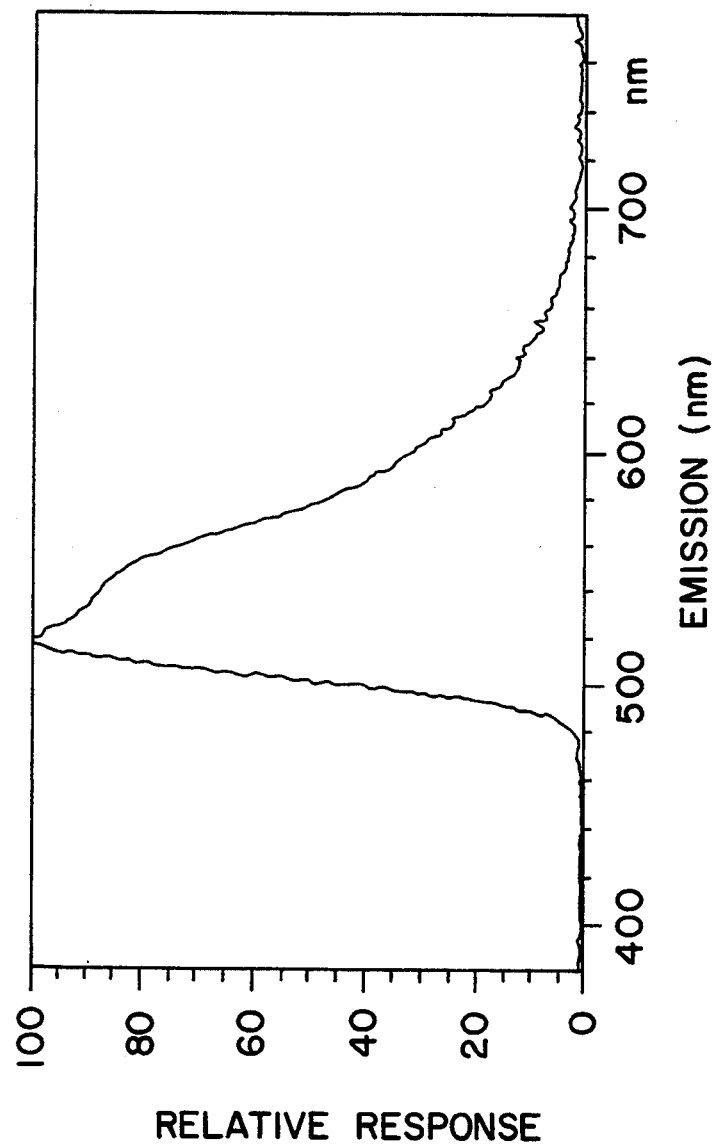
Figure 3B:
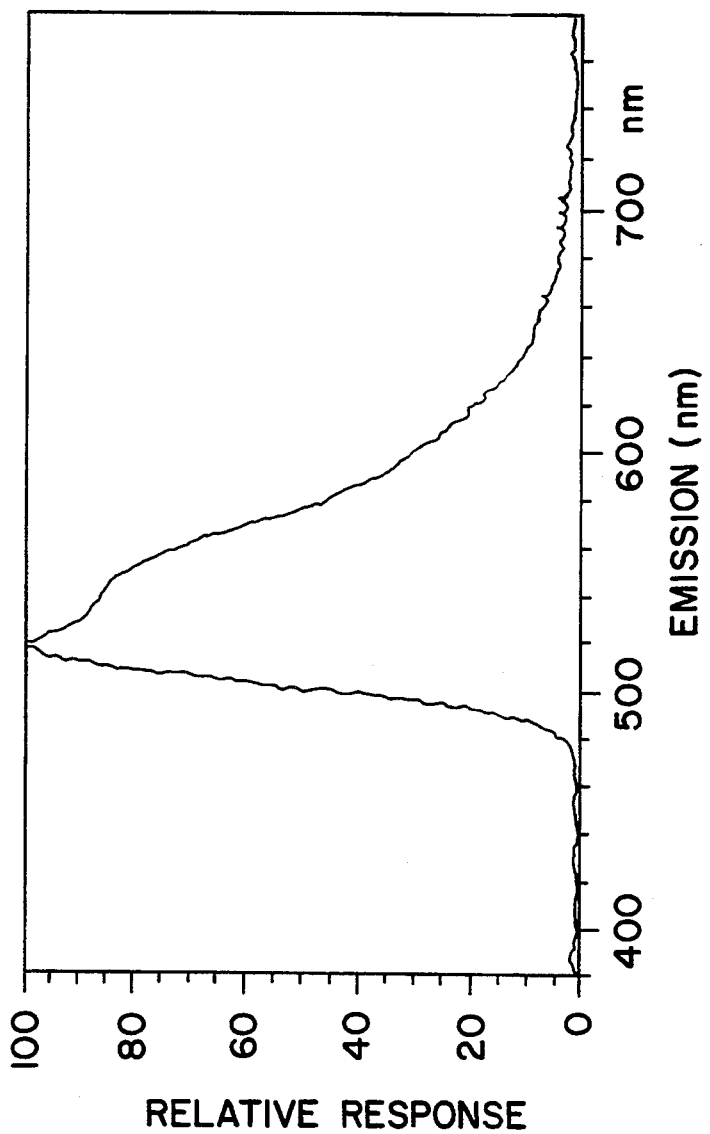
Figure 3D:
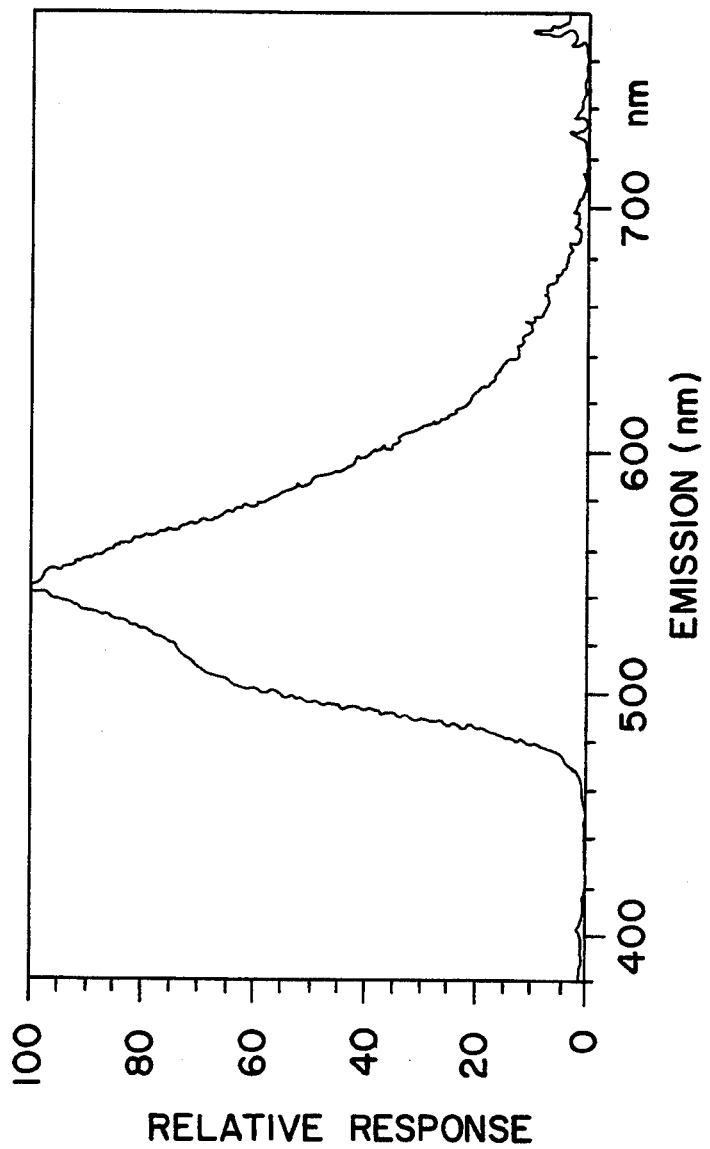
Figure 3E:
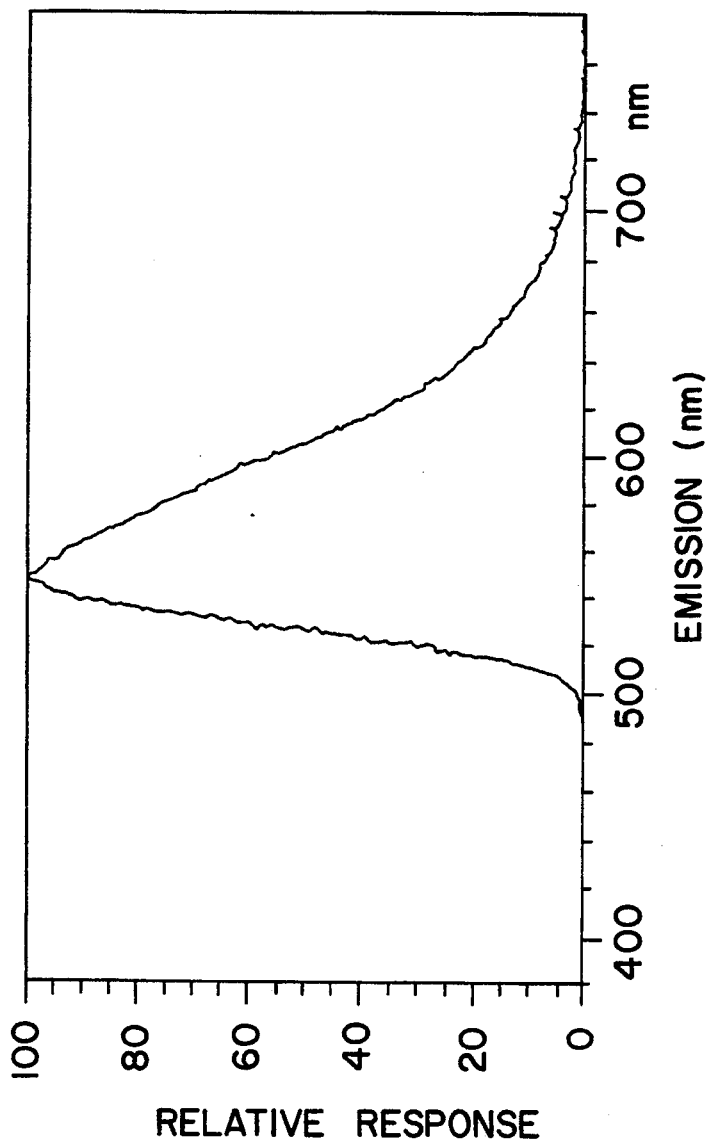
Figure 3F:
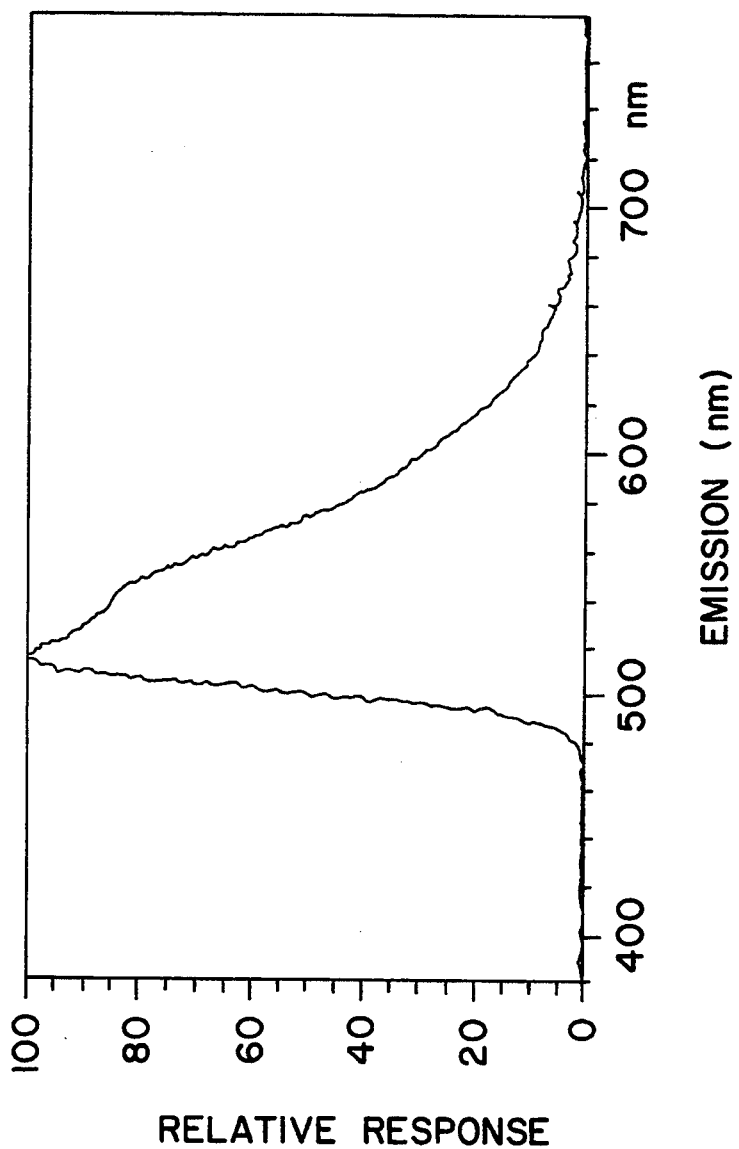
Figure 3G:
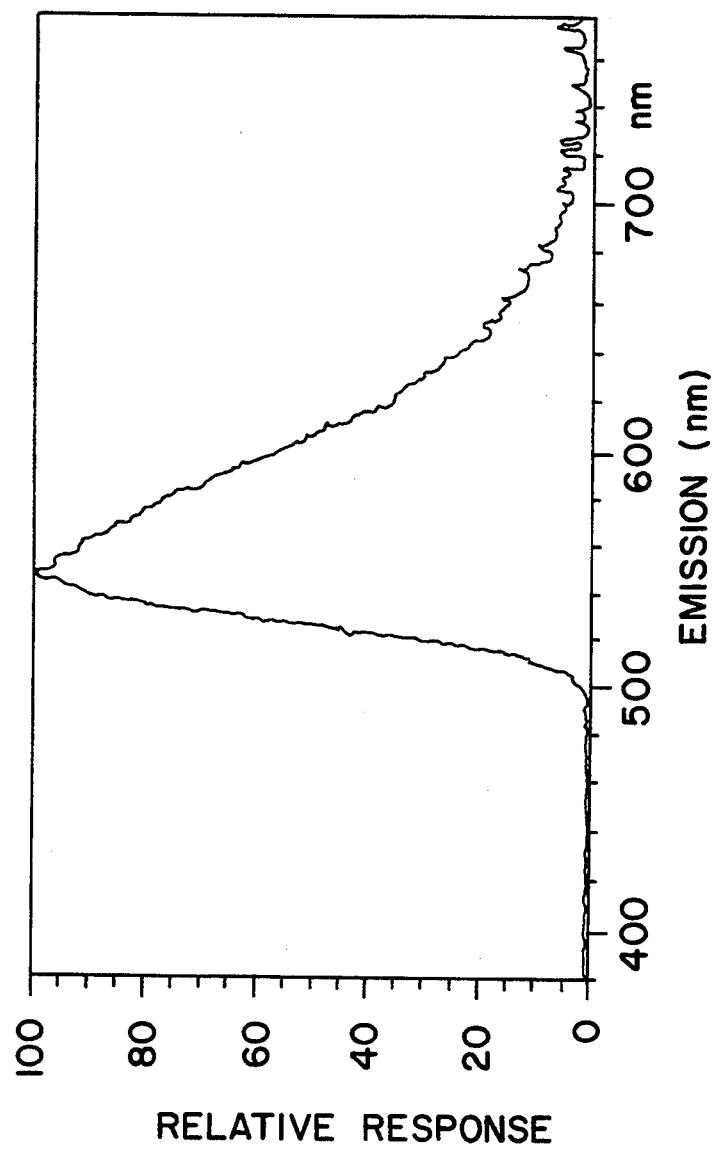
Figure 3H:
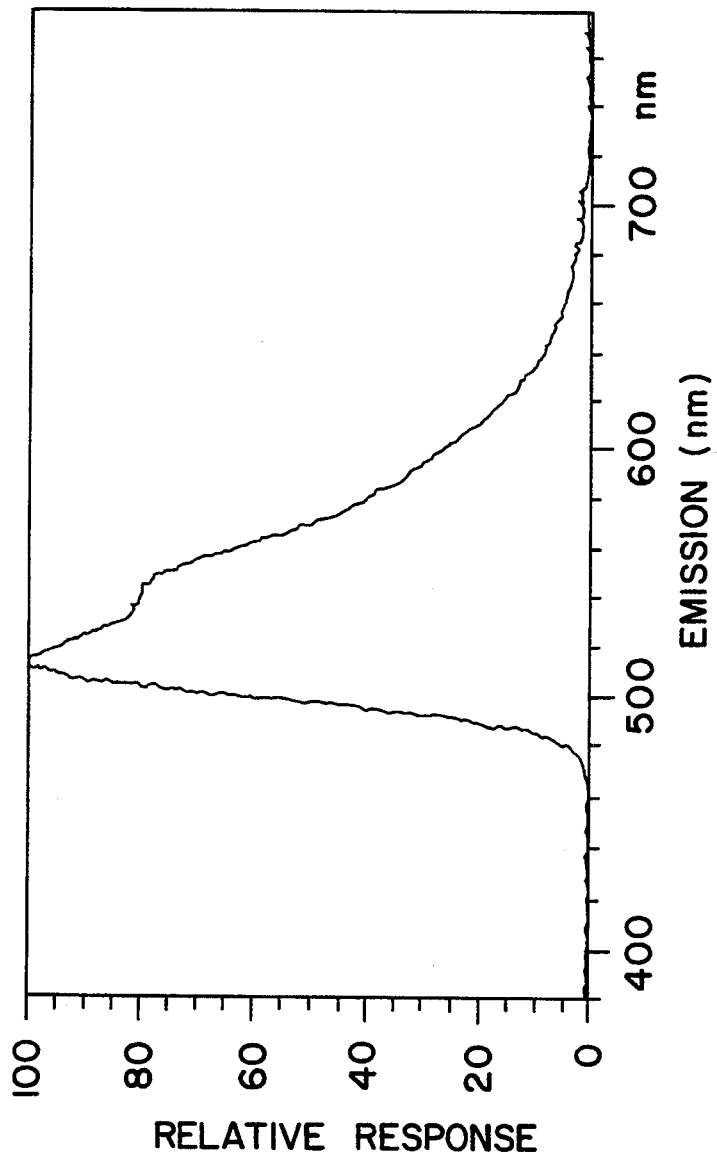
Figure 3I:
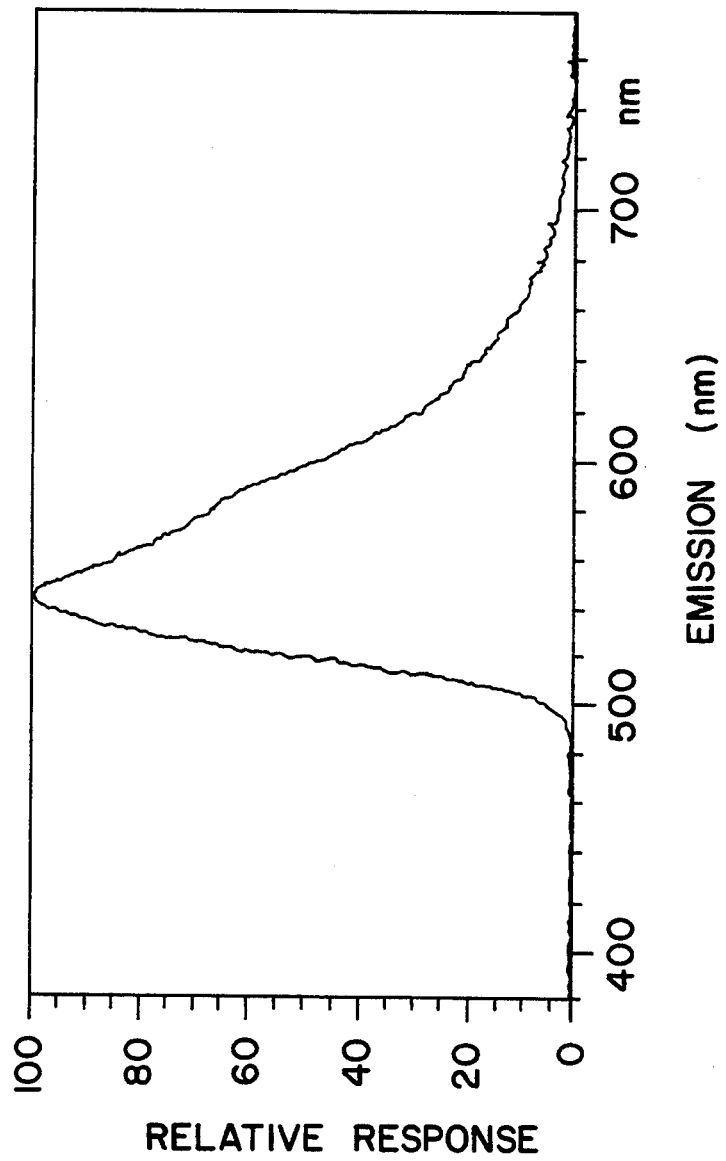
Figure 3J:
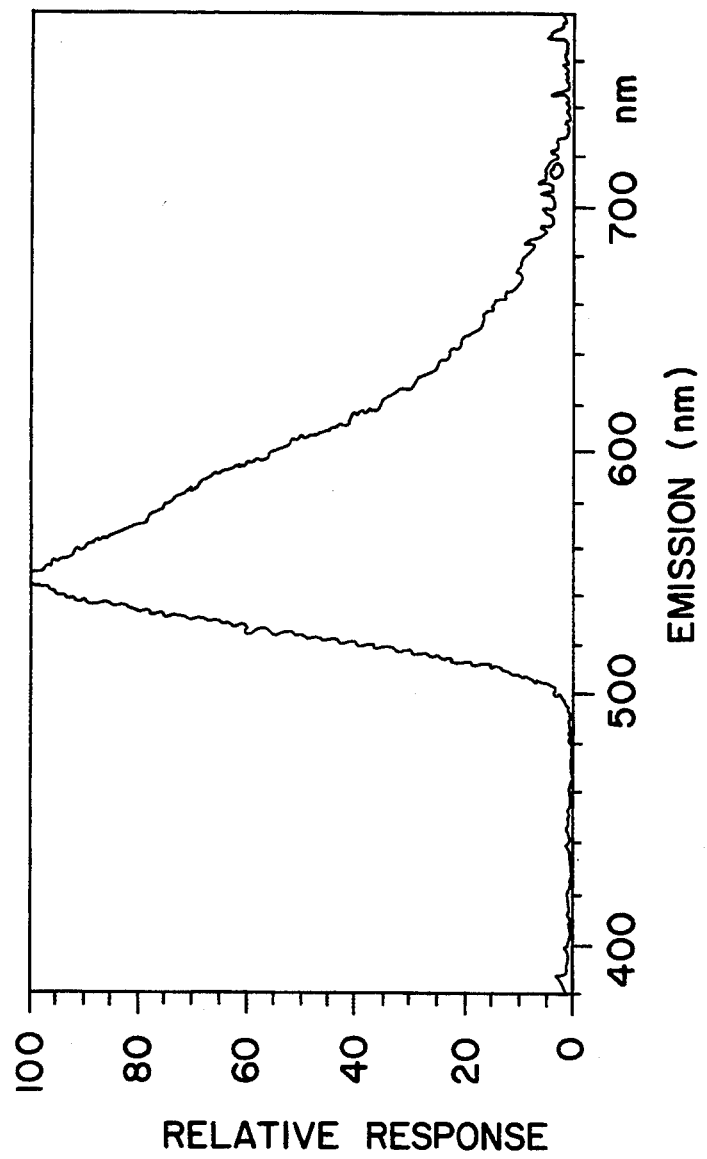
Figure 4B:
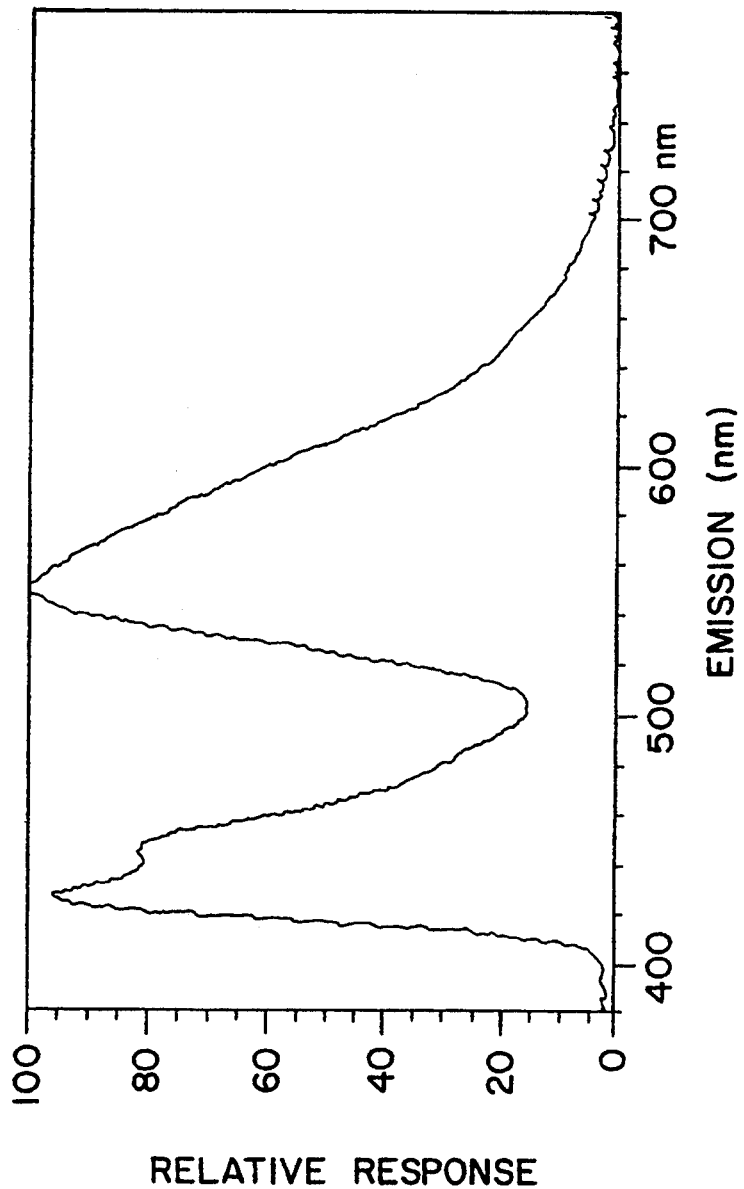
Figure 4C:
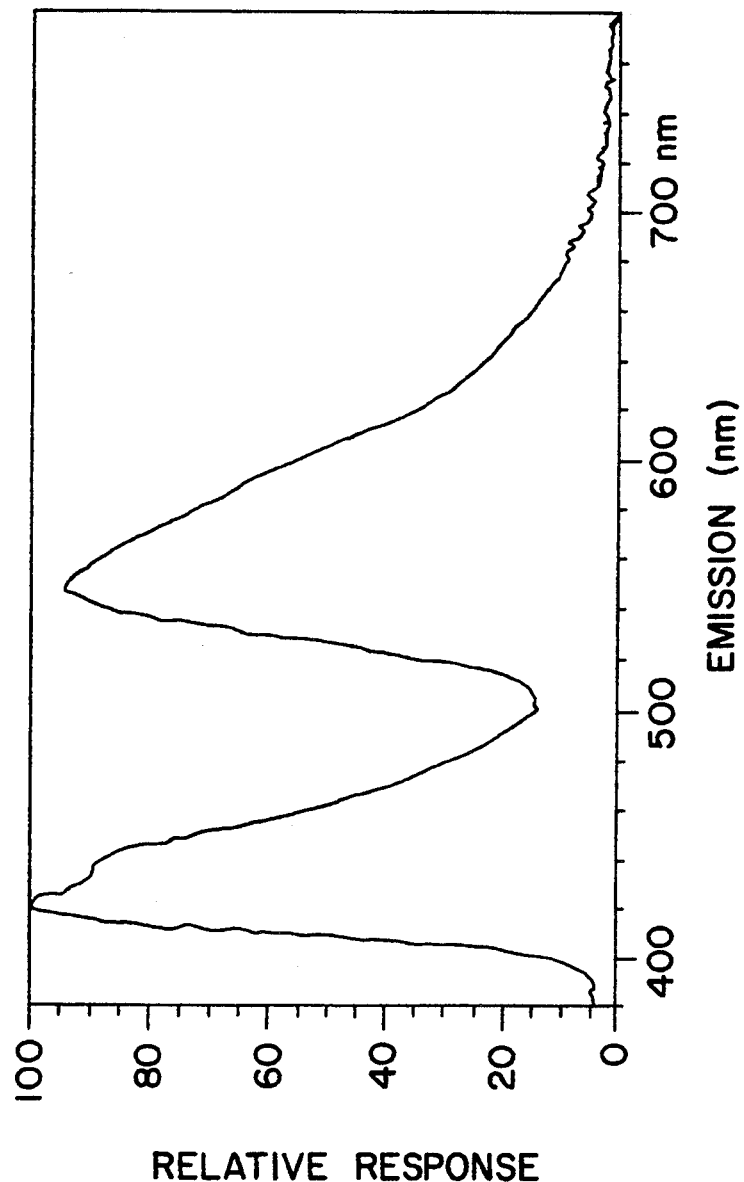
Figure 4D:
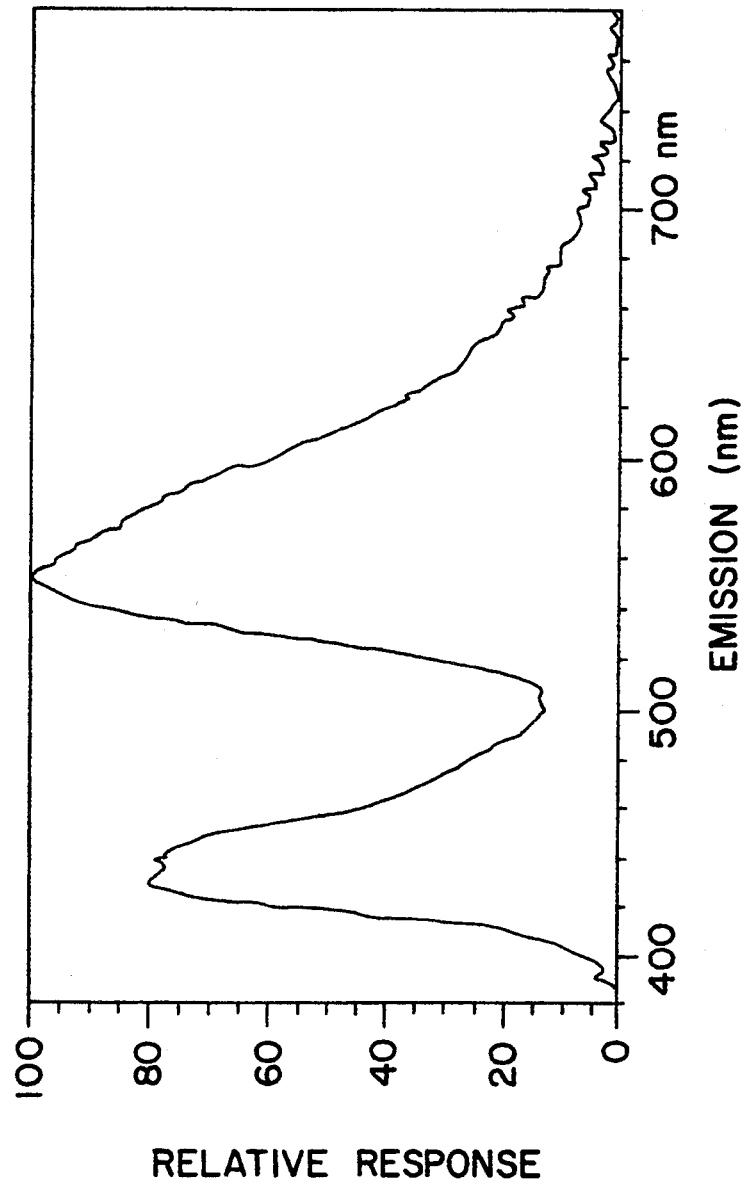
Figure 5A:
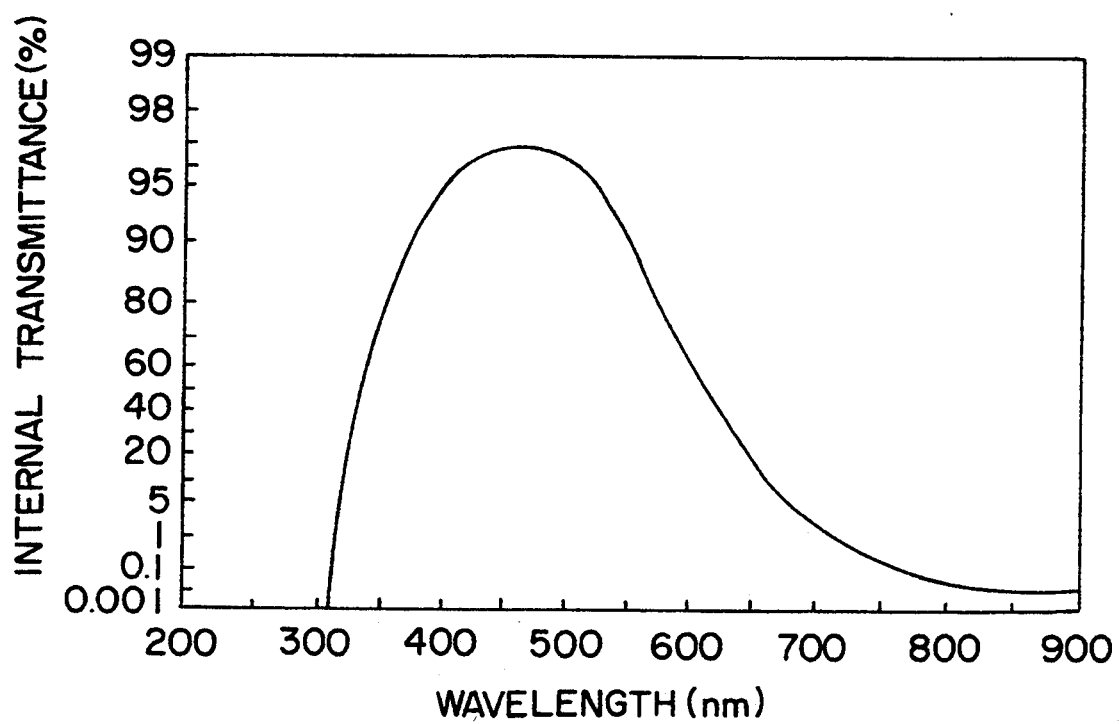
FIGS. 5A–5E illustrate transmittance curves of various optical filters
Figure 5B:
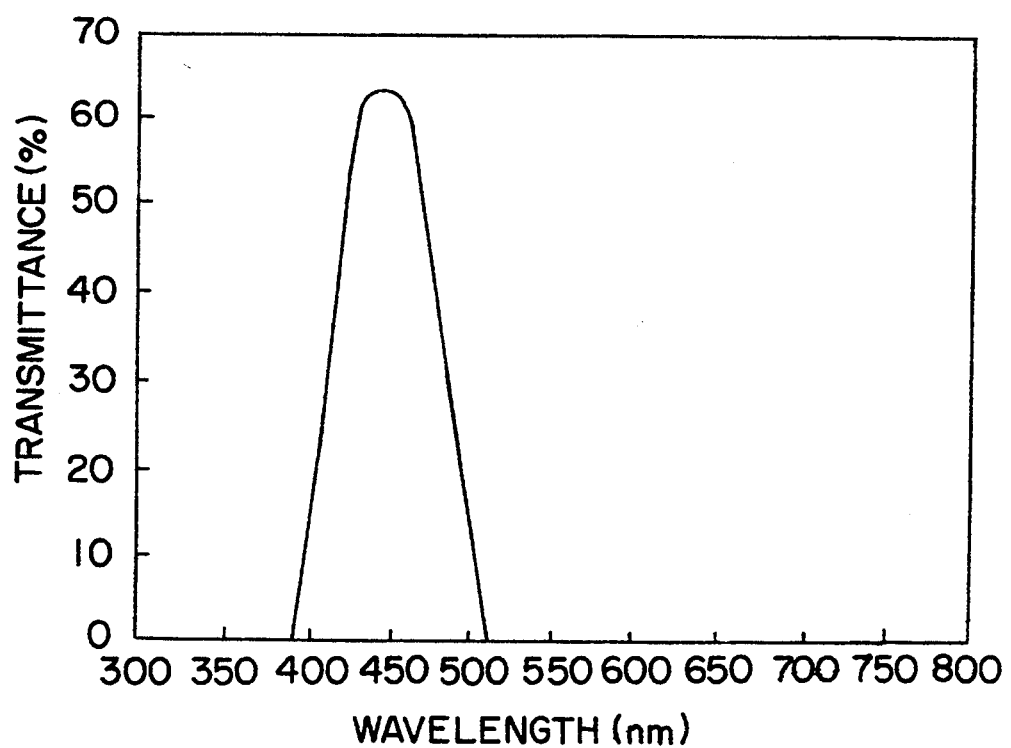
Figure 5C:
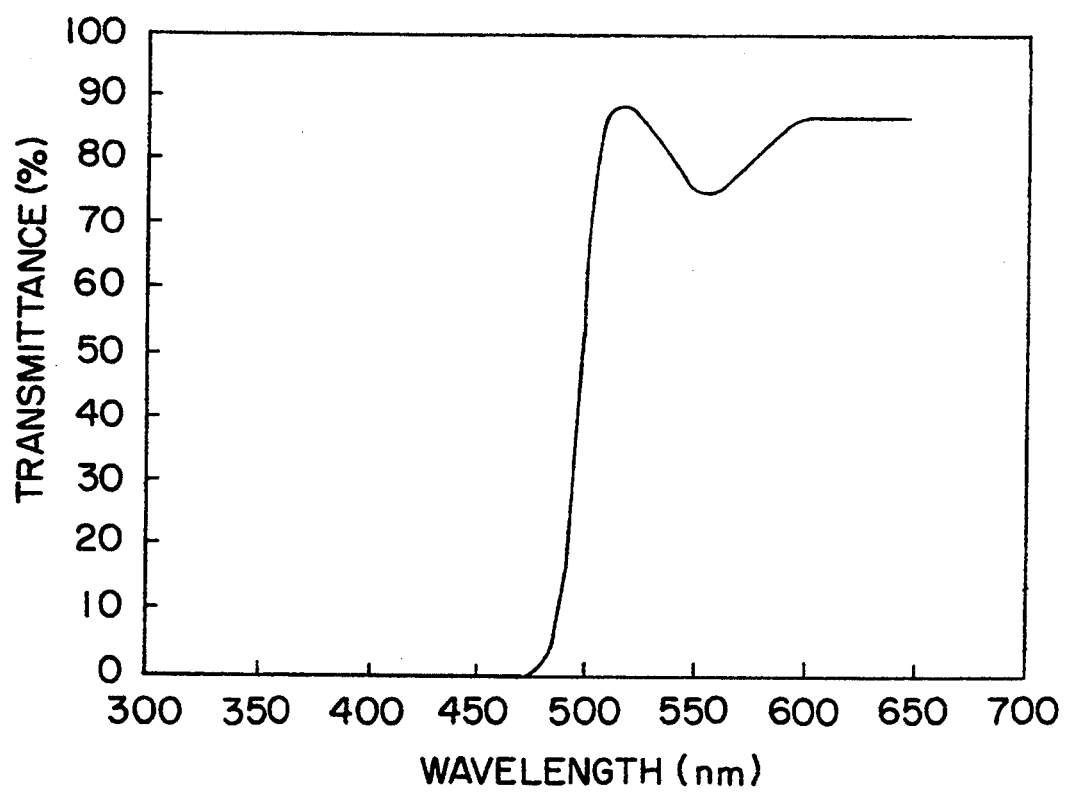
Figure 5D:
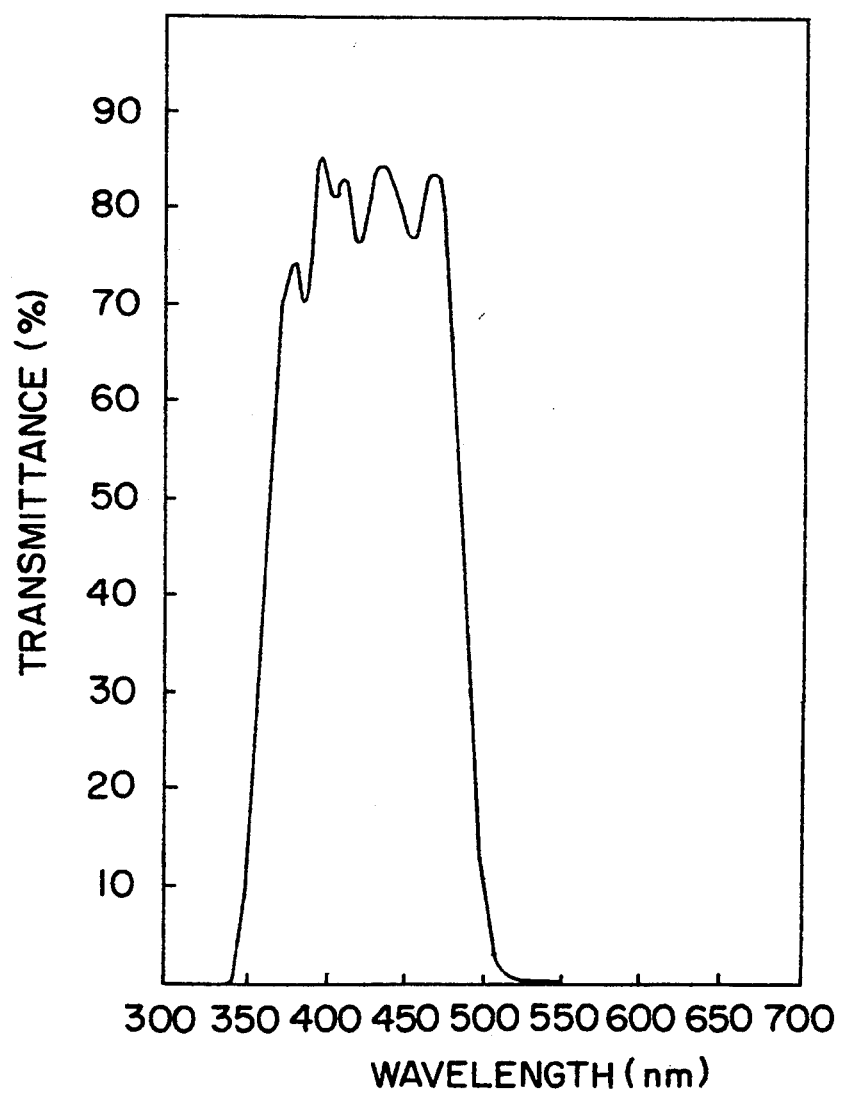
Figure 5E:
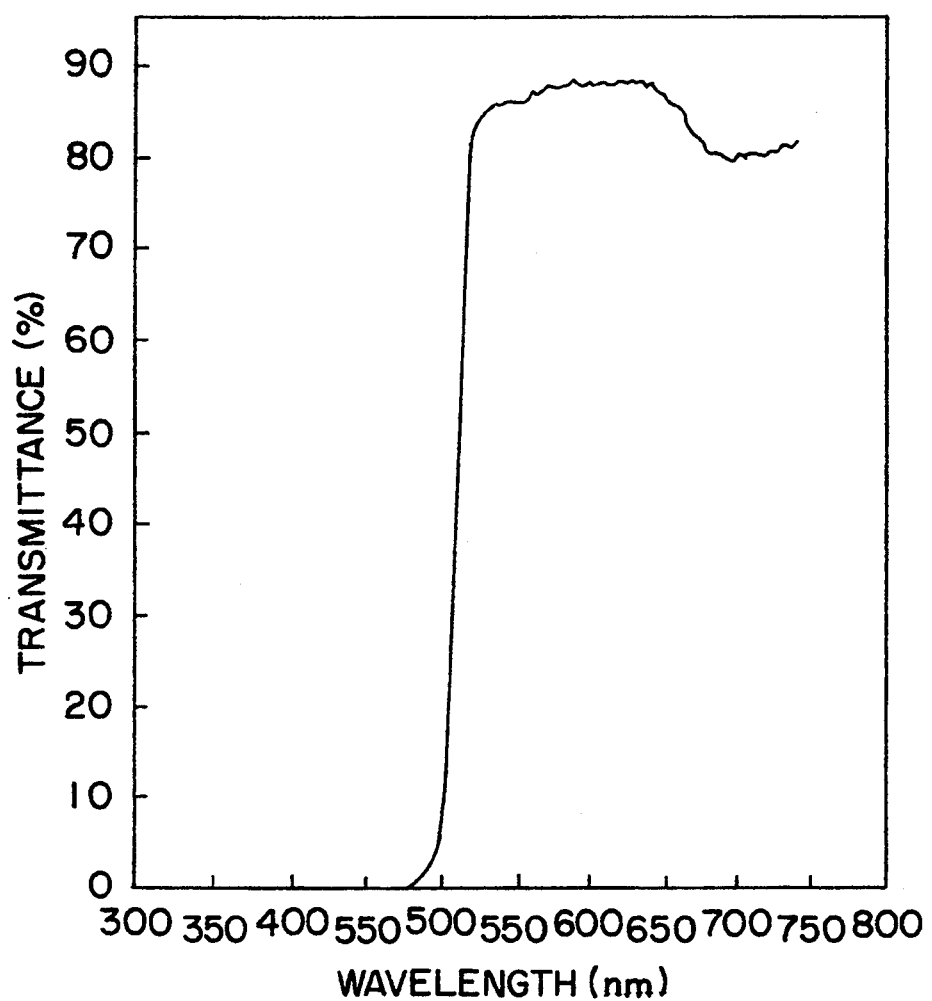

The AFAC of present invention comprise linear benz[b]acridinium (LBAC), furanoacridinium, thiophenoacridinium, pyrroacridinium compounds and pyridoacridinium compounds. By virtue of the specific position of the aromatic ring fused to the acridinium nucleus LBAC was unexpectedly found to generate a chemiluminescent emission signal with much greater bathochromic shift than the angular benz[a]acridinium compounds (ABAC), and to the corresponding "reference acridinium esters", i.e. DMAE-Bz, DIPAE-Bz and 3-MeO-DMAE-Bz, see FIG. 1.

The general structure of AFAC is represented by Formula I:

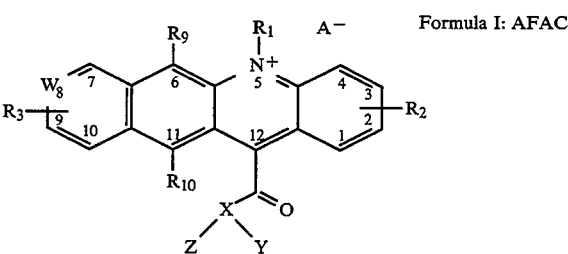

Formula I: AFAC

The general structures of linear benz[b]acridinium compounds and the isomeric, furano-, thiopheno-, pyrro- and pyrido- acridinium compounds are shown by the Formulas II, IIIA–III C, and IV A–IV D respectively.

Formula II: LBAC

Formula III A

-continued

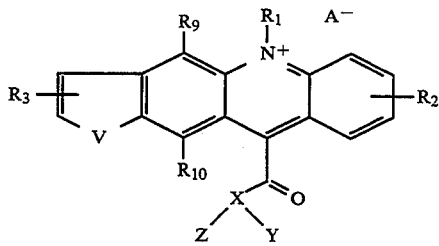

Formula III B

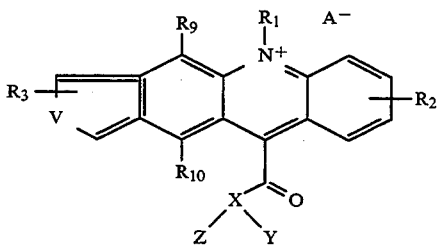

Formula III C
Furanoacridinium compounds: V = O,
Thiophenoacridinium compounds: V = S and
Pyrroacridinium compounds: V = NH or NR.

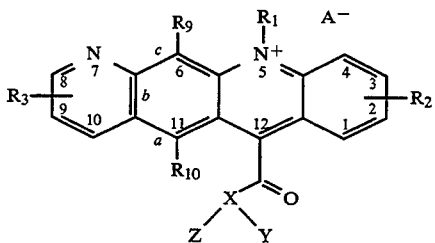

Formula IV A: Pyrido[5,6-b]acridinium compounds

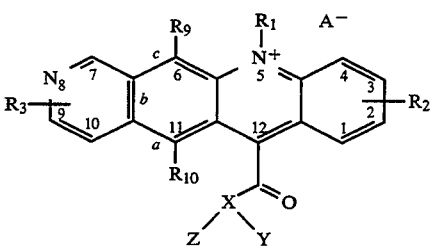

Formula IV B: Pyrido[4,5-b]acridinium compounds

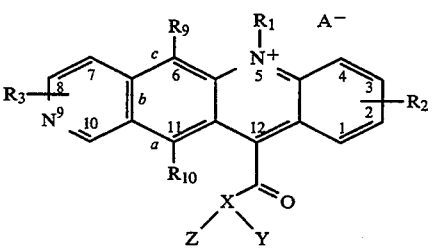

Formula IV C: Pyrido[3,4-b]acridinium compounds

-continued

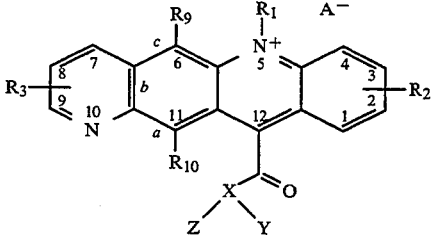

Formula IV D: Pyrido[2,3-b]acridinium compounds

One subclass of the AFAC contains reactive functional group(s), in addition to the fundamental chemiluminescent compound with properties described above, to enable formation, i.e., by covalent linkage, with binding partners, and particularly with biological molecules, to produce conjugates useful as non-isotopic tracers in binding assays or as a key integral part of a multianalyte assay system. Another subclass of the AFAC contains one or more ionic and/or ionizable groups which enhance the solubility of the compounds in aqueous media and/or allow them to be encapsulated inside liposomes with low leakage. Such hydrophilic LBAC can also be modified to carry additional reactive functional groups to allow forming conjugates with other micro or macromolecules.

Preferred LBAC, Furanoacridinium compounds, Thiophenoacridinium compounds, Pyrroacridinium compounds and Pyridoacridinium compounds having the above-mentioned characteristics and being suitable for above-described utilities include chemiluminescent compounds represented by the above Formulas I, II, IIIA–III C, and IV A–IV D respectively, where:

W is a carbon, Formula I becomes the LBAC class of chemiluminescent compounds as represented by Formula II; or W can be omitted and C7 connected to C9 and one of C7, C9 or C10 can be replaced with —O—, —S—, —NH—, or —NR— to form a 5-membered aromatic ring fused linearly to the acridinium nucleus as shown in Formula III A-C; or C7, W, C9, or C10 can be replaced with —N= to form a 6-membered pyrido ring fused linearly to the acridinium nucleus as shown in Formula IV A-D;

$R_1$ is an alkyl, alkenyl, alkynyl, or aralkyl containing optionally up to 20 heteroatoms, preferably nitrogen, oxygen, halogen, phosphorus or sulfur.

$R_2$, $R_3$, $R_9$ and $R_{10}$ are identical or different groups selected from hydrogen, substituted or unsubstituted aryl (ArR or Ar), halide, amino, hydroxyl, nitro, sulfonate, —R, —CN, —CO$_2$H, —SCN, —OR, —SR, —SSR, —C(O)R, —C(O)OR, —C(O)NHR, or —NHC(O)R.

R is alkyl, alkenyl, alkynyl, aryl, or aralkyl, containing optionally up to 20 heteroatoms.

$R_2$ includes a single or multiple substituents) at C$_{1-4}$.
$R_3$ includes a single or multiple substituent(s) at C$_7$, W, C$_9$ or C$_{10}$.

$R_2$ can be also a fused aromatic ring with or without heteroatoms.

A— is a counter ion including CH$_3$SO$_4$—, FSO$_3$—, CF$_3$SO$_4$—, C$_4$F$_9$SO$_3$—, CH$_3$C$_6$H$_4$SO$_3$—, and halide.

X is a heteroatom including nitrogen, oxygen, or sulfur, when X is oxygen or sulfur Z is omitted, when X is nitrogen then Z is —SO$_2$—Y′.

Y is a branched or straight chained alkyl containing optionally up to 20 carbon atoms, halogenated or unhalogenated, or a polysubstituted aryl moiety of Formula V:

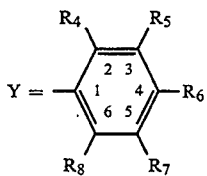

Formula V
Polysubstituted Aryl Moiety

Y' is equal to Y, and the substituents to Y and Y' do not have to be the same.

$R_4$, and $R_8$ are alkyl, alkenyl, alkynyl, alkoxyl, alkylthio, amido, groups positioned to ensure better stability of AFAC in aqueous media or environment. The stability of AFAC rendering them suitable for commercialization is attributed to the steric effect, electronic effect, or a combination thereof resulting from the presence of these two groups. $R_5$ and $R_7$ are as recited for $R_3$, $R_9$, and $R_{10}$ in Formula I. For conjugating AFAC to biological molecules, $R_6$ can be a leaving group or an electrophilic functional group attached with a leaving group, or functional groups which can be readily converted into such reactive groups, directly attached or connected via a spacer to the ring. A "spacer" is defined as branched or straight-chained alkyl, substituted or unsubstituted aryl or aralkyl, optionally containing up to 0-20 heteroatams. Examples of such functional groups include:

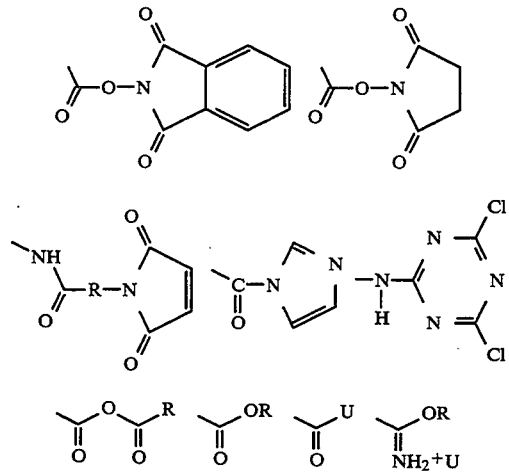

—N=C=S, —N=C=O, —N₂+U—, —N₃, —COOH, —U, or —SO₂U, where U is a halide.

Alternatively, $R_6$ can be a protected or unprotected nucleophilic functional group directly attached or connected via a spacer to Y. Thus $R_6$=—Q—R—Nu, or —Q—R(I)n—Nu, —Q—Nu, —R—Nu, or —Nu, where R is defined as above.

Q is a functional linkage arising from the covalent coupling between two functional groups each of which resides originally as substituents on Y and R or Nu, respectively. The introduction of Q in the construct of $R_6$ represents a modular concept which allows the attachment of R—Nu, R(I)n—Nu or Nu directly to a preformed AFAC. Examples of Q include:

—C(O)—, —C(O)NH—, —NHC(O)—, —NHC(O)O—, —NH—, —O—, —S—, —NHC(O)NH—, —NHC(S)NH—, —C(=N+H₂)NH—, —SO₂—, —SO₃—, (I)n is an ionic or ionizable group including but not limited to quaternary ammonium, —COOH, —SO₃H, —SO₄H, —PO₃H₂, and —PO₄H₂, where n is a number of at least 1.

The presence of the ionic or ionizable group(s) will enhance the hydrophilicity of AFAC and compatibility for its usage in aqueous media. The choice and positioning of such ionic or ionizable groups have the advantage of enhancing the binding of the biological molecule/AFAC conjugate to the corresponding binding partners of said biological molecule. Nu is a nucleophilic group on the compound that will facilitate conjugation of compound with biological molecules which may lack nucleophilic group for coupling, but may have electrophilic group or its readily converted precursor. Examples of the protected nucleophilic functional groups or groupings include:

t-Butyloxycarbonylamino and 3-(2-pyridinyldithio)-propionyl (PDP).

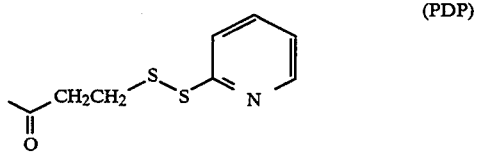

(PDP)

t-Butyloxycarbonyl (t-Boc) is the protective group on amino which can be removed by acid, e.g. trifluoroacetic acid, treatment. The S-2-pyridinyl group in PDP is a protective moiety which can be removed to generate free —SH group upon treatment with dithiothreotol (DTT) at suitable pH. The usage of these protective groups of —NH₂ and —SH nucleophilic groups is known to those skilled in the arts of organic chemistry. Examples of the unprotected nucleophilic functional groups include: amino, thiol, hydroxyl, active methylene adjacent to strong electron-withdrawing group, organic metallic moieties. Examples of such a nucleophilic $R_6$ grouping, its conjugation to biological molecules, and the conjugate utilities have been disclosed in EP-A-0 361 817 (priority U.S. Ser. No. 249,620 (Sep. 26, 1988), abandoned) which is commonly assigned and incorporated herein by reference.

To provide more hydrophilic compounds that can be encapsulated inside liposomes for the purpose of constructing signal-enhancing lumisomes, $R_2$, $R_3$ or $R_6$ can be strongly ionizable groups directly attached or more suitably connected via spacer to the aromatic rings. Examples of strongly ionizable groups include: phosphate, phosphonate, sulfate, and sulfonate. Examples of such a $R_6$ grouping, the incorporation of the hydrophilic chemiluminescent molecules into liposomes and the utility of the resulting lumisomes have been disclosed in EP-A-0 361 817 (priority U.S. Ser. No. 226,639 (Aug. 1, 1988), abandoned) which is commonly assigned and incorporated herein by reference. Similarly, to provide hydrophilic AFAC that can be conjugated with biological molecules directly, $R_2$ and/or $R_3$ can be ionic or strongly ionizable groups directly attached or more suitably connected via spacer to the aromatic-ring fused acridinium nucleus, and $R_6$ can be reactive functional group-containing side chain as recited above. The positions of $R_2$, $R_3$, $R_5$ and $R_6$, and $R_6$ and $R_7$ substituents in all AFAC are interchangeable.

One of the possible precursors to AFAC should be AFAC with the $R_6$ substituent being hydrogen or R, with R defined as above.

When X is nitrogen, Y can be a branched or straight chained alkyl of 1 to 20 carbon atoms or a moiety equal to Formula V above with all the possible substituents as recited, and Z is represented by the following Formula VI:

$$Z=-SO_2-Y' \qquad \text{(Formula VI)}$$

where Y' is a branched or straight chained alkyl of 1 to 20 carbon atoms, halogenated or unhalogenated, or a moiety equal to the Formula V shown above with all the possible substitutents as recited. The substituents to both Y and Y' do not necessarily have to be the same.

A preferred aromatic ring-fused acridinium compounds (AFAC) should be as described above. More preferentially, they are the LBAC series with the following substituents: $R_1$ is a methyl, sulfopropyl or sulfoethyl group; $R_9$, $R_{10}$ are hydrogen, methoxy or halogen; $R_2$ is a hydrogen, 2-MeO, 2-quarternaryammoniumalkoxy, 3-MeO, 3-EtO, 3-quarternaryammoniumalkoxy, or 3-carboxyalkyloxy group; $R_3$, $R_5$ and $R_7$ are hydrogen; when X is oxygen or sulfur, $R_4$ and $R_8$ are methyl, ethyl, isopropyl groups; $R_6$ is one of the following groups attached to the 4-position of Formula V, carboxylate, N-succinimidyloxycarbonyl, benzyloxycarbonyl, N-aminoalkylcarbamoyl, Sulfomethylcarbamoyl, N-[N-(2-amino-3-S-(3'-sulfopropyl)-thiopropionyl)-2-aminoethyl]carbamoyl, N-7-(1,3-disulfonaphthalenyl)carbamoyl, N-[1-carboxyl-2-(3-sulfopropylthio)ethyl]carbamoyl, N-(2-sulfonyloxyethyl)carbamoyl, N-(2-phosphonoethyl)carbamoyl, N-(2-phosphonoxyethyl)carbamoyl and alkoxyiminoethyl; when X is nitrogen, Y represents Formula V with $R_5$ and $R_7$ being hydrogen and $R_6$ being carboxylate, N-succinimidyloxycarbonyl, N-succinimidyloxycarbonylalkyl, benzyloxycarbonyl, or N-aminoalkylcarbamoyl; Z represents Formula VI with Y' being an alkyl or phenyl.

Intermediate compounds which may be utilized to synthesize the chemiluminescent compounds of the present invention include:

An intermediate of the formula:

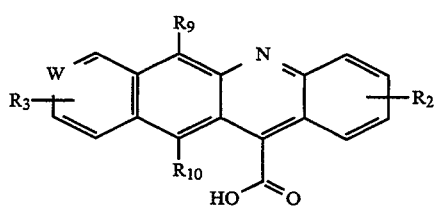

Formula VII where w is carbon;
alternatively, $C_7$, W, $C_9$ or $C_{10}$ can be replaced with —N=;
or W can be omitted and $C_7$ connected to $C_9$, and $C_7$, $C_9$ or $C_{10}$ can be replaced with —O—, —S—, —NH— or —NR—;

$R_2$, $R_3$, $R_9$ and $R_{10}$ are identical or different groups selected from hydrogen, substituted or unsubstituted aryl (ArR or Ar), halide, amino, hydroxyl, nitro, sulfonate, —R, —CN, —COOH, —SCN, —R, —OR, —SR, —SSR, —C(O)R, —C(O)OR, —C(O)NHR, or —NH-C(O)R;

$R_2$ includes a single or multiple substituent at $C_{1-4}$;
$R_3$ includes a single or multiple substituent at $C_7$, W, $C_9$ and $C_{10}$;
$R_2$ can also be a fused aromatic ring with or without heteroatoms; and
R is alkyl, alkenyl, alkynyl, aryl or aralkyl containing optionally up to 20 heteroatoms.

An intermediate of the formula:

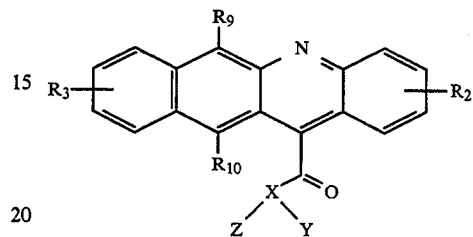

Formula VIII where W is carbon;
alternatively, $C_7$, W, $C_9$ or $C_{10}$ can be replaced with —N=;
or W can be omitted and $C_7$ connected to $C_9$, and $C_7$, $C_9$ or $C_{10}$ can be replaced with —O—, —S—, —NH— or —NR—;

Y is a branched or straight chained alkyl containing optionally up to 20 carbon atoms, halogenated or unhalogenated, or a polysubstituted aryl moiety of the formula:

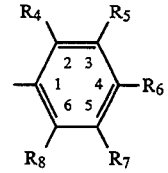

$R_2$, $R_3$, $R_9$ and $R_{10}$ are identical or different groups selected from hydrogen, substituted or unsubstituted aryl (ArR or Ar), halide, amino, hydroxyl, nitro, sulfonate, —R, —CN, —COOH, —SCN, —OR, —SR, —SSR, —C(O)R, —C(O)OR, —C(O)NHR, or —NH-C(O)R;

$R_2$ includes a single or multiple substituent at $C_{1-4}$;
$R_3$ includes a single or multiple substituent at $C_7$, W, $C_9$ or $C_{10}$;
$R_2$ can also be a fused aromatic ring with or without heteroatoms;

X is a heteroatom including nitrogen, oxygen or sulfur, such that when X is oxygen or sulfur Z is omitted, when X is nitrogen then Z is —SO$_2$—Y', Y' is equal to Y and the substituents to Y and Y' do not have to be the same;

$R_4$ and $R_8$ are alkyl, alkenyl, alkynyl, alkoxyl, alkylthiol, amido;
$R_5$ and $R_7$ are any of $R_3$, $R_9$ and $R_{10}$ defined above;
$R_6$=—$R_{11}$—$R_{12}$,
where $R_{11}$ is not required but optionally can be branched or straight-chained alkyl, substituted or unsubstituted aryl or aralkyl containing optionally up to 20 heteroatoms;

and $R_{12}$ is a leaving group or an electrophilic functional group attached with a leaving group or —Q—R—Nu, —Q—R(I)$_n$Nu, —Q—Nu, —R—Nu or Nu where n is a number of at least 1, Nu is a nucleophilic group, Q is a functional linkage, I is an ionic or ionizable group;

$R_5$ and $R_6$, and $R_6$ and $R_7$ are interchangeable; and

R is alkyl, alkenyl, alkynyl, aryl or aralkyl containing optionally up to 20 heteroatoms.

The following examples describe the synthesis of the preferred compounds and intermediates of the present invention, the structures of which are shown in FIG. 1. The examples are intended to illustrate and not to limit the invention and may be used as a guide by those skilled in the art to synthesize compounds having alternate substitutents than those shown in the examples.

EXAMPLE 1

Preparation of
(4-Benzyloxycarbonyl-2,6-dimethyl)phenyl
5-Methyl-benz[b]acridinium-12-carboxylate
Fluorosulfonate (LEAE-Bz)

3-Anilino-2-naphthoic Acid

A mixture of 3-hydroxy-2-naphthoic acid (Aldrich cat. #H4600-7) (376 g, 2.0 mol) and aniline (376 ml, 4.1 mol) was heated at 170° C. with stirring under nitrogen for 16 hours. The resulting mixture, when hot, was poured into 1 N HCl (2.5 ml), heated to 100° C., and stirred at this temperature for 5 minutes. The mixture, when hot, was filtrated and the solid was washed with 0.2 N HCl (600 ml). The wet material was boiled and mechanically stirred with 0.5 N sodium carbonate solution (6.0 ml) for 10 minutes, cooled and filtered. The reddish filtrate was treated dropwise with 5 N HCl with stirring to ~pH 7. The resulting yellow precipitate was collected, washed with small amount of water and crystallized from ethanol (400 ml) to give 3-anilino-2-naphthoic acid (36 g, 7%). Rf 0.6 (silica gel, EM Art. 5715, 20% methanol/chloroform). MS (EI): m/z 264 (M).

12-Chloro-benz[b]acridine

A mixture of 3-anilino-2-naphthoic acid (10.0 g, 37.98 mmol) and phosphorous oxychloride (35.4 ml, 379.8 mmol) was refluxed at 150° C. under nitrogen with stirring for 2 hours. The resulting purple mixture was cooled and evaporated under reduced pressure to dryness. The content was added with stirring to a mixture of chloroform/ice/conc. ammonium hydroxide (200 ml/200 g/200 ml). The chloroform layer was separated and dried over calcium chloride. Removal of the solvent under reduced pressure gave 12-chlorobenz[b]acridine (9.4 g, 95%). Rf 0.8 (silica gel, hexane/ethyl acetate 2:1). MS (EI): m/z 263 (M).

12-Cyano-benz[b]acridine

A mixture of 12-chloro-benz[b]acridine (2.3 g, 8.68 mmol), potassium cyanide (620 mg, 9.55 mmol) and copper(I) cyanide (391 mg, 4.43 mmol) in anhydrous methanol (16 ml) was bubbled with nitrogen for 1 minute and then kept in a sealed tube. The mixture was heated at 160° C. with stirring for 4.5 hours and cooled. The red-brown mixture was evaporated and the residue was flash-chromatographed (W.C. still et al: *J. Org. Chem.*, 43, 2923, (1978)) on a silica column (Baker silica gel, Cat# 7024-1) packed with hexane and eluted with 10% ethyl acetate-hexane, yielding red 12-cyano-benz[b]acridine (1.54 g, 70%). Rf 0.7 (silica gel, hexane/ethyl acetate 2:1). MS (FAB, Thioglycerol Matrix): m/z 255 (M+1).

Benz[b]acridine-12-carboxylic Acid Hydrochloride

A mixture of 12-cyano-benz[b]acridine (557 mg, 2.19 mmol) and tetrabutylammonium bromide (71 mg, 0.22 mmol) in 50% sulfuric acid (v/v, 50 ml) was heated at 160°–170° C. under nitrogen with stirring for 44 hours and cooled. The resulting mixture was poured into ice-water (500 ml); the purple precipitate was collected and washed with water. The wet material was dissolved with warming in 2 N NaOH (100 ml) and then filtered. The filtrate was acidified in an ice-water bath with concentrated HCl to pH 3–4, giving purple benz[b]acridine-12-carboxylic acid hydrochloride (510 mg, 75%). Rf 0.4 (silica gel, chloroform/methanol/water 65:25:4). MS (FAB, Thioglycerol Matrix): m/z 274 (M+1).

(4-Benzyloxycarbonyl-2,6-dimethyl)phenyl Benz[b]acridine-12-carboxylate

A suspension of benz[b]acridine-12-carboxylic acid hydrochloride (370 mg, 1.2 mmol) in anhydrous pyridine (50 ml) was warmed at 60° C. for 5 minutes. The slightly cloudy solution was then cooled to 0° C. and treated with p-toluenesulfonyl chloride (388 mg, 2.33 mmol) at 0° C. for 10 minutes and at room temperature for another 15 minutes to give the first reaction mixture. This reaction mixture was further treated with benzyl 2,6-dimethyl-4-hydroxybenzoate, see U.S. Pat. No. 4,745,181, (694 mg, 2.71 mmol) to give the second reaction mixture, which was stirred at room temperature under nitrogen for 40 hours, and then evaporated under reduced pressure to dryness. The residue was flash-chromatographed on a silica column packed with hexane and eluted with 50% ether-hexane to give orange-red (4-benzyloxycarbonyl-2,6-dimethyl)phenyl benz[b]acridine-12-carboxylate (450 mg, 74%). Rf 0.6 (silica gel, 20% ethyl acetate/toluene). MS (FAB, Thioglycerol Matrix): m/z 512 (M+1).

(4-Benzyloxycarbonyl-2,6-dimethyl)phenyl 5-Methyl-benz[b]acridinium-12-carboxylate Fluorosulfonate (LEAE-Bz)

To a solution of (4-benzyloxycarbonyl-2,6-dimethyl)phenyl benz[b]acridine-9-carboxylate (115 mg, 0.23 mmol) in anhydrous methylene chloride (5 ml) was added methyl fluorosulfonate (0,128 ml, 2.25 mmol). The solution was stirred at room temperature under nitrogen for 20 hours, and then treated with anhydrous ether (10 ml). The resulting precipitate was collected and washed with ether (100 ml), giving dark-brown (4-benzyloxycarbonyl-2,6-dimethyl)phenyl 5-methyl-benz[b]acridinium-12-carboxylate fluorosulfonate (136 mg, 97%). MS (FAB, Thioglycerol Matrix): m/z 526 (M).

EXAMPLE 2

Preparation of
(2,6-Dimethyl-4-N-succinimidyloxycarbonyl)phenyl
5-Methyl-benz[b]acridinium-12-carboxylate
Fluorosulfonate (LEAE-NHS)

(4-Carboxy-2,6-dimethyl)phenyl Benz[b]acridine-12-carboxylate Hydrobromide

A solution of (4-benzyloxycarbonyl-2,6-dimethyl)phenyl benz[b]acridine-12-carboxylate (198 mg, 0.39 mmol), prepared in Example 1, in 30% hydrogen bromide-acetic acid (5 ml) was stirred at 55°–60° C. under nitrogen for 4 hours. The mixture was treated with anhydrous ether (20 ml); the precipitate was collected and washed with ether (100 ml) to give (4-carboxy-2,6-dimethyl)phenyl benz[b]acridine-12-carboxylate hydrobromide quantitatively. Rf 0.4 (silica gel, 5% methanol/chloroform). MS (EI): m/z 421 (M).

(2,6-Dimethyl-4-N-succinimidyloxycarbonyl)phenyl Benz[b]acridine-12-carboxylate

To a solution of (4-carboxy-2,6-dimethyl)phenyl benz[b]acridine-12-carboxylate hydrobromide (108 mg, 0.22 mmol) in anhydrous N,N-dimethylformamide (5 ml) was added at 0° C. dicyclohexylcarbodiimide (111 mg, 0.54 mmol). After stirring at this temperature for 30 minutes, N-hydroxysuccinimide (62 mg, 0.54 mmol) was added. The solution was stirred under nitrogen at 0° C. for 10 minutes and then at room temperature for 24 hours. The resulting mixture was treated with acetic acid (3 drops) and evaporated to dryness under reduced pressure. The residue was extracted with chloroform and the chloroform extract was evaporated under reduced pressure to dryness. The residue was flash-chromatographed on a silica column packed and eluted with ether to give (2,6-dimethyl-4-N-succinimidyloxycarbonyl)phenyl benz[b]acridine-12-carboxylate (20 mg, 18%). Rf 0.6 (silica gel, 20%). MS (EI): m/z 518 (M).

(2,6-Dimethyl-4-N-succinimidyloxycarbonyl)phenyl 5-Methyl-benz[b]acridinium-12-carboxylate Fluorosulfonate (LEAE-NHS)

To a solution of (2,6-dimethyl-4-N-succinimidyloxycarbonyl)phenyl benz[b]acridine-12carboxylate (14 mg, 0.026 mmol) in anhydrous methylene chloride (1 ml) was added methyl fluorosulfonate (0.021 ml, 0.26 mmol). The resulting brown solution was stirred at room temperature under nitrogen for 20 hours, and then treated with anhydrous ether (1 ml). The precipitate was collected and washed with ether (40 ml), yielding (2,6-dimethyl-4-N-succinimidyloxycarbonyl)phenyl 5-methylbenz[b]acridinium-12-carboxylate-fluorosulfonate (11 mg, 65%). MS (FAB, Thioglycerol Matrix): m/z 533 (M).

EXAMPLE 3

Preparation of (4-Benzyloxycarbonyl-2,6-diisopropyl)phenyl 5-Methyl-benz[b]acridinium-12-carboxylate Fluorosulfonate (DIP-LEAE-Bz)

3,5-Diisopropyl-4-hydroxybenzoic acid

This acid was prepared according to the procedure of W. H. Meek et al. *J. Chemical and Engineering Data,* 14(3), 388, (1969). To a solution of 2,6-diisopropylphenol (Aldrich cat. #D12660-8) (37.0 ml, 0.20 mol) in anhydrous N,N-dimethylacetamide (150 ml) was added sodium methoxide (16.2 g, 0.30 mol). Carbon dioxide was passed through the mixture throughout the subsequent reaction period. The mixture was heated with stirring and the solvent was slowly distilled out during 2 hours of the period until the pot temperature reached to 180° C.. The mixture was allowed to continue stirring at 180° C. for another 1.5 hours and then cooled to 90° C. The flow of carbon dioxide was discontinued and water (400 ml) was added. The mixture, after further cooled to room temperature, was washed with toluene (4×60 ml) and then treated with conc. hydrochloric acid in an ice-water bath to pH 3. The resulting mixture was extracted with diethyl ether (2×150 ml); the ether extract was washed with brine (100 ml) and dried over anhydrous magnesium sulfate. Removal of the solvent under reduced pressure gave 3,5-diisopropyl-4-hydroxybenzoic acid (10.4 g, 23%). Rf 0.5 (silica gel, 50% diethyl ether/hexane). MS (CI, CH$_4$): m/z 223 (M+1).

Benzyl 3,5-Diisopropyl-4-hydroxybenzoate

To a solution of 3,5-diisopropyl-4-hydroxybenzoic acid (1,223 g, 5.50 mmol) in methanol (25 ml) was added potassium hydroxide (308 mg, 5.50 mmol) in water (5 ml). The resulting solution was stirred at room temperature under nitrogen for 1 hour, and then evaporated completely to dryness under reduced pressure. This potassium salt was dissolved in anhydrous acetonitrile (30 ml) and N,N-dimethylformamide (15 ml), and treated with dibenzo-18-crown-6 (198 mg, 0.55 mmol). After 30 minutes of stirring at 80° C. under nitrogen, the solution was further treated with benzyl bromide (0,712 ml, 6.05 mmol). The stirring was continued at 80° C. under nitrogen for 4 hours. The resulting mixture, after cooling, was filtrated. The filtrate was evaporated under reduced pressure to dryness. The residue was flash-chromatographed on a silica column packed with hexane and eluted with 20% ethyl acetate/hexane, yielding crystalline benzyl, 3,5-diisopropyl-4-hydroxybenzoate (1.35 g, 79%). Rf 0.6 (silica gel, 20% ethyl acetate/toluene). MS(EI). m/z 312 (M).

(4-Benzyloxycarbonyl-2,6-diisopropyl)phenyl Benz[b]acridine-12-carboxylate

A suspension of benz[b]acridine-12-carboxylic acid hydrochloride from Example 1 (200 mg, 0.65 mmol) in anhydrous pyridine (30 ml) was warmed at 60° C. for 5 minutes. The slightly cloudy solution was then cooled to 0° C. and treated with p-toluenesulfonyl chloride (247 mg, 1.29 mmol). The solution was stirred at 0° C. for 40 minutes and room temperature for another 10 minutes, and benzyl 2,6 -diisopropyl-4-hydroxybenzoate (202 mg, 0.65 mmol) was added. This reaction mixture was allowed to continue stirring at room temperature under nitrogen for 20 hours, and then evaporated under reduced pressure to dryness. The residue was flash-chromatographed on a silica column packed with hexane and eluted with 25% ether-hexane to give orange (4-benzyloxycarbonyl-2,6-diisopropyl)phenyl benz[b]acridine-12-carboxylate (187 mg, 51%). Rf 0.6 (silica gel, 20% ethyl acetate/toluene). MS(CI, CH4): m/z 570 (M+3).

(4-Benzyloxycarbonyl-2,6-diisopropyl)phenyl 5-Methyl-benz[b]acridinium-12-carboxylate Fluorosulfonate (DIP-LEAE-Bz)

To a solution of (4-Benzyloxycarbonyl-2,6-diisopropyl)phenyl benz[b]acridine-12-carboxylate (50 mg, 0.088 mmol) in anhydrous methylene chloride (3 ml) was added methyl fluorosulfonate (0.072 ml, 0.088 mmol). The brown solution was stirred at room temperature under nitrogen for 24 hours, and then treated with anhydrous ether (4 ml). The resulting precipitate was collected and washed with ether (10 ml), giving dark-brown (4-benzyloxycarbonyl-2,6-diisopropyl)phenyl 5-Methyl-benz[b]acridinium-12-carboxylate fluorosulfonate (39 mg, 64%). MS (FAB, Thioglycerol Matrix): m/z 582 (M).

EXAMPLE 4

Preparation of N-(4-Methoxyphenyl-N-[3-(benzyloxycarbonyl)-phenylsulfonyl]5-Methyl-benz[b]acridinium-12-carboxamide Fluorosulfonate (LEAC-Bz)

3-[N-(4-Methoxyphenyl)sulfamido]benzoic acid

To a solution of 3-(chlorosulfonyl)benzoic acid (Kodak cat. #1188655) (4.4 g, 20.00 mmol) and triethylamine (2.78 ml, 20.00 mmol) in anhydrous methylene chloride (40 ml) was added at 0° C. 4-anisidine (2.46 g, 20.00 mmol). After 10 minutes of stirring at 0° C., a large quantity of precipitate formed from the solution. The mixture was allowed to continue stirring at room temperature under nitrogen for 2 hours. After filtration, the collected off-white solid was washed with water (50 ml) and then with ether (50 ml), giving 3-[N-(4-methoxyphenyl)sulfamido]benzoic acid (4.50 g, 74%). Rf 0.5 (silica gel, chloroform/methanol/water 65:25:4). MS(CI, CH4): m/z 308 (M+1).

Benzyl 3-[N-(4-Methoxyphenyl)sulfamido]benzoate

To a solution of 3-[N-(4-methoxyphenyl)sulfamido]benzoic acid (2.00 g, 6.52 mmol) in N,N-dimethylformamide (20 ml) was added a solution of sodium hydroxide (260.6 mg, 6.52 mmol) in water (5 ml). The resulting solution was stirred at room temperature under nitrogen for 1 hour, and then evaporated completely to dryness under reduced pressure. This sodium salt was dissolved in anhydrous acetonitrile (40 ml) and N,N-dimethylformamide (20 mL), and treated with dibenzo-18-crown-6 (235 mg, 0.65 mmol). After 30 minutes of stirring at 80° C. under nitrogen, the solution was further treated with benzyl bromide (0.852 ml, 7.27 mmol). The stirring was continued at 80° C. under nitrogen for 4 hours. The resulting mixture, after cooling, was filtrated. The white solid was washed with small amount of acetonitrile. The combined acetonitrile filtrate was evaporated under reduced pressure to dryness. The reside was flash-chromatographed on a silica column packed with hexane and eluted with 15% ethyl acetate/hexane, yielding crystalline benzyl 3-[N-(4-methoxyphenyl)sulfamido]benzoate (2.00 g, 77%). Rf 0.5 (silica gel, 20% ethyl acetate/toluene). MS(CI, CH4): m/z 397 (M+1).

N-(4-Methoxyphenyl)-N-[3-(benzyloxycarbonyl)phenylsulfonyl]Benz[b]acridine-12-carboxamide A suspension of benz[b]acridine-12-carboxylic acid hydrochloride (200 mg, 0.65 mmol) in anhydrous pyridine (30 ml) was warmed at 60° C. for 5 minutes. The slightly cloudy solution was then cooled to 0° C., and treated with p-toluenesulfonyl chloride (247 mg, 1.29 mmol). The solution was stirred at 0° C. for 40 minutes and room temperature for another 10 minutes, and benzyl 3-[N-(4-methoxyphenyl)sulfamido]benzoate (257 mg, 0.65 mmol) was added. This reaction mixture was allowed to continue stirring at room temperature under nitrogen for 20 hours, and then was evaporated under reduced pressure to dryness. The residue was flash-chromatographed on a silica column packed with hexane and eluted with 25% hexane-ether to give orange N-(4-methoxyphenyl)-N-[3-(benzyloxycarbonyl)phenylsulfonyl]benz[b]acridine-12carboxamide (177 mg, 68%). Rf 0.4 (silica gel, 20% ethyl acetate/toluene). MS(CI, CH4): m/z 653 (M+1).

N-(4-Methoxyphenyl)-N-[3-(benzyloxycarbonyl)phenylsulfonyl]5-Methyl-benz[b]acridinium-12-carboxamide Fluorosulfonate (LEAC-Bz)

To a solution of N-(4-methoxyphenyl)-N-[3-(benzyloxycarbonyl)phenylsulfonyl]benz[b]acridinium-12-carboxamide (50 mg, 0.077 mmol) in anhydrous methylene chloride (3 ml) was added methyl fluorosulfonate (0.062 ml, 0.77 mmol). The dark-brown solution was stirred at room temperature under nitrogen for 20 hours, and treated with anhydrous ether (10 ml). The resulting precipitate was collected and washed with ether (10 ml), giving blue-black N-(4-methoxyphenyl)-N-[3-(benzyloxycarbonyl)phenylsulfonyl]5-methyl-benz[b]acridinium-12-carboxamide fluorosulfonate (38 mg, 65%). MS (FAB, Thioglycerol Matrix): m/z 667 (M).

EXAMPLE 5

Preparation of (4-Benzyloxycarbonyl-2,6-dimethyl)phenyl 3-Ethoxy-5-methyl-benz[b]acridinium-12 -carboxylate Fluorosulfonate (3-EtO-LEAE-Bz)

Benzo[5,6]isatin

Benzo[5,6]isatin was prepared according to the procedure of A. Etienne and A. Staehelin, Bull. Soc. Chim. France., 6, 743, (1954).

3-Hydroxy-benz[b]acridine-12-carboxylic Acid

A mixture of benzo[5,6]isatin (500 mg, 2.54 mmol) and potassium hydroxide (996 mg, 17.78 mmol) in water (2 ml) and n-butanol (2 ml) was heated with stirring to 100° C. to give a homogeneous solution, followed by addition of resorcinol (1.95 g, 17.78 mmol). After the solution was further heated to 140° C. and the solvents were slowly blown away with nitrogen during a 30-minute period, another 2 ml of water and 1 ml of n-butanol were added. The temperature of the solution was maintained at 140° C. while blowing of nitrogen continued for a total of 2 hours. The gummy mixture was cooled and dissolved in 100 ml of water; the solution was acidified with concentrated hydrochloric acid in an ice-water bath to pH 2. The resulting precipitate was collected, washed with water, and flash-chromatographed on a silica column packed with chloroform and eluted with 20% methanol-chloroform followed by chloroform-methanol-water (65:25:4) to give 3-hydroxy-benz[b]acridine-12-carboxylic acid (210 mg, 29%). Rf 0.3 (silica gel, chloroform/methanol/water 65:25:4). MS (FAB, Thioglycerol Matrix): m/z 290 (M+1).

Ethyl 3-Ethoxy-benz[b]acridine-12-carboxylate

To a mixture of 3-hydroxy-benz[b]acridine-12-carboxylic acid (90 mg, 0.28 mmol) and cesium carbonate (451 mg, 1.38 mmol) in methyl sulfoxide (3.5 ml) was added bromoethane (207 ul, 2.77 mmol). The mixture was stirred under nitrogen at 25° C. for 4 hours, and treated with water (10 ml). The mixture was adjusted to pH 5 with 5% HCl; the resulting precipitate was collected and washed with water. The crude product was purified on a silica column packed with chloroform and eluted with 5% methanol-chloroform to give ethyl 3-ethoxy-benz[b]acridinium-12-carboxylate (36 mg, 38%). Rf 0.5 (silica gel, diethyl ether/hexane 3:1). MS (FAB, Thioglycerol Matrix): m/z 346 (M+1).

3-Ethoxy-benz[b]acridinium-12-carboxylic Acid Hydrochloride

A solution of ethyl 3-ethoxy-benz[b]acridinium-12-carboxylate (35 mg, 0.10 mmol) in 16% sodium hydroxide (1 ml) and methanol (3 ml) was stirred under nitrogen at 25° C. for 2 days and at 40° C. for additional 4 hours, and then evaporated to dryness under reduced pressure. The residue was suspended in water (20 ml) and adjusted to pH 3 in an ice-water bath with concentrated HCl. The precipitate was collected and washed with water to give 3-ethoxy-benz[b]acridine-12-carboxylic acid hydrochloride (30 mg, 3%). Rf 0.8 (silica gel, chloroform/methanol/water 65:25:4). MS (CI, CH4): m/z 318 (M+1).

(4-Benzyloxycarbonyl-2,6-dimethyl)phenyl 3-Ethoxy-benz[b]acridine-12-carboxylate A slightly-cloudy solution of 3-ethoxy-benz[b]acridine-12-carboxylic acid hydrochloride (19 mg, 0.054 mmol) in pyridine (1 ml) and N,N'-dimethylpropyleneurea (DMPU, 1.5 ml) was cooled at 0° C. and p-toluenesulfonyl chloride (21 mg, 0.11 mmol) was added. After 20 minutes of stirring, benzyl 3,5-dimethyl-4-hydroxybenzoate (14 mg, 0.055 mmol) and N,N'-dimethylaminopyridine (1 mg) were added. The mixture was stirred at 25° C. under nitrogen for 20 hours and then evaporated under reduced pressure to dryness. The residue was treated with water (5 ml) and extracted with ether (5× 5 ml). The combined ether layer was washed with water (1×10 ml), brine (1×10 ml) and dried over magnesium sulfate. Removal of the solvent under reduced pressure gave a crude mixture, which was separated on a preparative-TLC plate (2 mm silica gel, EM Art. 5717) by developing with ether/hexane (3:2). The major orange band was collected and extracted with 10% methanol/ether. Removal of the solvents under reduced pressure gave orange (4-benzyloxycarbonyl-2,6-dimethyl)phenyl 3-ethoxy-benz[b]acridine-12-carboxylate (5 mg, 17%). Rf 0.6 (silica gel, diethyl ether/hexane). MS (FAB, Thioglycerol Matrix): m/z 556 (M+1).

(4-Benzyloxycarbonyl-2,6-dimethyl)phenyl 3-Ethoxy-5-methyl-benz[b]acridinium-12-carboxylate Fluorosulfonate (3-EtO-LEAE-Bz)

To a solution of (4-benzyloxycarbonyl-2,6-dimethyl)phenyl 3-ethoxy-benz[b]acridine-12-carboxylate (9 mg, 0.0162 mmol) in methylene chloride (1 ml) was added methyl fluorosulfonate (13.1, 0.162 mmol). The solution was stirred at 25° C. under nitrogen for 36 hours and then treated with diethyl ether (10 ml). The precipitate was collected and washed with diethyl ether (20 ml), giving (4-benzyloxycarbonyl-2,6-dimethyl)phenyl-3-ethoxy-5-methylbenz[b]acridinium-12-carboxylate fluorosulfonate (3-EtO-LEAE-Bz, 7 mg, 65%) MS (CI, CH4): m/z 570 (M+2).

EXAMPLE 6

Preparation of (4-Benzyloxycarbonyl-2,6-dimethyl)phenyl 3- (N, N-Diethyl-N-methyl-ammonium) ethoxy-5-methyl-benz[b]acridinium-12-carboxylate Difluorosulfonate (3-QAE-LEAE-Bz )

N,N-Diethylaminoethyl 3-(N,N-Diethylamino)ethoxy-benz[b]acridine-12-carboxylate

A solution of 3-hydroxy-benz[b]acridine-12-carboxylic acid (415 mg, 1.28 mmol) in methyl sulfoxide (12 ml) was treated with cesium carbonate (5 g, 15.4 mmol) at 25° C. for 10 minutes and diethylamminoethyl bromide hydrobromide (1.5 g, 6.4 mmol) was added. The mixture was stirred at 25° C. under nitrogen for 4 hours and then quenched with water (100 ml). The precipitate was collected and washed with water (50 ml). The crude product was separated on 4 preparative-TLC plates (2mm silica gel) by developing with 20% methanol/chloroform. The orange band was collected and extracted with 10% methanol/chloroform. Removal of the solvents under reduced pressure gave N,N-diethylaminoethyl 3-(N,N-diethylamino)ethoxy-benz[b]acridine-12-carboxylate (73 mg, 12%). Rf 0.6 (silica gel, 20% methanol/chloroform). MS (CI, CH4): m/z 488 (M+1).

3-(N,N-Diethylamino)ethoxy-benz[b]acridine-12-carboxylic acid hydrochloride

A solution of N,N-diethylaminoethyl 3-(N,N-diethylamino)ethoxy-benz[b]acridine-12-carboxylate (60 mg, 0.123 mmol) in 4 N sodium hydroxide (4 ml) and methanol (12 ml) was stirred at 65° C. under nitrogen for 16 hours, and then evaporated under reduced pressure to dryness. The residue was dissolved in water (10 ml); the solution was carefully acidified in an ice-water bath with concentrated HCl to pH 4. The resulting precipitate was collected and washed with diethyl ether (5 ml) to give 3-(N,N-diethylamino)ethoxy-benz[b]acridine-12-carboxylic acid hydrochloride (32 mg, 61%). Rf 0.3 (silica gel, chloroform/methanol/water 65:25:4).

(4-Benzyloxycarbonyl-2,6-dimethyl)phenyl 3-(N,N-Diethylamino)ethoxy-benz[b]acridine-12-carboxylate A mixture of 3-(N,N-diethylamino)ethoxybenz[b]acridine-12-carboxylic acid hydrochloride (29 mg, 0.069 mmol) and p-toluenesulfonyl chloride (29 mg, 0.152 mmol) in pyridine (12 ml) was stirred at 80° C. for 5 minutes. The resulting homogeneous solution was cooled to 25° C. and further treated with benzyl 4-hydroxy-3,5-dimethylbenzoate (20 mg, 0.078 mmol). After stirring at 25° C. under nitrogen for 16 hours, the solvent was removed under reduced pressure. The residue was purified on a preparative-TLC plate (2mm silica gel) developed with 15% methanol/chloroform. The orange band was collected and extracted with 10% methanol/chloroform. Evaporation of the solvents under reduced pressure gave (4-benzyloxycarbonyl-2,6-dimethyl)phenyl 3-(N,N-diethylamino)ethoxy-benz[b]acridine-12-carboxylate (17 mg, 39%). Rf 0.6 (silica gel, 10% methanol/chloroform). MS (FAB, Glycerol Matrix): m/z 627 (M+1).

(4-Benzyloxycarbonyl-2,6-dimethyl)phenyl 3-(N,N,Diethyl-N-methyl-ammonium) ethoxy-5-methyl-benz[b]acridinium-12-carboxylate Difluorosulfonate (3-QAE-LEAE-Bz)

A solution of (4-benzyloxycarbonyl-2,6-dimethyl)phenyl 3-(N,N-diethylamino)ethoxy-benz[b]acridine-12-carboxylate (13 mg, 0.0208 mmol) in methylene chloride (1.9 ml) was treated with methyl fluorosulfonate (25 ul, 0.308 mmol). After 15 hours of stirring under nitrogen at 25° C. the reaction mixture was slowly added to diethyl ether (5 ml). The precipitate was collected and washed with ether (10 ml) to give (4-benzyloxycarbonyl-2,6-dimethyl)phenyl 3-(N,N-diethyl-N-methyl-ammonium)ethoxy-5-methylbenz[b]acridinium-12-carboxylate difluorosulfonate (3-QAE-LEAE-Bz, 9 mg, 53%). MS (FAB, Glycerol Matrix): m/z 659 (M+3).

EXAMPLE 7

Preparation of (4-Benzyloxycarbonyl-2,6-dimethyl)phenyl 2-Methoxy-5-methyl-benz[b]acridinium-12-carboxylate Fluorosulfonate (2-MeO-LEAE-Bz)

3-(4-Methoxy)anilino-2-naphthoic Acid

A mixture of p-anisidine (84.7 g, 687.7 mmol) and 3-hydroxy-2-naphthoic acid (64.7 g, 343.9 mmol) was mechanically stirred at 160° C. under nitrogen for 22 hours. After cooling to 130° C., the mixture was treated with hot 1 N hydrochloric acid (1000 ml), stirred at 130° C. for 10 minutes, and filtrated, when hot. The resulting cake was stirred with hot 0.5 N sodium carbonate (2200 ml) for 15 minutes and filtrated when hot. The filtrate was cooled and acidified to pH 6.5 with concentrated HCl in an ice-water bath. The precipitate was collected and washed with methanol (150 ml), yielding 3-(4-methoxy) anilino-2-naphthoic acid (14.8 g, 15%). Rf 0.6 (silica gel, 10% methanol/chloroform). MS (CI, CH4): m/z 294 (M+1).

12-Chloro-2-methoxy-benz[b]acridine

A mixture of 3-(4-methoxy)anilino-2-naphthoic acid (15.4 g, 49.44 mmol) and phosphorousoxy chloride (46 ml, 494.4 mmol) was refluxed at 120° C. under nitrogen for 3.5 hours, and then evaporated under reduced pressure to dryness. The residue was taken into a mixed solvent containing chloroform (500 ml)/ice (450 g)/ammonium hydroxide (450 ml). The resulting two layers were separated. The aqueous layer was extracted with chloroform (3×250 ml). The combined chloroform layer was dried over calcium chloride and evaporated to dryness under reduced pressure, yielding 12-chloro-2-methoxy-benz[b]acridine (12.5 g, 86%). Rf 0.8 (silica gel, 60% diethyl ether/hexane). MS (CI, CH4): m/z 294 (M+1).

12-Cyano-2-methoxy-benz[b]acridine

A mixture of 12-chloro-2-methoxy-benz[b]acridine (562 mg, 1.905 mmol), potassium cyanide (136 mg, 2.096 mmol) and copper(I) cyanide (86 mg, 0.953 mmol) in methanol (3.7 ml) was stirred at 170° C. in a sealed-tube for 4.5 hours. The resulting mixture was filtrated, and the solid was washed with chloroform/methanol (2:1, 10 ml). The combined filtrate was evaporated under reduced pressure to give a residue, which was flash-chromatographed on a silica column packed with chloroform and eluted with 1% methanol/chloroform to yield 12-cyano-2-methoxybenz[b]acridine (477 mg, 88%). Rf 0.6 (silica gel, 1% methanol/chloroform). MS (CI, CH4): m/z 285 (M+1).

2-Hydroxy-benz[b]acridine-12-carboxylic acid hydrosulfate

A mixture of 12-cyano-2-methoxy-benz[b]acridine (8.3 g, 29.1 mmol) and 50% sulfuric acid (v/v, 280 ml) was mechanically stirred under nitrogen at 160° C. for 48 hours. The resulting mixture was cooled and poured into ice-water (1800 ml). The precipitate was collected, washed with water (200 ml), and flash-chromatographed on a silica column packed with chloroform and eluted with 20% methanol/chloroform followed by chloroform/methanol/water (65:25:4) to give 2-hydroxy-benz[b]acridine-12-carboxylic acid hydrosulfate (4.8 g, 43%). Rf 0.4 (silica gel, chloroform/methanol/water 65:25:4).

Methyl 2-Methoxy-benz[b]acridine-12-carboxylate

To a solution of 2-hydroxy-benz[b]acridine-12-carboxylic acid hydrochloride (186 mg, 0.572 mmol) in methyl sulfoxide (4 ml) were added cesium carbonate (746 mg, 2.29 mmol) and iodomethane (143 ul, 2.29 mmol). The resulting mixture was stirred at 25° C. under nitrogen for 4 hours and then treated with water (50 ml). The mixture was acidified in an ice-water bath with concentrated HCl to pH 6. The resulting precipitate was collected, washed with water (5 ml) and air-dried. The crude mixture was purified on 4 preparative-TLC plates (2 mm silica gel) developed with diethyl ether/hexane (5:1); the major orange band was collected and extracted with 10% methanol/chloroform. Removal of the solvents under reduced pressure gave methyl 2-methoxy-benz[b]acridine-12-carboxylate (35 mg, 17%). Rf 0.8 (silica gel, diethyl ether/hexane 5:1).

2-Methoxy-benz[b]acridine-12-carboxylic Acid

A solution of methyl 2-methoxy-benz[b]acridine-12-carboxylate (35 mg, 0.10 mmol) in 4N sodium hydroxide (3 ml) and methanol (9 ml) was stirred at 65° C. for 15 hours. The resulting mixture was evaporated under reduced pressure to dryness. The residue was dissolved in water (40 ml); the aqueous solution was acidified to pH 5 with concentrated HCl in an ice-water bath. The precipitate was collected and washed with water (5 ml), yielding 2-methoxybenz[b]acridine-12-carboxylic acid (20 mg, 59%). Rf 0.5 (silica gel, chloroform/methanol/water 65:25:4). MS (CI, CH4: m/z 304 (M+1).

(4-Benzyloxycarbonyl-2,6-dimethyl)phenyl 2-Methoxy-benz[b]acridine-12-carboxylate A solution of 2-methoxy-benz[b]acridine-12-carboxylic acid (18 mg, 0.0529 mmol) in pyridine (5 ml) was treated with p-toluenesulfonyl chloride (20 mg, 0.106 mmol) at 25° C. for 15 minutes and then benzyl 3,5-dimethyl-4-hydroxybenzoate (27 mg, 0,106 mmol) was added. After 15 hours of stirring at 25° C. under nitrogen, the reaction mixture was evaporated under reduced pressure to remove the pyridine. The residue was purified on a preparative-TLC (2 mm silica gel) developed with diethyl ether/hexane (3:2). The orange band was collected and extracted with 5% methanol/chloroform. Removal of the solvents under reduced pressure gave (4-benzyloxycarbonyl-2,6-dimethyl)phenyl 2-methoxy-benz[b]acridine-12-carboxylate (2.7 mg, 9%). Rf 0.5 (silica gel, 60% diethyl ether/hexane).

(4-Benzyloxycarbonyl-2,6-dimethyl)phenyl 2-Methoxy-5-methyl-benz[b]acridinium-12-carboxylate Fluorosulfonate (2-MeO-LEAE-Bz)

A solution of 4-benzyloxycarbonyl-2,6-dimethyl)phenyl 2-methoxy-benz[b]acridine-12-carboxylate (2.5 mg, 0.0046 mmol) in methylene chloride (1 ml) was treated with methyl fluorosulfonate (3.7 ul, 0.56 mmol) at 25° C. with stirring under nitrogen for 15 hours. The reaction mixture was added to anhydrous diethyl ether (4 ml). The resulting precipitate was collected and washed with diethyl ether (5 ml) to afford (4-benzyloxycarbonyl-2,6-dimethyl)phenyl 2-methoxy-5-methyl-benz[b]acridinium-12-carboxylate fluorosulfonate (2-MeO-LEAE-Bz) (1.5 mg, 49%). MS (FAB, Thioglycerol Matrix): m/z 556(M).

EXAMPLE 8

Preparation of
(2,6-Dimethyl-4succinimidyloxycarbonyl)phenyl
5-Methyl-2-(trimethylammonium)ethoxy-benz[b]acridinium-12-carboxylate Difluorosulfonate
(2-QAE-LEAE-NHS)

N,N-Dimethylaminoethyl 2-(N,N-Dimethylamino)ethoxybenz[b]acridine-12-carboxylate To a solution of 2-hydroxy-benz[b]acridine-12-carboxylic acid hydrochloride (360 mg, 1,108 mmol) in methyl sulfoxide (11 ml) were added cesium carbonate (3.61 g, 11.08 mmol) and N,N-dimethylaminoethyl bromide hydrobromide (1.03 g, 4.432 mmol). After 15 hours of stirring at 60° C. under nitrogen, the reaction mixture was diluted with methyl sulfoxide (20 ml) and filtered to remove the insoluble impurities. The filtrate was concentrated under reduced pressure to a small volume, which was separated on a preparative-TLC plate (2 mm silica gel) by developing with chloroform/methanol/water (47:48:5). The desired orange band was collected and extracted with 25% methanol/chloroform. Removal of the solvents under reduced pressure gave N,N-dimethylaminoethyl 2-(N,N-dimethylamino)ethoxy-benz[b]acridine-12-carboxylate (86 mg, 18%). Rf 0.6 (silica gel, chloroform/methanol/water 65:25:4). MS (FAB, Glycerol Matrix): m/z 432 (M+1).

2-(N,N-Dimethylamino)ethoxy-benz[b]acridine-12-carboxylic acid

A solution of N,N-dimethylaminoethyl 2-(N,N-dimethylamino)ethoxy-benz[b]acridine-12-carboxylate (86 mg, 0.20 mmol ) in 4 N sodium hydroxide (7.3 ml) and methanol (22 ml) was stirred at 65° C. for 1 hour and at 35° C. for 15 hours. The reaction mixture was evaporated under reduced pressure to dryness. The residue was washed with water (5 ml) and air-dried, yielding 2-(N,N-dimethylamino)ethoxybenz[b]acridine-12-carboxylic acid (23 mg, 32%). Rf 0.3 (silica gel, chloroform/methanol/water 65:25:4). MS (FAB, Glycerol Matrix): m/z 361 (M+1).

Succinimidyl 3,5-Dimethyl-4-hydroxy-benzoate

A solution of 3,5-dimethyl-4-hydroxybenzoic acid (5.0 g, 30.0 mmol) in N,N-dimethylformamide (150 ml) was cooled to 0° C. and treated with N-hydroxysuccinimide (3.45 g, 30.0 mmol) and 1,3-dicyclohexylcarbodiimide (6.81 g, 33.0 mmol). The solution was stirred under nitrogen at 0° C. for 2 hours and then at 25° C. for 16 hours. The resulting mixture was stirred with 0.5 ml of acetic acid for 15 minutes, and then filtered to remove the insoluble urea. The filtrate was evaporated under reduced pressure to dryness. The dried material was washed with diethyl ether (100 ml) and suspended in boiling ethyl acetate (200 ml). The suspension, when hot, was filtered to remove insoluble impurities. The filtrate was concentrated and suspended in hot ethyl acetate/methylene chloride (1:1, 200 ml) and cooled to give an off-white powder in 2.91 g (37%). Rf 0.6 (silica gel, diethyl ether).

(2,6-Dimethyl-4-succinimidyloxycarbonyl)phenyl 2-N,N-Dimethylamino)ethoxy-benz[b]acridine-12-carboxylate A solution of 2-(N,N-dimethylamino)ethoxy-benz[b]acridine-12-carboxylic acid (30 mg, 0.0833 mmol) in pyridine (4 ml) was treated with p-toluenesulfonyl chloride (31.8 mg, 0,166 mmol) at 25° C. for 10 minutes, followed by addition of succinimidyl 3,5-dimethyl-4-hydroxybenzoate (32 mg, 0.0833 mmol). After 15 hours of stirring at 25° C. under nitrogen, the solution was diluted with chloroform (10 ml), quickly washed with water (3×4 ml) and evaporated under reduced pressure to dryness. The residue was purified on two preparative-TLC plates (1 mm silica gel) developed with 10% methanol/chloroform. The desired orange band was collected and extracted with 10% methanol/chloroform. Removal of the solvents under reduced pressure gave (2,6-dimethyl-4-succinimidyloxycarbonyl)phenyl 2-(N,N-dimethylamino)ethoxy-benz[b]acridine-12-carboxylate (7 mg, 14%). Rf 0.8 (silica gel, 10% methanol/chloroform). MS (FAB, Thioglycerol Matrix): m/z 606 (M+1).

(2,6-Dimethyl-4-succinimidyloxycarbonyl)phenyl 5-Methyl-2-(trimethylammonium)ethoxy-benz[b]acridinium-12-carboxylate Difluorosulfonate (2-QAE-LEAE-NHS)

A solution of 2,6-dimethyl-4-N-succinimidyloxycarbonyl)phenyl 2-(N,N-dimethyl amino)ethoxybenz[b]acridine carboxylate (1.9 mg, 0.0031 mmol) in anhydrous methylene chloride (4 ml) was treated with methyl fluorosulfonate (3.8 ul, 0.0465 mmol). The solution was allowed to stir at 25° C. under nitrogen for 16 hours. The resulting precipitate was collected and washed with diethyl ether (2 ml) to give (2,6-dimethyl-4-succinimidyloxycarbonyl)phenyl 5-methyl-2-(trimethylammonium)ethoxy-benz[b]acridinium-12-carboxylate difluorosulfonate (2-QAE-LEAE-NHS) (1.0 mg, 39%).

EXAMPLE 9

Preparation of (4-Benzyloxycarbonyl-2,6-dimethyl)phenyl 5-(3-Sulfopropyl)-benz[b]acridinium-12-carboxylate (NSP-LEAE-Bz)

(4-Benzyloxycarbonyl-2,6-dimethyl)phenyl 5-(3-Sulfopropyl)-benz[b]acridinium-12-carboxylate (NSP-LEAE-Bz)

A mixture of (4-benzylcarboxyl-2,6-dimethyl)phenyl benz[b]acridine-12-carboxylate from Example 1 (30 mg, 0.0587 mmol) and 1,3-propane sulton (600 mg, 4.9 mmol) was flushed with nitrogen and kept in a sealed tube. The tube was heated with stirring at 180° C. for 5 hours and then cooled. The resulting mixture was purified by reverse-phase preparative-HPLC on a C-18 column (YMC SH-344-15, S-15, 128), eluted under gradient condition with 25% to 40% acetonitrile in 0.05 M aqueous trifluoroacetic acid from 0 to 20 minutes, 40% to 90% over 5 minutes, and maintaining 90% acetonitrile for another 10 minutes. The fraction with retention time of 17 minutes was collected and evaporated under reduced pressure to give 3.2 mg of the title compound (NSP-LEAE-Bz). MS (FAB, Glycerol Matrix): m/z 634 (M+1).

EXAMPLE 10

Preparation of (2,6-Dimethyl-4-N-succinimidyloxycarbonyl)phenyl 2-Methoxy-5-(2-sulfoethyl)-benz[b]acridinium-12-carboxylate (2-MeO-NSE-LEAE-NHS)

(2,6-Dimethyl-4-N-succinimidyloxycarbonyl)phenyl 2-Methoxy-benz[b]acridinium-12-carboxylate A mixture of 2-methoxy-benz[b]acridine-12-carboxylic acid from Example 7 (208 mg, 0.6118 mmol) in pyridine (20 ml) was treated with p-toluenesulfonyl chloride (233 mg, 1.2235 mmol) at 25° C. for 10 minutes, followed by addition of succinimidyl 3,5-dimethyl-4-hydroxy-benzoate (161 mg, 0.6118 mmol). After 24 hours of stirring under nitrogen at 25° C., the pyridine was removed by evaporation under reduced pressure. The resulting mixture was flash-chromatographed on a silica column packed and eluted with diethyl ether. The crude product collected was further purified on a Chromatotron plate (1 mm silica gel) by elution with diethyl ether to yield 80 mg (24%) of the pure product. Rf 0.8 (silica gel, ethyl acetate/hexane 2:1). MS (FAB, Thioglycerol Matrix): 549 (M+1).

2,6-Dimethyl-4-N-succinimidyloxycarbonyl)phenyl 2-Methoxy-5-(2-sulfoethyl)-benz[b]acridinium-12-carboxylate (2-MeO-NSE-LEAE-NHS )

A mixture of (2,6-dimethyl-4-N-succinimidyloxycarbonyl)phenyl 2-methoxy-benz[b]acridine-12-carboxylate (23 mg, 0.04197 mmol) and ethylenesulfonyl chloride (prepared according to the procedure of C. S. Rondestredt Jr., *J. Amer. Chem. Soc.*, 76, 1926 (1954)) (378 ul, 4,197 mmol) was stirred at 25° C. under nitrogen for 63 hours. The resulting mixture was purified by reverse-phase preparative-HPLC on a C-18 column, eluted under gradient condition with 35% acetonitrile in 0.05M aqueous trifluoroacetic acid from 0 to 10 minutes, 35% to 80% from 10 to 30 minutes, 80% to 90% from 30 to 35 minutes, and remaining 90% for another 5 minutes. The fraction with retention time of 25 minutes was collected and evaporated under reduced pressure to give 2.2 mg (8%) of the title compound (2-MeO- NSE-LEAE-NHS). MS (FAB, Thioglycerol Matrix): m/z 657 (M+1).

EXAMPLE 11

Preparation of [2,6-Dimethyl-4-(2-methoxyiminoethyl)]phenyl 2-Methoxy-5-methylbenz[b]acridinium-12-carboxylate Dichloride (2-MeO-LEAE-Imidate)

(4-Cyanoethyl-2,6-dimethyl)phenyl 2-Methoxy-benz[b]acridine-12-carboxylate

A suspension of 2-methoxy-benz[b]acridine-12-carboxylic acid from Example 7 (100 mg, 0.2941 mmol) in pyridine (15 ml) was treated with p-toluenesulfonyl chloride (112 mg, 0.5882 mmol) at 0° C. for 40 minutes, followed by addition of triethylamine (164 ul. 1.1789 mmol) and 4-cyanoethyl-2,6-dimethyl-phenol (prepared according to the procedure of E. Jexova et al, CS 158810, Jul. 15, 1975; CA 84(13):898299)(51 mg, 0.2914 mmol). After 18 hours of stirring at 25° C. under nitrogen, the reaction solution was evaporated under reduced pressure to remove the pyridine. The residue was purified on 4 preparative-TLC plates (2 mm silica gel) developed twice with ethyl acetate/hexane (3:4). The major orange band was collected and extracted with methanol/chloroform (1:30). Removal of the solvents under reduced pressure gave the title compound (75 mg, 55%). Rf 0.5 (silica gel, ethyl acetate/hexane 2:3). MS (FAB, Thioglycerol Matrix): m/z 461 (M+1).

(4-Cyanoethyl2,6-dimethyl)phenyl 2-Methoxy-5-methyl benz[b]acridinium-12-carboxylate Fluorosulfonate A solution of (4-cyanoethyl-2,6-dimethyl)phenyl 2-methoxy-benz[b]acridine-12-carboxylate (20 mg, 0.04338 mmol) in methylene chloride (1 ml) was treated with methyl flurosulfonate (17.5 ul, 0.2169 mmol) at 25° C. with stirring under nitrogen for 18 hours. The reaction mixture was added to anhydrous diethyl ether (5 ml). The resulting precipitate was collected and purified by reverse-phase preparative-HPLC on a C-18 column, eluted under gradient condition with 40% to 80% acetonitrile in 0.05M aqueous trifluoroacetic acid from 0 to 30 minutes, and remaining 80% acetonitrile for another 40 minutes. The fraction with retention time of 24 minutes was collected and evaporated under reduced pressure to give the product (15.7 mg, 65%). MS (FAB, Thioglycerol Matrix): m/z 475 (M).

[2,6-Dimethyl-4-(2-methoxyiminoethyl)]phenyl 2-methoxy- 5-methyl benz[b]acridinium-12-carboxylate Dichloride (2-MeO-LEAE-Imidate)

A solution of (4-cyanoethyl-2,6-dimethyl)phenyl 2-Methoxy-5-methyl benz[b]acridinium-12-carboxylate fluorosulfonate (4 mg, 0.00697 mmol) in anhydrous methanol (0.5 ml) was treated with anhydrous hydrogen chloride (gas) at 0° C. for 10 minutes. The reaction solution was then reduced by blowing with nitrogen to a small volume; and the concentrate was added to anhydrous diethyl ether (3 ml). The resulting precipitate was collected and washed with diethyl ether (5 ml), yielding the title compound (2-MeO-LEAE-Imidate) (1.5 mg, 37%).

PREPARATION OF THE ANALOGS OF ACRIDINIUM ESTER

EXAMPLE 12

Preparation of (4-Benzyloxycarbonyl-2,6-diisopropyl)phenyl 10-Methyl-acridinium-9-carboxylate Fluorosulfonate (DIPAE-Bz)

(4-Benzyloxycarbonyl-2,6-diisopropyl)phenyl Acridine-9-carboxylate

A mixture of acridine-9-carboxylic acid hydrochloride (74 mg, 0.33 mmol) in thionyl chloride (3 ml, 41.1 mmol) was refluxed at 110° C. under nitrogen for 2 hours. After cooling, the solution was evaporated under reduced pressure to dryness. The solid was washed with anhydrous diethyl ether (5 ml) to give acridine-9-carbonyl chloride hydrochloride. This acid chloride was dissolved in anhydrous pyridine (4 ml), followed by addition of benzyl 3,5-diisopropyl-4-hydroxy-benzoate (102 mg, 0.33 mmol) and 4-N,N-dimethylamino-pyridine (16 mg, 0.13 mmol). After 16 hours of stirring at 25° C. under nitrogen, the solution was evaporated under reduced pressure to dryness. The residue was purified on a Chromatotron plate (1 mm silica gel) by elution with 20% diethyl ether/hexane to yield (4 -benzyloxycarbonyl-2,6-diisopropyl)phenyl acridine-9-carboxylate (64 mg, 38%). Rf 0.6 (silica gel, 20% ethyl acetate/toluene). MS(EI): m/z 517(M).

(4-Benzyloxycarbonyl-2,6-diisopropyl)phenyl 10-Methyl-acridinium-9-carboxylate Fluorosulfonate (DIPAE-Bz)

A solution of (4-benzyloxycarbonyl-2,6-diisopropyl)-phenyl acridine-9-carboxylate (62 mg, 0.120 mmol) in anhydrous methylene chloride (3 ml) was treated with methyl fluorosulfonate (97 ul, 1.198 mmol). After 21 hours of stirring at 25° C. under nitrogen, the solution was treated with anhydrous diethyl ether (10 ml). The resulting precipitate was collected, washed with diethyl ether (20 ml) and crystallized from acetonitrile/diethyl ether to give (4-benzyloxycarbonyl-2,6-diisopropyl)-phenyl 10-methylacridinium-9-carboxylate fluorosulfonate (DIPAE-Bz) (20 mg, 26%)

EXAMPLE 13

Preparation of (4-Benzyloxycarbonyl-2,6-dimethyl)phenyl 3-Methoxy-10-methyl-acridinium-9-carboxylate Fluorosulfonate (3-MeO-DMAE-Bz)

Methyl 3-Methoxy-acridine-9-carboxylate

To a solution of 3-hydroxy-acridine-9-carboxylic acid (2 g, 8,368 mmol) in methyl sulfoxide (50 ml) was added at 25° C. cesium carbonate (10.9 g, 33.47 mmol), followed by slow addition of iodomethane (2.08 ml, 33.47 mmol). After 2 hours of stirring at 25° C. under nitrogen, the mixture was poured into water (500 ml). The precipitate was collected, washed with water (200 ml) and air-dried. The resulting mixture was flash-chromatographed on silica column packed with chloroform and eluted with 1% methanol/chloroform, followed by 2% methanol/chloroform, to give the crude product. This crude product was further purified on six preparative-TLC plates (2 mm silica gel) by elution with 5% methanol/chloroform. The major band was collected and extracted with 5% methanol/chloroform. Removal of the solvents under reduced pressure gave methyl 3-methoxyacridine-9-carboxylate (1.05 g, 47%). Rf 0.7 (silica gel, 5% methanol/chloroform).

3-Methoxy-acridine-9-carboxylic Acid Hydrochloride

A solution of methyl 3-methoxy-acridine-9-carboxylate (900 mg, 3.37 mmol) in 4N sodium hydroxide (10 ml) and methanol (30 ml) was stirred at 65° C. under nitrogen for 14 hours, cooled and evaporated under reduced pressure to dryness. The solid was dissolved in water (100 ml); the aqueous solution was washed with diethyl ether (4×50 ml) and acidified in an ice-water bath with concentrated HCl to pH 3. The resulting precipitate was collected, washed with water (200 ml) and air-dried, to give 3-methoxy-acridine-9-carboxylic acid hydrochloride (710 mg, 73%). Rf 0.6 (silica gel, chloroform/methanol/water 65:25:4).

(4-Benzyloxycarbonyl-2,6-dimethylphenyl 3-Methoxyacridine-9-carboxylate

To a suspension of 3-methoxy-acridine-9-carboxylic acid hydrochloride (150 mg, 0,519 mmol) in pyridine (25 ml) was added at 0° C. p-toluenesulfonyl chloride (198 mg, 1.038 mmol). After stirred for 10 minutes, the suspension turned homogeneous; and then benzyl 3,5-dimethyl-4-hydroxybenzoate (132 mg, 0,519 mmol) was added. The solution was stirred at 65° C. under nitrogen for 2 hours and at 25° C. for additional 20 hours, and evaporated under reduced pressure to dryness. The residue was suspended in chloroform (100 ml), washed with 5% ammonium hydroxide (4×50 ml), water (2×50 ml), brine (1×50 ml) and dried over anhydrous magnesium sulfate. Removal of the chloroform under reduced pressure gave a crude mixture, which was purified on 2 preparative-TLC plates (2 mm silica gel) developed with toluene/ethyl acetate (4:1). The major band was collected and extracted with 10% methanol/chloroform. Evaporation of the solvents under reduced pressure yielded (4-benzyloxycarbonyl-2,6-dimethyl)phenyl 3-methoxy-acridine-9-carboxylate. Rf 0.7 (silica gel, 20% ethyl acetate/toluene). MS: (CI CH$_4$) m/z 492 (M+1).

(4-Benzyloxycarbonyl-2,6-dimethylphenyl 3-Methoxy-10-methyl-acridinium-9-carboxylate Fluorosulfonate (3-MeO-DMAE-Bz)

A solution of (4-benzyloxycarbonyl-2,6-dimethyl)phenyl 3-methoxy-acridine-9-carboxylate (45 mg, 0.0916 mmol) in anhydrous methylene chloride (2 ml) was treated with fluoromethyl sulfonate (74 ul, 0,916 mmol). After 19 hours of stirring at 25° C. under nitrogen, the solution was treated with anhydrous diethyl ether (6 ml). The resulting precipitate was collected and washed with diethyl ether (20 ml), yielding (4-benzyloxycarbonyl-2,6-dimethyl)phenyl 3-methoxy-10-methyl-acridinium-9-carboxylate fluorosulfonate (3-MeO-DMAE-Bz) (41 mg, 74%). MS (FAB, Thioglycerol Matrix): m/z 506 (M) .

EXAMPLE 14

SYNTHESIS OF AN ABAC

The preparations of an angular benz[a]acridinium ester, (4-benzyloxycarbonyl-2,6-dimethyl)phenyl 5-methylbenz[a]acridinium-12-carboxylate methosulfate and the intermediates are given below:

Benz[a]acridine-12-carboxylic acid

The procedure is essentially that reported by Martinet, J. and Dansette, A. in Bull. Soc. Chim., Fr., 45, 101 (1929).

N-Phenyl-$\beta$-naphthylamine (22.9 g, 0.1 mol) (Aldrich, Cat#17,805-5) was mixed with diethylketomalonate (18 g, 0.1 mol) (Aldrich, Cat#D9,740-1) in 5 ml of acetic acid and heated in an oil bath at 150° C. for 45 mins. The reaction mixture solidified upon cooling. The solid was transferred to a fritted funnel, washed thoroughly with ethyl alcohol, and dried in a desiccator under vacuum to give ethyl phenyl-1-benzo-4,5-dioxindol-3-carboxylate: mp 169°–170° C. A portion of this first intermediate (7 g, 0.02 mol) was further treated with 100 ml of 10% KOH, heated at reflux for 90 minutes and left at room temperature overnight. To this second reaction mixture was added 200 ml of 1 N HCl. The resulting yellow precipitate was filtered, washed with boiling ethanol, dried to give 2.1 g (33.8%) of the title compound. MS (CI, CH4): m/z 274 (M+1).

Benz[a]acridine-12-carbonyl chloride

To benz[a]acridine-12-carboxylic acid (1 g, 3.66 mmol) obtained above was added 10 ml of thionyl chloride. The mixture was heated at 95° C. for 3 hours, cooled, treated with 50 ml of benzene, and stored at 4° C. overnight. The precipitates were collected by filtration, washed with benzene, then ethyl ether, and dried in a desiccator under vacuum to give 300 mg (28%) of the acid chloride.

(4-Benzyloxycarbonyl-2,6-dimethyl)phenyl 5-methylbenz[a]acridinium-12-carboxylate methosulfate A solution of 4-benzyloxycarbonyl-2,6-dimethylphenol (0.27 g, 1 mmol) in 10 ml of dry pyridine was treated with 32 mg, 0.26 mmol of 4-dimethylaminopyridine (Aldrich, Cat.#10,770-0). To this solution was added benz[a]acridine-12-carbonyl chloride prepared above. The solution was heated at 100° C. for 3 hours and evaporated to give a residue which was purified on 3 preparative TLC plates (EM Cat#5717) developed with 5% methanol in toluene/ethyl acetate (4:1) mixture. A fluorescent band with Rf slightly below that of the starting phenol was stripped, eluted with 5% methanol in chloroform, and the eluent evaporated to give 433 mg of yellow intermediate, (4-benzyloxycarbonyl-2,6-dimethyl)phenyl benz[a]acridine-12-carboxylate.

This intermediate was dissolved in 20 ml of trichloromethane, treated with 4 ml of dimethyl sulfate and heated at 85° C. for 48 hours and cooled. The yellow precipitate was filtered and washed with ether to give 222 mg (37%) of the desired product. MS (FAB Thioglycerol Matrix): m/z 526 (M)).

PREPARATION OF CONJUGATES

In the chemiluminescent compounds of the present invention, preferably at the $R_6$ position, depending on which coupling moiety is selected, the AFAC label can be reacted directly with the specific binding partner, ligand, or hapten either in an aqueous or an organic medium.

It is understood that alternate positions of the chemiluminescent compound may have a coupling moiety to be reacted with a binding partner to form a conjugate.

The chemiluminescent labels can include an appropriate leaving group or an electrophilic functional group attached with a leaving group or functional groups which can be readily converted into such reactive groups, directly attached or connected via a spacer for attaching a substance to form a conjugate to be utilized in a test assay. An example of preparing the LEAE-anti-TSH conjugate is provided below.

Preparation of LEAE-Anti-TSH conjugate

A solution of a monoclonal anti-TSH antibody (2 mg, 0.013 umol) in 1.36 ml of 0.1M phosphate buffer, pH 8.0 was treated with a solution of LEAE-NHS (43 ug, 0.067 umole) in 240 ul of acetonitrile at room temperature for one hour. The conjugation reaction was stopped by adding a solution of lysine (10 mg) in 0.5 ml of 0.1 M phosphate buffer, pH 8.

The LEAE-conjugated anti-TSH was purified by passing the reaction mixture through a Sephadex G-25 column (1×20 cm) packed and eluted with 10 mM Phosphate, pH 8. The elution was monitored at 280 nm with a ISCO UV detector. The desired conjugate was collected when the first void volume peak was eluted out.

Preparation of Oligonucleotide conjugate

A method for conjugating binding parties, haptens, or ligands of luminescent labels to polynucleotides is described in EP-A-O 537 994 (priority U.S. Ser. No. 775,399, filed Oct. 16, 1991), which is commonly assigned and incorporated herein by reference.

LIGHT EMISSION SPECTRA

The light emission spectra of LBAC's and the reference acridinium esters were determined by a Fast Spectral Scanning System (FSSS) of Photo Research (a division of Kollmorgen Corp) of Burbank, Calif., U.S.A. The experiment was carried out in a dark room. Each sample was dissolved in HPLC grade acetonitrile at the concentration of 1 mg/ml or higher and diluted with the same solvent to obtain the sample solution in the concentration specified. A typical determination utilized 10 to 100 ug of each compound, with the exception of the angular benz[a]acridinium ester (2 mg), separately or mixed together in 0.5 ml acetonitrile contained in 13×100 mm borosilicate test tube. The tube was placed on a tube rack raised to a proper height. The FSSS optical head was placed in front of the tube at close distance and with its lense focused on the liquid in the tube. The sample solution was first treated with 0.35 ml of the Flashing Reagent #1 (Ciba Corning Diagnostics) containing 0.1 N $HNO_3$ and 0.1% $H_2O_2$. The room was then darkened, and 0.35 ml of the Flashing Reagent #2 (Ciba Corning Diagnostics) containing 0.25 N NaOH and 0.2% ARQUAD was added to the reaction mixture immediately, see U.S. Pat. No. 4,927,769 which is commonly assigned and incorporated herein by reference. The light which was generated instantaneously following the addition of the Reagent #2 was recorded by FSSS for 4 seconds except for 2-MeO-LEAE-Imidate which was recorded for 30 seconds starting from split second before the Reagent #2 was added. The results of the various determinations are summarized in Table I.

TABLE I

| Compound | Quantity | Emission Max ~(nm) | Range* (nm) |
|---|---|---|---|
| 1. DMAE-Bz | 20 ug | 426–428 | 410–510 |
| 2. 3-MeO-DMAE-Bz | 50 ug | 422 | 395–520 |
| 3. DIPAE-Bz | 20 ug | 426 | 405–520 |
| 4. ABAC^ | 2 mg | 436–440 | 410–530 |
| 5. LEAE-Bz | 50 ug | 520–524 | 490–670 |
| 6. DIP-LEAE-Bz | 50 ug | 520 | 485–670 |
| 7. 2-MeO-LEAE-Bz | 30 ug | 550 | 510–700 |
| 8. 3-EtO-LEAE-Bz | 50 ug | 508 | 470–660 |
| 9. 3-QAE-LEAE-Bz | 100 ug | 544 | 470–680 |
| 10. 2-QAE-LEAE-NHS | 70 ug | 550 | 510–700 |
| 11. LEAC-Bz | 50 ug | 520 | 485–670 |
| 12. NSP-LEAE-Bz | 15 ug | 516 | 482–655 |

TABLE I-continued

| Compound | Quantity | Emission Max ~(nm) | Range* (nm) |
|---|---|---|---|
| 13. 2-MeO-NSE-LEAE-NHS | 50 ug | 546 | 500–700 |
| 14. 2-MeO-LEAE-Imidate | 100 ug | 550 | 500–710 |

~The emission maximum for each compound could vary by 0–4 nm between different determinations.
*Range is set for spectral region with signal intensity of above 5% of peak height.
^ The ABAC is (4-Benzyloxycarbonyl-2,6-dimethyl)phenyl 5-methyl-benz[a]acridinium-12-carboxylate methosulfate.

Recorded emission spectra are shown in FIGS. 2A–2E, 3A–3J, and 4A–4D. FIGS. 2A–2E and 3A–3J show individual emission spectra of chemiluminiscent compounds including an acridinium ring system and compounds including a benzacridinium ring system. The difference of the emission maxima between acridinium esters and LBAC's were found to range between 80–128 nm, while that between acridinium esters and the ABAC was about 8–14 nm. As shown in FIGS. 4A–4D, when the acridinium esters and LBAC's were mixed in a tube and flashed simultaneously, the resulting combined emission spectra showed the ideal summed up spectral profile, indicative of the non-interfering nature of these two groups of chemiluminescent emission signals. It is understood that these data may vary depending on the instrumentation utilized and the components of the instrumentation, particularly the filters. The major portions of the original constituting spectra which remained unchanged were indeed non-overlapping. These important physical characteristics fulfill the prerequisite for two or more subclasses of chemiluminescent compounds to be utilized in test assays for detecting and/or quantitating at least two substances in a test sample, and particularly to multianalyte clinical diagnostic assays. In the preferred method a benzacridinium compound is utilized as one component of the assay method and more specifically an N-alkylated benzacridinium compound.

As noted above, a luminometer for detecting and/or quantitating at least two chemiluminescent emission spectra is described in U.S. Ser. No. 08/035,341.

LIGHT EMITTING EFFICIENCY

The light emitting efficiency of LBAC's, ABAC, and DMAE-Bz was determined on a Berthold luminometer (MLA-I) (Ciba Corning Diagnostics Corp.) fitted with a BG-38 filter with wavelength transmission range of about 320 to 650 nm at transmission efficiency of 20 to 97%. (FIG. 5, Panel A). Alternate filters may be incorporated in luminometers to expand the range of transmission efficiency.

Each sample was prepared in acetonitrile solution at 1 mg/ml, serially diluted to 10 ug/ml in acetonitrile and further on to 1 ng/ml, 0.1 ng/ml and 0.01 ng/ml in 10 mM phosphate buffer with 0.15M NaCl, 0.1% BSA. 0.05% $NaN_3$, pH8.

To determine the light emitting efficiency, 25 ul of blank (the buffer matrix) or each sample were flashed by injecting 0.35 ml each of the Flashing Reagent #1 and #2 sequentially. Light emission was integrated for 2 seconds and results as means of duplicate determination are given in Table II.

TABLE II

| Compound (counter ion) | Molecular Weight | Total Counts (RLU's)/2 sec amount flashed (pg) | | | RLU's/mol* (1 × E20) |
|---|---|---|---|---|---|
| | | 0.25 pg | 2.5 pg | 25.0 pg | |
| DMAE-Bz ($CH_3SO_4^-$) | 587 | 76,477 | 769,477 | 6,786,57 | 1.8 |
| DIPAE-Bz ($FSO_3^-$) | 631 | 82,115 | 845,660 | 6,041,380 | 2.1 |
| 3-MeO-DMAE-Bz ($FSO_3^-$) | 605 | — | 54,760 | 523,380 | 0.13 |
| ABAC^ ($CH_3SO_4^-$) | 613 | — | 23,600 | 143,400 | 0.058 |
| LEAE-Bz ($FSO_3^-$) | 625 | 105,857 | 1,037,943 | 9,037,063 | 2.6 |
| DIP-LEAE-Bz ($FSO_3^-$) | 681 | 29,930 | 240,610 | 2,413,320 | 0.66 |
| LEAC-Bz ($FSO_3^-$) | 766 | 79,873 | 767,553 | 6,312,163 | 2.4 |
| 3-EtO-LEAE-Bz ($FSO_3^-$) | 669 | 93,635 | 883,785 | 6,364,935 | 2.4 |
| 3-QAE-LEAE-Bz ($FSO_3^-$) | 854 | 16,765 | 107,540 | 1,005,855 | 0.37 |
| 2-MeO-LEAE-Bz ($FSO_3^-$) | 655 | 27,810 | 223,995 | 2,140,890 | 0.59 |
| 2-QAE-LEAE-NHS ($FSO_3^-$) | 854 | ND~ | ND~ | ND~ | ND~ |
| NSP-LEAE-Bz | 633 | 22,715 | 212,485 | 2,250,520 | 0.54 |
| 2-MeO-NSE-LEAE-NHS | 646 | 14,853 | 145,403 | 1,503,100 | 0.38 |
| 2-MeO-LEAE-Imidate (2 Cl~) | 578 | ND~ | ND~ | ND~ | ND~ |

*counts/mol calculated from quantity of 2.5 pg.
^ The ABAC is (4-Benzyloxycarbonyl-2,6-dimethyl)phenyl 5-methyl-benz[a]acridinium-12-carboxylate methosulfate.
~ND = not determined prior to the establishment of final purity of the compound.

From the data shown in Table II, the light emitting efficiency of the LBAC's was comparable to that of DMAE-Bz within the range of 0.21 to 1.39 fold, depending on the substituents on the benzacridinium nucleus and the phenoxy group. It should be noted these determinations were based on 2-second signal collection and have not taken into account the flashing kinetics of the individual compounds, e.g. some compounds may take greater that 2 seconds to release most of their signals, the sensitivity of the photomultiplying tube, and the transmission efficiency of the optical filter(s) at different points of the spectral range. These findings, however, were totally unexpected in view of the much lower light emitting efficiency of the isomeric ABAC. This level of light emitting efficiency renders LEAC's useful in sensitive binding assays, including multi-analyte assays..

KINETIC STUDY ON LIGHT EMISSION

Due to the electronic and/or steric effects of different substituents on the phenoxy moiety, the acridinium and benzacridinium nucleus, it was anticipated that not all the DMAE analogs, ABAC and LEAC's would have the same flashing rates under identical conditions. In other words, within 2 seconds of signal collection time different compounds were expected to release different percentages of total releasable signals. A time course study over a period of up to 10 seconds was conducted to determine these percentages, by flashing the compounds and normalizing all the signals collected for different lengths of time to that of 10 seconds. The results are summarized in Table III.

TABLE III

| | Percent signal released over different lengths of time | | | | | |
|---|---|---|---|---|---|---|
| Compounds | 10.0 s | 6.0 s | 4.0 s | 2.0 s | 1.0 s | 0.5 s |
| DMAE-Bz | 100% | 99% | 96% | 80% | 48% | 10% |
| DIPAE-Bz | 100% | 98% | 97% | 89% | 64% | 14% |
| 3-MeO-DMAE-Bz | 100% | 80% | 70% | 57% | 49% | 26% |
| ABAC^ | 100% | 89% | 73% | 52% | 20% | 3% |
| LEAE-Bz | 100% | 98% | 97% | 88% | 71% | 27% |
| DIP-LEAE-Bz | 100% | 80% | 67% | 47% | 26% | 4% |
| LEAC-Bz | 100% | 102% | 98% | 93% | 82% | 73% |
| 3-EtO-LEAE-Bz | 100% | 95% | 93% | 85% | 78% | 45% |
| 3-QAE-LEAE-Bz | 100% | 91% | 88% | 84% | 75% | 34% |
| 2-MeO-LEAE-Bz | 100% | 92% | 83% | 65% | 42% | 16% |
| 2-QAE-LEAE-NHS | 100% | 88% | 76% | 59% | 37% | 9% |
| NSP-LEAE-Bz | 100% | 95% | 96% | 91% | 72% | 14% |
| 2-MeO-NSE-LEAE-NHS | 100% | 96% | 90% | 79% | 58% | 22% |
| 2-MeO-LEAE-Imidate | 100% | 76% | 59% | 40% | 23% | 6% |

^ The ABAC is (4-Benzyloxycarbonyl-2,6-dimethyl)phenyl 5-methyl-benz[a]acridinium-12-carboxylate methosulfate.

As shown by the data of TABLE III, particularly at the 0.5 and 1 second intervals, the flashing kinetics varied widely for different DMAE analogs, ABAC and LEAC's. These data on release percentages should be utilized in comparing the light emission efficiency of the compounds for developing various assay utilizing the chemiluminescent compounds.

MUTUALLY NON-INTERFERING LIGHT EMISSION

Beside exhibiting discernable mutually non-interfering nature of their light emission spectra as mentioned above, DMAE and LEAE in the form of protein conjugates also demonstrated no mutual interactions in their light emissions during flashing as shown by no decrease or increase of the combined Relative Light Units (RLU) registered.

The testing was carried out as follows:

DMAE-anti-TSH and LEAE-anti-TSH were diluted in 10 mM phosphate buffer with 0.15M NaCl, 0.1% BSA, 0.05% NaN$_3$, pH 8 at two concentrations, such that 25 ul of the solutions would give about 200,000 and 1,000,000 RLU's, respectively, when they were flashed in the same manner on the Berthold luminometer equipped as described above. The light emission of each sample (25 ul) was measured separately and then the same volume of each were combined and measured again. In single sample determinations, an additional equal volume of the buffer was added to maintain the same sample volume as in the combined sample determinations. Results of the testing are summarized in Table IV.

TABLE IV

| Single sample determination* (RLU) | | Combined sample determination* (RLU) | |
|---|---|---|---|
| DMAE-anti-TSH | LEAE-anti-TSH | Theoretical | Found (%) |
| 860,617 | 1,017,200 | 1,877,817 | 1,835,350 (98%) |
| 173,200 | 191,820 | 365,029 | 362,293 (99%) |

*Each value was the mean of triplicate determinations. (RLU - Relative light units)

The results in Table IV show that the two tracers of different emission spectra were absolutely non-interfering between each other in their light emission. This characteristic further ensures their utility in multi-analyte binding assays. The LEAE of the preferred method is a N-alkylated benzacridinium compound.

STABILITY of CONJUGATED LBAC'S

LBAC-Anti-TSH conjugates were prepared and tested for their stability in aqueous media. DMAE-anti-TSH conjugate was also tested side by side. The retention of chemiluminescent activity as a function of temperature at various pH's (using citrate-phosphate buffer containing 0.1% BSA) was monitored over 7 day period. Proper concentrations of the above conjugates (0.8–1.4×10$^6$ RLU's/25 ul) were placed in two sets of different buffers (pH 7.4, 8.0, 8.5, and 9.0). One set was kept at 4°–8° C. as a control, while the other was subjected to 37° C. The buffered samples (25 ul) were flashed periodically as described above. The results are summarized in Table V.

TABLE V

| pH | Compds^ | Relative Stability* of Conjugates | | | |
|---|---|---|---|---|---|
| | | 1 day | 3 days | 5 days | 7 days |
| 7.4 | I | 93% | 98% | 91% | 95% |
| | II | 66% | 56% | 51% | 44% |
| | III | 67% | 78% | 77% | 80% |
| | IV | 89% | 94% | 101% | 96% |
| | V | | 66% | | 46% |
| 8.0 | I | 99% | 104% | 96% | 98% |
| | II | 106% | 106% | 80% | 83% |
| | III | 79% | 69% | 68% | 71% |
| | IV | 102% | 114% | 140% | 138% |
| | V | | 45% | | 13% |
| 8.5 | I | 92% | 102% | 89% | 81% |
| | II | 111% | 97% | 110% | 82% |
| | III | 81% | 76% | 78% | 86% |
| | IV | 134% | 142% | 150% | 156% |
| 9.0 | I | 90% | 95% | 70% | 71% |
| | III | 94% | 68% | 51% | 71% |

TABLE V-continued

| pH | Compds | Relative Stability* of Conjugates | | | |
|---|---|---|---|---|---|
| | | 1 day | 3 days | 5 days | 7 days |
| | IV | 133% | 140% | 149% | 130% |

^ Compounds I–V are DMAE-anti-TSH, LEAE-anti-TSH, 2-MeO-LEAE anti-TSH, 3-Eto-LEAE-anti-TSH, and Non-ortho-substituted AE-anti-TSH, respectively. The stability data for Non-ortho-substituted AE-anti-TSH were equivalent to that reported earlier in U.S. Pat. No. 4,745,181.
*Relative Stability is defined by expressing the percentage chemiluminescent activity of 37° C. samples relative to that of the corresponding 4–8° C. samples. For example, at pH 8, after 7 days of storage, the DMAE-anti-TSH and LEAE-anti-TSH 37° C. samples retained 87% and 83% activity, respectively, in comparison with the corresponding 4° C. samples, while the non-ortho-substituted acridinium ester retained only 13% activity in comparison with the corresponding 4° C. sample.

The stability study summarized in Table V demonstrates that the stabilizing effect of ortho-substitution on the phenoxy ring not only applies to the class of acridinium esters, it also benefits the LBAC's series to about the same extent with regard to maintaining their chemiluminescent activity in aqueous media at or near pH 8 under prolonged heat-stress conditions as required for commercial binding assay products. Listed in great contrast is the stability data of the non-ortho-substituted acridinium ester conjugate at pH 8. A non-ortho-substituted LEAC would likely also have poor stability in aqueous media.

Signal-to-Noise in Binding Assays

LEAE-anti-TSH was employed as tracer in a TSH assay. Performance was assessed by determining signal-to-noise (S/N) ratio. The performance of DMAE-antiTSH was also compared side by side. The assay was configured as follows:

100 microliters of either of the above conjugates was incubated for two hours at room temperature with 100 ul of a TSH standard (Ciba Corning Diagnostics Corp., Medfield, Mass.). Incubations were done separately with five standards containing either 0, 0.5, 1.0, 16 or 100 uIu/ml of TSH. A second incubation was then performed by adding 500 ul of MAGIC® magnetic particle immobilized with sheep anti-TSH (Ciba Corning Diagnostics Corp.) to the above mixture, then waiting for 30 minutes at room temperature.

A wash was done first by magnetically separating the particles from the solution, decanting the solution, then adding 500 ul of water, followed by another magnetic separation. The washed particles were resuspended in 100 ul of water. Flashing and counting were done according to the above-described procedures. The results are provided in Table VI using ratios of the counts with a TSH standard containing TSH versus the zero TSH standard.

TABLE VI

| Conjugate | S/N at various Standards | | | |
|---|---|---|---|---|
| | 0.4 uIu/ml | 1.0 uIu/ml | 16 uIu/ml | 100 uIu/ml |
| DMAE-anti-TSH | 10.0 | 20.9 | 202.3 | 669.4 |
| LEAE-anti-TSH | 5.4 | 8.4 | 87.4 | 282.6 |

The results given in Table VI indicate that LEAE conjugate can be utilized in an immunoassay format to provide a dose-response curve and, therefore, allows the development of useful assays.

DUAL-ANALYTE SIMULTANEOUS IMMUNOASSAY

Instrumentation

One embodiment of a Dual-PMT Luminometer (DPL) utilized to demonstrate the hardware of DPL includes at least two photo multiplyer tube (PMT) assemblies, an injection pump for Flashing Reagent #2, and a cube-shape light tight chamber designed for holding a disposable cuvette. At two opposite sides of the chamber, two cylindrical PMT tube assemblies are separately attached such that light of two different spectral ranges generated inside the cuvette can be individually registered by the PMT assemblies. The top of the cuvette-holding chamber is hinged to allow the cuvette to be manually inserted and removed. In addition, the top also has a fixed probe attached for the purpose of injecting the Flashing Reagent #2 into the cuvette. Within each PMT assembly an optical filter selected for particular spectral range, and is inserted between the cuvette and the PMT tube.

Alternate embodiments and configurations of DPLs may be designed for semi-automated and automated detection of two or more chemiluminescent compounds or conjugates in a test sample. A luminometer as a component on an automated analyzer is described in EP-A-0 502 638 noted above.

Essential to the discrimination or discernability of two or more emitted light spectra are the choices of a plurality of optical filters with proper wavelength cut-offs.

Filters of this type are widely available from commercial vendors and may be modified, i.e. by lamination or specifically manufactured to be incorporated in a PMT assembly for detection and/or quantitation of spectral signals of the conjugates. Careful selection of filters will enhance the ability to discern emission signals and with appropriate correction may allow multiple signals with the emission overlap to be discerned.

For the purpose of running a simultaneous LH/FSH dual-immunoassay as disclosed below, a long pass filter (P/N LL-500 of Corion, Holliston, Mass.) and a short pass filter (P/N P70-450 also of Corion) were chosen to match with the two different spectral ranges of light generated from a pair of tracers, LEAE-anti-LH and DMAE-anti-FSH, which were prepared in the same manner as described above for LEAE-anti-TSH and DMAE-antiTSH, respectively. The transmittance curves for the two filters are shown in FIG. 5, panels B and C. The choice of the optical filters should take into consideration the requirements on maximal signal transmittance and minimal signal cross-talk. Optical filters with more desirable transmittance profile and cut-off may be selected to maximize the transmission of light emitted from the tracers and/or to fit better with the emission spectral ranges of particular chemiluminescent compounds so as to improve the Percent Cross Talk (PCT) as described below. For example Corion's laminated CS550/CS600 filter (FIG. 5, panel D) was found to be a better replacement for filter P70-450 as the short pass filter matching with the long pass filter LL-500 for the determination of the pair of DMAE and LEAE tracers. Not only was the registered RLU's for DMAE tracer found to increase by more than 2 fold as a result of this filter's use, the Percentage Cross Talks, as shown in Table VII, were also greatly improved. Furthermore, as more LEAE derivatives with even longer emission maxima were developed, e.g. 2-MeO-LEAE, long pass filters such as LL-520 (FIG. 5 E) would be a better choice than filter LL-500 for enabling further reduction of the PCT.

For system controlling, which generally includes the basic functions of parameter setting, execution and registration of flashing, signal correction as described below as a function of filters used and the chemiluminescent compounds utilized, and data display, a personal computer unit containing proper software is utilized and connected to the DPL.

Percentage Cross-Talks (POT's) Determination

Figure 6:
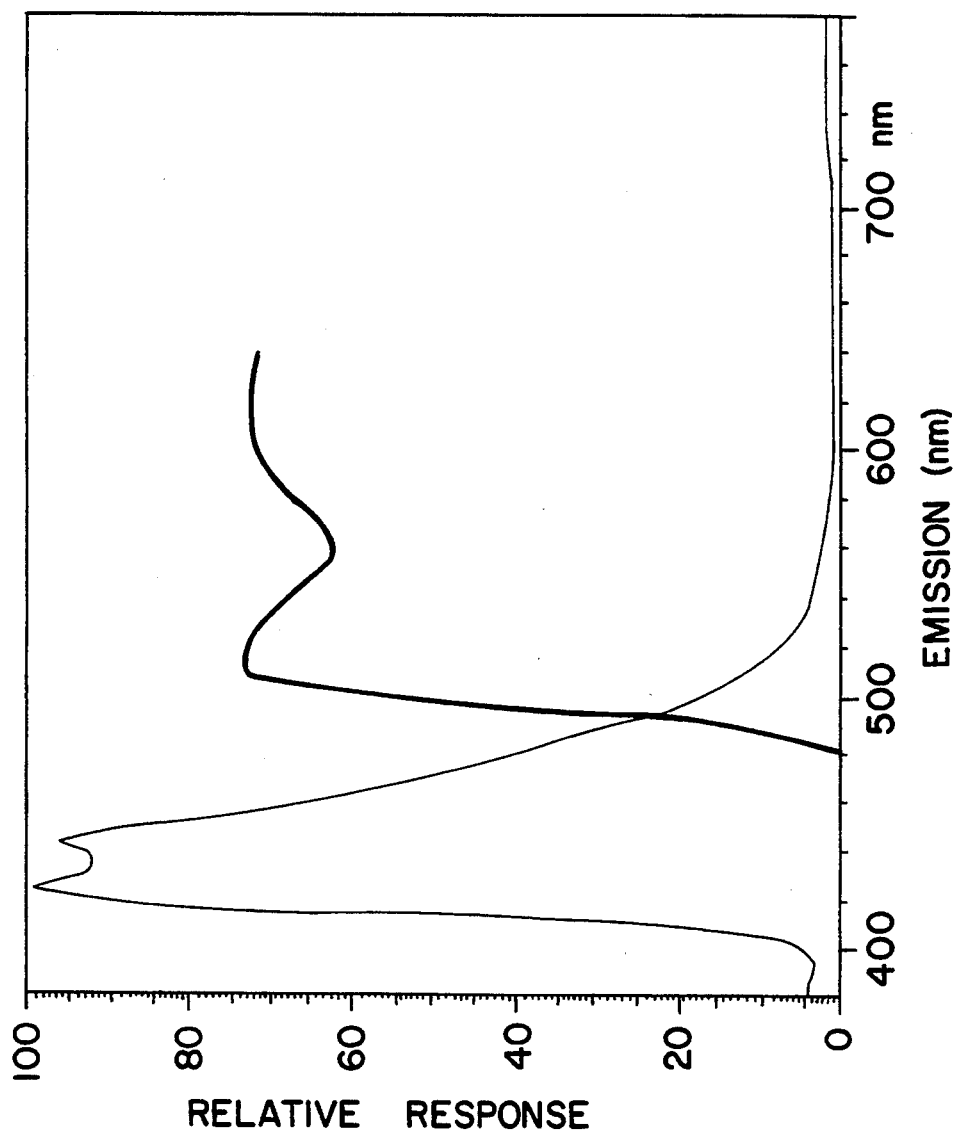
FIG. 6 illustrates the area of overlap between the transmittance curve of an optical filter (Corion LL500) and the emission spectra of DMAE-Bz.

As mentioned above the two optical filters installed in two separate PMT assemblies on the DPL were intended to gate the emitted lights of two different spectral ranges: the long pass filter is to match with the longer emission from LEAE tracer and the short pass filter with the shorter emission from DMAE tracer. However, as illustrated by FIGS. 6 and 7, because of the minor overlap between the transmittance curves and the emission spectra of the cross-matching pairs, light signals generated by one tracer can be picked up by the primary PMT intended for it but also in small percentage by the secondary PMT intended for the other tracer, and vice versa. That portion of signal of one tracer, that can be registered by the secondary PMT, must be quantitated separately in term of percentage for each tracer prior to their use in a dual-analyte immunoassay, in order that the apparent RLU's can be corrected and the pure signal of each tracer detected by each PMT assembly be obtained when the two tracers were flashed simultaneously in the same tube.

Table VII shows the determined PCT's of several pairs of tracers. Anti-FSH-DMAE and anti-LH-LEAE were used in the simultaneous LH/FSH dual-analyte assay described below. Other pairs of tracers were included to demonstrate that through the selection of acridinium and benzacridinium compounds of wider separation in their emission maxima and proper choice of optical filters, minimal PCT's ideal for multi-analyte assay can be realized. The PCT's were obtained by dividing the minor signal from the secondary PMT by the major signal from the primary PMT in each case, and multiplying the results by 100%.

The concentrations of the samples were randomly selected such that the primary signals fell in the range of 100,000 to 1,500,000 RLU's per 25 ul sample. Each determination was made by sequentially pipeting 25 ul of one tracer solution, 300 ul of Flashing Reagent #1 into the cuvette, vortexing the resulting solution briefly, inserting the cuvette into the PMT housing, and performing the flashing by injecting 300 ul of Flashing Reagent #2 through the key-board control.

TABLE VII

Determination of Percent Cross-Talk (PCT)

| Sample | Long Pass Signals (RLU's) | Short Pass Signals (RLU's) | PCT (%) |
|---|---|---|---|
| SET (I)*: | | | |
| LH tracer | 538 | 688 | |
| diluent | 444 | 396 | |
| Anti-LH-LEAE | 6.25 E5 | 4.18 E4 | 6.7 |
| | 5.78 E5 | 3.91 E4 | 6.8 |
| | 6.19 E5 | 4.18 E4 | 6.8 |
| | | Aver. | 6.8 |
| FSH tracer | 242 | 288 | |
| diluent | 268 | 340 | |
| Anti-FSH-DMAE | 2.32 E4 | 1.59 E5 | 14.5 |
| | 2.42 E4 | 1.65 E5 | 14.7 |

TABLE VII-continued

Determination of Percent Cross-Talk (PCT)

| Sample | Long Pass Signals (RLU's) | Short Pass Signals (RLU's) | PCT (%) | |
|---|---|---|---|---|
| | 2.60 E4 | 1.75 E5 | 14.8 | |
| | | | Aver. | 14.7 |
| SET (II)^ : | | | | |
| Anti-LH-LEAE | 1.27 E6 | 5.52 E4 | 4.4 | |
| | 1.25 E6 | 5.40 E4 | 4.3 | |
| | | | Ave. | 4.4 |
| Anti-FSH-DMAE | 4.62 E4 | 4.28 E5 | 10.8 | |
| | 4.60 E4 | 4.23 E5 | 10.9 | |
| | | | Ave. | 10.9 |
| SET (III)+: | | | | |
| Buffer~ | 348 | 278 | | |
| | 350 | 284 | | |
| Anti-TSH-2-MeO-LEAE | 9.90 E5 | 1.29 E4 | 1.3 | |
| | 9.88 E5 | 1.29 E4 | 1.3 | |
| | | | Ave. | 1.3 |
| Anti-FSH-DMAE | 1.17 E4 | 3.77 E5 | 3.1 | |
| | 1.17 E4 | 3.81 E5 | 3.1 | |
| | | | Ave. | 3.1 |
| SET (IV)#: | | | | |
| Buffer~ | 187 | 608 | | |
| | 182 | 429 | | |
| Anti-TSH-2-MeO-LEAE | 2.12 E5 | 6.26 E3 | 2.9 | |
| | 2.0 E5 | 5.95 E3 | 2.9 | |
| | | | Aver. | 2.9 |
| Anti-TSH-DMAE | 2.93 E4 | 5.39 E5 | 5.4 | |
| | 3.12 E4 | 5.83 E5 | 5.4 | |
| | | | Aver. | 5.4 |

*Optical filters mounted on the DPL: LL-500 & P70-450.
^Optical filters mounted on the DPL: LL-500 & Laminated CS-550/CS-600.
+Optical filters mounted on the DPL: LL-520 & Laminated CS-550/CS-600.
Optical filters mounted on the DPL: LL-520 & P70-450.
~The buffer was 10 mM PBS/0.1% BSA/0.05% NaN$_3$, pH 8.0.

The constancy of the PCT over a wide range of RLU's is critical in the multi-analyte assay signal correction. Table VIII shows that when the laminated CS550/CS600 filter and LL520 filter were used to gate the short pass and long pass signals, respectively, the PCT for anti-TSH-DMAE has the mean of 2.96% with standard deviation of 0.16% over RLU range of 10,000 to 7,000,000 counts or broader, while the PCT for anti-CKMB-LEAE has the mean of 4.79% with standard deviation of 0.23% over RLU range of 50,000 to 7,000,000 counts or broader.

TABLE VIII

Constancy of Percent Cross-Talk

| Sample | Short Pass Signal (RLU's) | Long Pass Signal (RLU's) | PCT (%) | Mean/SD (%) |
|---|---|---|---|---|
| Anti-TSH-DMAE | 6,689,796 | 217,010 | 3.24 | |
| | 6,545,872 | 212,956 | 3.25 | |
| | 6,645,674 | 210,262 | 3.16 | |
| | 1,469,500 | 43,710 | 2.97 | |
| | 1,469,770 | 45,004 | 3.06 | |
| | 1,450,042 | 43,492 | 3.00 | |
| | 303,944 | 8,922 | 2.81* | |
| | 302,876 | 8,788 | 2.78* | |
| | 287,632 | 8,928 | 2.98* | |
| | 59,468 | 2,106 | 2.95* | |
| | 58,816 | 2,072 | 2.93* | |
| | 60,314 | 1,996 | 2.73* | |
| | 12,298 | 692 | 2.77* | |
| | 11,956 | 692 | 2.86* | |
| | 12,420 | 716 | 2.96* | 2.96/0.16 |
| Buffer Diluent | 738 | 496 | | |
| | 702 | 320 | | |
| Anti-CKMB-LEAE | 320,758 | 6,663,484 | 4.81 | |
| | 315,344 | 6,497,756 | 4.85 | |
| | 320,224 | 6,528,242 | 4.91 | |
| | 61,374 | 1,350,584 | 4.54 | |
| | 61,514 | 1,329,548 | 4.63 | |
| | 60,036 | 1,330,152 | 4.51 | |
| | 13,044 | 264,526 | 4.71* | |
| | 11,968 | 244,106 | 4.67* | |
| | 12,324 | 245,542 | 4.78* | |
| | 3,312 | 56,120 | 4.84* | |
| | 3,586 | 54,906 | 5.45* | |
| | 3,220 | 53,928 | 4.87* | 4.79/0.23 |
| Buffer Diluent | 652 | 372 | | |
| | 622 | 346 | | |

*Correction was made in consideration of the additional signal contributed by the buffer and system noise.

Equations for Correcting the Apparent RLU's due to Cross-Talks in Dual-Tracer Determination When DMAE and LEAE derivatives or tracers are mixed and flashed simultaneously, the observed long and short pass signals can be broken down as follows:

$$S(s) = S(DMAE) + S'(LEAE) + b1 \quad (1)$$

$$S(l) = S(LEAE) + S'(DMAE) + b2 \quad (2)$$

Where, $S(s)$ and $S(l)$ are the observed short and long pass signals, respectively; $S(DMAE)$ and $S(LEAE)$ are the portions of signals due to DMAE and LEAE in the observed short and long pass signals, respectively. They will also be referred to as the corrected DMAE and LEAE signals; $S'(DMAE)$ and $S'(LEAE)$ are portions of the long and short pass signals due to DMAE and LEAE cross-talking, respectively; b1 and b2 are the combined signals due to assay components and system noise in the absence of DMAE and LEAE tracers, respectively.

Since the PCT's (represented by k1 and k2 below) are constants for any particular DMAE and LEAE tracers, there exist the following relationships:

$$S'(DMAE) = k1 \times S(DMAE) \quad (3)$$

$$S'(LEAE) = k2 \times S(LEAE) \quad (4)$$

Where k1, k2 are the PCT's for the DMAE and LEAE tracers, respectively.

Substitute equation (4) into (1):

$$S(s) = S(DMAE) + k2 \times S(LEAE) + b1 \text{ or}$$
$$S(DMAE) = S(s) - k2 \times S(LEAE) - b1 \quad (5)$$

Substitute equations (5) into (3) and (3) into (2):

$$S(l) = S(LEAE) + k1 \times [S(s) - k2 \times S(LEAE)] - b1 + b2 =$$
$$S(LEAE) + k1 \times S(s) - k1 \times k2 \times S(LEAE) - k1 \times b1 + b2$$

Rearranging:

$$S(l) - k1 \times S(s) + k1 \times b1 - b2 = S(LEAE) - k1 \times k2 \times S(LEAE)$$

$$= S(LEAE) \times (1 - k1 \times k2)$$

-continued $$S(LEAE) = \frac{S(l) - k1 \times S(s) + k1 \times b1 - b2}{1 - k1 \times k2} \quad (6)$$

Equations (5) and (6) will yield the corrected short pass signal due to DMAE tracer and long pass signal due to LEAE tracer, respectively. For the purpose of demonstrating the feasibility of conducting a simultaneous LH/FSH dual-analyte assay, the determination of the combined matrix and system noises, b1 and b2 was found not to be significant. They were therefore both assigned a 0 value in the signal corrections for the following examples of the dual-analyte assays.

Simultaneous Immunoassay for Luteinizing Hormone (LH) and Follicle Stimulating Hormone (FSH)

One objective of the invention is to provide a method for simultaneously detecting and/or quantitating two or more substances or analytes in a single sample through the utilization of two different chemiluminescent labels or conjugates.

In an example of one embodiment, the assay system utilizes a DMAE labelled FSH antibody and a LEAE labelled LH antibody. The following examples demonstrate that LH and FSH standard curves and sample recovery are identical within the limits of experimental error when each analyte is assayed as a single analyte by introduction of one chemiluminescent tracer into the assay system, or in a dual analyte system which employs two chemiluminescent tracers.

The examples further show that tracers prepared from a pair of a DMAE and a LEAC can be utilized in a simultaneous assay of two substances for which a corresponding binding partner, e.g. antibody, is available.

EXAMPLE 15

Single FSH assay using Dual-Analyte Immunoassay System

The Magic Lite FSH kit components and protocol (Ciba Corning Diagnostics) were modified such that the assay could be performed as a single or dual analyte assay depending on the tracer selection. A solid phase consisting of paramagnetic particles (PMP) coupled to anti-FSH antibodies and PMP coupled to anti-LH antibodies was prepared by removing the buffer diluent from the Magic Lite FSH kit solid phase and resuspending these particles in Magic Lite LH kit solid phase (Ciba Corning Diagnostics Corp.). The kit tracer, anti-FSH-DMAE, was diluted 1:2 in Magic Lite LH kit tracer buffer. Standards for calibration contained both FSH and LH. Standards were prepared by spiking known concentrations of purified human FSH and human LH into a horse serum basepool. Nominal standard values were 0, 0.9, 2.2, 4.4, 8.8, 21.9, 43.8, 87.5, 140.0, 201.0 mIu/ml of FSH. Nominal LH concentrations were 0, 1.0, 2.5, 5.0, 10.0, 25.0, 50.0, 100.0, 160.0, 230.0 mIu/ml LH. Samples for analysis were prepared by spiking a human serum pool with varying concentrations of both purified human FSH and human LH. Additionally, serum based multi-constituent calibrators containing human FSH and human LH were used as samples.

To perform the assay, 50 ul of each standard or sample and 200 ul of diluted FSH tracer were vortex mixed and incubated for 30 minutes at room temperature. 500 ul of the combined anti-FSH/anti-LH solid phase was added, vortex mixed and incubated for 30 minutes at room temperature. The reacted solid phase was magnetically separated for 3 minutes in a Magic Lite rack (Ciba Corning Diagnostics Corp.), see European Patent 136126, and the supernatant decanted. The reacted solid phase was next washed with 1.0 ml of distilled water, separated for 3 minutes. The supernatant was decanted, and 100 ul of distilled water added. Each sample was manually transferred to a cuvette, and counted for 5 seconds on the DPL described above. The results (in RLU's) obtained from the short pass (DMAE) channel were used to calculate FSH concentration in each sample. Concentrations were calculated by using 10-point calibration with a spline data reduction routine. Each standard and sample was assayed in replicates of three. RLU's and % CVC for this assay are shown in Table IX under the heading FSH single-analyte assay. FSH sample recovery is shown in Table X under the heading FSH single-analyte assay. The FSH standard curve presented as % B/Bmax vs log FSH concentration is shown in FIG. 8 labelled as FSH single-analyte assay.

EXAMPLE 16

Single LH Assay using Dual-analyte Immunoassay System

The solid phase reagent, standards, and samples described in Example 15 were used to perform an LH assay. The anti-FSH-DMAE tracer was replaced with an anti-LH-LEAE tracer which was diluted 1:2 in Magic Lite FSH kit tracer diluent. The assay methodology described in Example 13 was applied to this assay, except that the RLU results obtained from the Long pass (LEAE) channel were used to calculate LH sample concentrations.

The assay was calibrated using nine of the standards described in Example 15, excluding the 1.0 mIu/ml LH standard. Results for this assay are shown in Table XI and Table XII under the heading LH single-analyte assay. The standard curve is shown in FIG. 9 labelled as LH single-analyte assay.

EXAMPLE 17

Simultaneous LH/FSH Assay using Dual-analyte Immunoassay System

Solid phase reagent, standards, and samples described in Example 15 and 16 were used to perform a dual label LH/FSH assay in a single tube. The tracer consisted of the Magic Lite FSH kit tracer, anti-FSH-DMAE diluted 1:2 in the anti-LH-LEAE tracer. The assay methodology was the same as that described in Example 15. The raw RLU's from each channel was mathematically corrected for cross-talk prior to concentration calculations. Corrected RLU's and concentrations resulting from these corrected RLU's are shown in Tables IX--XII, and are labelled as dual-analyte assay. Mean sample recovery for single analyte vs. dual analyte assays are compared by t-test in Tables X and XII. The FSH and LH standard curves are shown in FIGS. 8 and 9 and labelled as FSH and LH dual-analyte assay, respectively.

Assays and Assay Formats

The present invention relates to chemiluminescent compounds and more particularly, the use of two or more chemiluminescent conjugates to simultaneously detect two or more substances in a test sample. The disclosure teaches the use of benzacridinium compounds and preferably N-alkylated benzacridinium compounds in such assays.

A test substance includes any component(s) or analytes sought to be detected and/or quantitated in a test sample, including but not limited to, more than one component of a single structure, e.g. more than one portion of a nucleic acid sequence or different loci of a chromosome, genome or molecule, where the components or analytes may be of biological or industrial origin, such as nucleic acids, proteins, ligands, haptens or other materials or compounds to which an appropriate assay method can be formatted. It is understood that the test sample and/or substance may need to be pretreated to render it assayable by a test method. The test substances and quantities thereof sought to be detected may limit the types of assays which can be performed because of, for example, sensitivity concerns, but not the use of chemiluminescent labels for detection. Various internal standards or controls may be added to a test sample for detection and/or quantitation to assess the performance of the assay. Diagnostic assays exemplified by immunoassays, hybridization assays and amplification assays have increasingly incorporated chemiluminescent labels in their formats. Designs and formats of such assays are well known by those skilled in the art and extensively published in the technical and patent literature, for example, an assay format may require the separation of a reaction product or unreacted agent to a transfer tube for detection and/or quantitation. Such separation techniques may be useful for competitive assays, solid phase assays or to limit interferents.

In one embodiment of the invention, two or more chemiluminescent conjugates are utilized as labels in an amplification assay. Representative amplification assays include but should not be limited to polymerase chain reaction (PCR), autocatalytic replication of recombinant RNA and amplification of midivariant DNA or RNA. See EP-A-O 481 704 (priority U.S. Ser. No. 598,269 (Oct. 16, 1990), abandoned) which is commonly assigned and incorporated herein by reference. Such methods, as taught in the technical and patent may be made adaptable to incorporate chemiluminescent labels, and particularly two or more chemiluminescent labels for detection of target sequences of interest. The advantage of using a multi-label method is to detect and/or quantitate a plurality of target sequences or one or more target sequences and an internal standard. An example of such a method includes providing a test sample suspected of containing one or more target sequences, amplifying the target sequences, providing at least two chemiluminescent conjugates, each chemiluminescent conjugate being associated with a target sequence(s) and simultaneously detecting and/or quantifying amplified target sequences by emissions of at least two chemiluminescent conjugates. In another step of this method an internal reference, control or control system may be added to the assay to insure assay performance and results. The internal reference may be amplified as well as the target sequences.

The use of chemiluminescent labels for such assays serves to demonstrate the utility of this invention.

The chemiluminescent compounds of this invention are adapted to be packaged in kit form for commercial sale. The chemiluminescent labels of these kits may be conjugated to appropriate substances or materials which are specific to the substances sought to be detected in the test samples. Appropriate functional groups may be added to the chemiluminescent compounds for use in various assays and other applications. Examples of assays for which the methods of the present invention may be utilized include but should not be limited to: assays including at least two antibodies of different specifities; assays including at least two antigens; assays including at least one antigen and at least one antibody; and assays for molecules indicative of cancer, infectious diseases, genetic abnormalities, genetic disposition, genetic assessment and to monitor medicinal therapy.

It is to be understood that various other modifications will be apparent to and can readily be made by those skilled in the art, given the disclosure herein, without departing from the scope and materials of this invention. It is not, however, intended that the scope of the claims appended hereto be limited to the description as set forth herein, but rather that the claims be construed as encompassing all features of patentable novelty which reside in the present invention, including all features which would be treated as equivalents thereof by those skilled in the art to which the invention pertains. It is also noted that the examples given therein are intended to illustrate, and not to limit the invention.

TABLE IX

MEAN RLU's and % CVC FOR MODIFIED MAGIC LITE FSH ASSAYS

| SAMPLE (VALUE) | FSH SINGLE ANALYTE ASSAY | | FSH RESULTS DUAL ANALYTE ASSAY* | |
|---|---|---|---|---|
| | MEAN RLU | % CVC | MEAN RLU | % CVC |
| S1 (0) | 1336 | 4.3 | 610 | 6.7 |
| S2 (0.9) | 1891 | 5 | 1309 | 14.4 |
| S3 (2.2) | 3202 | 10.9 | 2375 | 6.7 |
| S4 (4.4) | 5155 | 9.4 | 4189 | 3.9 |
| S5 (8.8) | 9005 | 2.6 | 7702 | 2.4 |
| S6 (21.9) | 19637 | 5.5 | 16942 | 5.2 |
| S7 (43.8) | 35491 | 0.7 | 30563 | 4 |
| S8 (87.5) | 56844 | 1.7 | 51969 | 5 |
| S9 (140.0) | 74850 | 0.9 | 66499 | 0.5 |
| S10 (201.0) | 87531 | 0.8 | 77003 | 0.5 |
| SAMPLE 1 | 9962 | 7.3 | 8417 | 2.8 |
| SAMPLE 2 | 16779 | 4.9 | 14777 | 0.8 |
| SAMPLE 3 | 29683 | 13 | 28721 | 4.5 |
| SAMPLE 4 | 62549 | 2.2 | 55878 | 2.4 |
| SAMPLE 5 | 93019 | 1.1 | 84182 | 3.3 |
| SAMPLE 6 | 103290 | 3 | 93297 | 1.2 |
| LOW MULTI-CAL | 1756 | 9 | 1160 | 9.8 |
| HIGH MULTI-CAL | 80308 | 2.4 | 71082 | 0.6 |
| TOTAL COUNTS | 564200 | | 571392 | |

*corrected RLU

TABLE X

FSH SAMPLE RECOVERY: SINGLE ANALYTE ASSAY VS. DUAL ANALYTE ASSAY

| SAMPLE | FSH SINGLE ANALYTE ASSAY | | FSH DUAL ANALYTE ASSAY | | CRITICAL T-VALUE 95% C.I. | |
|---|---|---|---|---|---|---|
| | MIU/ML | % CVD | MIU/ML | % CVD | T-VALUE | |
| SAMPLE 1 | 9.923 | 8.6 | 9.737 | 3.2 | 0.36 | +/−4.30 |
| SAMPLE 2 | 18.291 | 5.7 | 18.668 | 1 | 0.62 | +/−4.30 |
| SAMPLE 3 | 35.235 | 15.1 | 40.708 | 5.3 | −1.65 | +/−4.30 |

TABLE X-continued

FSH SAMPLE RECOVERY: SINGLE ANALYTE ASSAY VS. DUAL ANALYTE ASSAY

| SAMPLE | FSH SINGLE ANALYTE ASSAY | | FSH DUAL ANALYTE ASSAY | | CRITICAL T-VALUE 95% C.I. | |
| --- | --- | --- | --- | --- | --- | --- |
| | MIU/ML | % CVD | MIU/ML | % CVD | T-VALUE | |
| SAMPLE 4 | 101.951 | 3.5 | 98.877 | 4.2 | 0.98 | +/−3.18 |
| SAMPLE 5 | >> | | >> | | | |
| SAMPLE 6 | >> | | >> | | | |
| MULTI-CAL LOW | 0.693 | 30.8 | 0.697 | 20.1 | −0.2 | +/−3.18 |
| MULTI-CAL HIGH | 163.132 | 5.4 | 163.812 | 1.4 | −0.13 | +/−4.30 |

TABLE XI

MEAN RLU's AND % CVC FOR MODIFIED MAGIC LITE LH ASSAYS

| SAMPLE (VALUE) | LH SINGLE ANALYTE ASSAY | | LH RESULTS DUAL ANALYTE ASSAY* | |
| --- | --- | --- | --- | --- |
| | MEAN RLU | % CVC | MEAN RLU | % CVC |
| S1 (0) | 17,883 | 14.2 | 18,477 | 10.6 |
| S3 (2.5) | 24,310 | 1.9 | 22,818 | 2.7 |
| S4 (5.0) | 27,007 | 6.5 | 25,118 | 11.9 |
| S5 (10.0) | 34,713 | 11.6 | 28,934 | 6.2 |
| S6 (25.0) | 42,440 | 4.6 | 41,543 | 5.3 |
| S7 (50.0) | 65,787 | 2.9 | 71,140 | 6.2 |
| S8 (100.0) | 115,760 | 6.8 | 113,694 | 1.9 |
| S9 (160.0) | 161,767 | 4.4 | 164,225 | 4.4 |
| S10 (230.0) | 223,569 | 4.8 | 205,347 | 4.5 |
| SAMPLE 4 | 42,157 | 2.8 | 40,519 | 8.2 |
| SAMPLE 5 | 82,934 | 4.3 | 83,592 | 5.5 |
| SAMPLE 6 | 110,502 | 2.8 | 113,285 | 1.9 |
| MULTI-CAL HIGH | 86,189 | 3.5 | 90,451 | 2.9 |
| TOTAL COUNTS | 2,250,526 | | 2,322,672 | |

*CORRECTED RLU

TABLE XII

LH SAMPLE RECOVERY: SINGLE ANALYTE ASSAY VS. DUAL ASSAY

| SAMPLE | LH SINGLE ANALYTE ASSAY | | LH RESULTS DUAL ANALYTE ASSAY* | | | CRITICAL T-VALUE 95% C.I. |
| --- | --- | --- | --- | --- | --- | --- |
| | MIU/ML | % CVD | MIU/ML | % CVD | T-VALUE | |
| SAMPLE 4 | 21.347 | 7 | 22.342 | 15.3 | −0.46 | +/−4.30 |
| SAMPLE 5 | 67.392 | 5.7 | 64.829 | 7.5 | 0.72 | +/−3.18 |
| SAMPLE 6 | 97.375 | 3.6 | 97.984 | 2.5 | −0.25 | +/−3.18 |
| MULTI-CAL HIGH | 70.906 | 4.5 | 72.153 | 4 | −0.5 | +/−3.18 |

The invention having thus been described, what is claimed as new and desired to secure by Letters Patent is:

1. A detection and/or quantitation method for at least two substances in a test sample comprising:
   (a) providing at least two different chemiluminescent compounds, wherein at least one of said compounds includes a linear aromatic four-ring fused acridinium compound, and another includes an angular aromatic four-ring fused acridinium compound or a three-ring acridinium compound, each of said compounds having conjugated thereto a molecule specific for a test substance in said test sample so that a reaction will occur between said conjugated molecule and test substance; and
   (b) simultaneously detecting the emission signals of said chemiluminescent compounds, wherein said signals are utilized to detect and/or quantitate the said test substances.

2. A detection method as recited in claim 1, wherein each of said chemiluminescent compounds are conjugated to a binding partner which is specific for and binds to a test substance to form a reaction product to be detected and/or quantitated in the test sample.

3. A detection method as recited in claim 2, wherein the emission spectra of said chemiluminescent conjugates are discernable in that their emission maxima are spaced apart a sufficient distance to discern the signals of each conjugate.

4. A detection and/or quantitation method as recited in claim 2, wherein the emission spectra of said chemiluminescent conjugates are discernable in that their emission maxima are spaced greater than 60 nanometers apart.

5. A detection and/or quantitation method as recited in claim 1, wherein each of the emission spectra have a width of 100 to 250 nm.

6. A detection and/or quantitation method as recited in claim 1, wherein an additional test substance is introduced into the test sample for detection and/or quantitation wherein said added substance functions as a control or an internal reference.

7. A detection and/or quantitation method as recited in claim 1, wherein said method is performed in a single reaction medium or a tube.

8. A detection and/or quantitation method as recited in claim 1, wherein said method is an immunoassay, hybridization assay, or a nucleic acid amplification assay.

9. A detection and/or quantitation method as recited in claim 8, wherein said immunoassays are homogeneous or heterogeneous.

10. A detection and/or quantitation method as recited in claim 1, wherein at least one chemiluminescent compound includes an N-alkylated benzacridinium four-ring system.

11. A detection and/or quantitation method as recited in claim 1, wherein at least one chemiluminescent compound includes an acridinium three-ring system.

12. An amplification method for target sequences in a test sample comprising:
   (a) providing a test sample suspected of containing one or more target sequences;
   (b) adding an internal reference or control to said test sample;
   (c) amplifying the target sequences;

(d) providing at least two different chemiluminescent conjugates, each chemiluminescent conjugate having bound thereto a molecule complementary to one of said target sequence, internal reference or control, such that a detectable product is produced; wherein at least one conjugate includes a linear aromatic four-ring fused acridinium compound and another includes an angular aromatic four-ring fused acridinium compound or a three-ring acridinium compound; and (e) simultaneously detecting and/or quantitating amplified target sequences and the internal reference or control by emissions of said chemiluminescent conjugates.

13. An amplification method as recited in claim 12, wherein said internal reference is a target sequence that is not amplified.

14. An amplification method as recited in claim 12, wherein said internal reference is a target sequence that is amplified.

15. An amplification method as recited in claim 12, further comprising the step(s) of performing at least one binding reaction specific to a target sequence of the test sample.

16. An amplification method as recited in claim 12, further comprising the step(s) of performing at least one binding reaction specific to the internal reference.

17. An amplification method as recited in claim 15 or 16, wherein said binding reaction is a hybridization reaction.

18. An amplification method as recited in claim 12, wherein at least one chemiluminescent compound includes a N-alkylated benzacridinium ring system.

19. An amplification method as recited in claim 12, wherein at least one chemiluminescent compound includes an acridinium three-ring system.

20. An amplification method for target sequences in a test sample comprising:

(a) providing a test sample suspected of containing one or more target sequences;

(b) amplifying the target sequences;

(c) providing at least two different chemiluminescent conjugates, each chemiluminescent conjugate having bound thereto a molecule complementary with a target sequence(s) such that a detectable product is produced and wherein at least one conjugate includes a linear aromatic ring fused acridinium compound and another includes an angular aromatic ring fused acridinium compound or an acridinium compound; and (d) simultaneously detecting and/or quantifying amplified target sequences by emissions of said chemiluminescent conjugates.

21. An amplification method as recited in claim 20 further comprising the steps of adding an internal reference to said test sample and detecting and/or quantitating the internal reference.

22. An amplification method as recited in claim 20, wherein at least one chemiluminescent conjugate includes a benzacridinium four-ring system.

23. An amplification method as recited in claim 20, wherein at least one chemiluminescent conjugate includes an acridinium three-ring system.

24. A chemiluminescent label assay method for detection and/or quantitating at least two substances in a test sample comprising:

(a) providing a first chemiluminescent reagent to the test sample, said first chemiluminescent reagent including a benzacridinium four-ring system and which is specific to one test substance in said test sample;

(b) providing a second chemiluminescent reagent to the test sample, said second chemiluminscent reagent including a three-ring acridinium ring system and which is specific to another test substance in said test sample; and (c) activating said chemiluminescent reagents to provide discernable emission signals for detecting and/or quantitating the test substances.

25. A method as recited in claim 24, wherein said benzacridinium ring system is a N-alkylated benzacridinium ring system.

26. A method as recited in claim 24, wherein said method further includes a binding reaction step and wherein each chemiluminescent reagent further includes a conjugated molecule specific for a test substance to be detected in a test sample to enable a binding reaction between said molecule and a test substance to occur.

* * * * *